(12) United States Patent
Ferren et al.

(10) Patent No.: US 7,998,060 B2
(45) Date of Patent: Aug. 16, 2011

(54) LUMEN-TRAVELING DELIVERY DEVICE

(75) Inventors: Bran Ferren, Beverly Hills, CA (US);
W. Daniel Hillis, Encino, CA (US);
Roderick A. Hyde, Redmond, WA (US);
Muriel Y. Ishikawa, Livermore, CA (US); Edward K. Y. Jung, Bellevue, WA (US); Eric C. Leuthardt, St. Louis, MO (US); Nathan P. Myhrvold, Medina, WA (US); Elizabeth A. Sweeney, Seattle, WA (US); Clarence T. Tegreene, Bellevue, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1176 days.

(21) Appl. No.: 11/651,946

(22) Filed: Jan. 9, 2007

(65) Prior Publication Data
US 2007/0225634 A1     Sep. 27, 2007

Related U.S. Application Data

(63) Continuation-in-part of application No. 10/949,186, filed on Sep. 24, 2004, and a continuation-in-part of application No. 10/827,576, filed on Apr. 19, 2004, and a continuation-in-part of application No. 10/827,578, filed on Apr. 19, 2004, and a continuation-in-part of application No. 10/827,572, filed on Apr. 19, 2004, now Pat. No. 7,850,676, and a continuation-in-part of application No. 10/827,390, filed on Apr. 19, 2004, and a continuation-in-part of application No. 11/403,230, filed on Apr. 12, 2006, and a continuation-in-part of application No. 11/417,898, filed on May 4, 2006, and a continuation-in-part of application No. 11/478,368, filed on Jun. 28, 2006, and a continuation-in-part of application No. 11/485,619, filed on Jul. 11, 2006, and a continuation-in-part of application No. 11/645,357, filed on Dec. 21, 2006, now Pat. No. 7,857,767, and a continuation-in-part of application No. 11/645,358, filed on Dec. 21, 2006.

(51) Int. Cl.
*A61B 1/00* (2006.01)
*A61K 9/22* (2006.01)
(52) U.S. Cl. .................................... 600/114; 604/891.1
(58) Field of Classification Search .................. 600/114, 600/115; 604/890.1, 891.1, 40–43, 514, 604/65–67, 93.01, 95.01–95.05
See application file for complete search history.

(56) References Cited

U.S. PATENT DOCUMENTS
3,391,697 A      7/1968   Greatbatch
(Continued)

FOREIGN PATENT DOCUMENTS
CN        99810271.7      10/2001
(Continued)

OTHER PUBLICATIONS

UK Intellectual Property Office Examination Report Under Section 18(3); App. No. GB0821519.6; Nov. 12, 2009; 1-4.
(Continued)

*Primary Examiner* — Theodore J Stigell
*Assistant Examiner* — Laura C Schell

(57) ABSTRACT

Lumen-traveling devices capable of controlled material release and associated methods and systems are described. Lumen-traveling devices capable of traveling within a body lumen may include a propelling mechanism to produce movement of the lumen-traveling device within the lumen, as well as additional components such as a sensor, a material release portion, and/or control circuitry. In some embodiments, a sensor may be used to detect a local condition, and a material may be released from the device in response.

29 Claims, 57 Drawing Sheets

U.S. PATENT DOCUMENTS

| | | |
|---|---|---|
| 3,837,339 A | 9/1974 | Aisenberg et al. |
| 4,267,831 A | 5/1981 | Aguilar |
| 4,367,741 A | 1/1983 | Michaels |
| 4,585,652 A | 4/1986 | Miller et al. |
| 4,628,928 A | 12/1986 | Lowell |
| 4,714,460 A | 12/1987 | Calderon |
| 4,717,381 A | 1/1988 | Papantonakos |
| 4,763,667 A | 8/1988 | Manzo |
| 4,769,006 A | 9/1988 | Papantonakos |
| 4,771,772 A | 9/1988 | DeWitt |
| 4,800,898 A | 1/1989 | Hess et al. |
| 4,817,601 A | 4/1989 | Roth et al. |
| 4,871,351 A | 10/1989 | Feingold |
| 4,905,689 A | 3/1990 | Stack et al. |
| 4,944,659 A | 7/1990 | Labbe et al. |
| 4,994,071 A | 2/1991 | MacGregor |
| 5,019,372 A | 5/1991 | Folkman et al. |
| 5,153,827 A | 10/1992 | Coutre et al. |
| 5,176,638 A | 1/1993 | Don Michael |
| 5,188,111 A | 2/1993 | Yates et al. |
| 5,234,457 A | 8/1993 | Andersen |
| 5,269,303 A | 12/1993 | Wernicke et al. |
| 5,279,607 A | 1/1994 | Schentag et al. |
| 5,310,404 A | 5/1994 | Gyory et al. |
| 5,314,451 A | 5/1994 | Mulier |
| 5,335,657 A | 8/1994 | Terry, Jr. et al. |
| 5,337,732 A | 8/1994 | Grundfest et al. |
| 5,338,625 A | 8/1994 | Bates et al. |
| 5,339,051 A | 8/1994 | Koehler et al. |
| 5,353,807 A | 10/1994 | DeMarco |
| 5,374,285 A | 12/1994 | Vaiani et al. |
| 5,386,741 A | 2/1995 | Rennex |
| 5,395,390 A | 3/1995 | Simon et al. |
| 5,398,670 A | 3/1995 | Ortiz et al. |
| 5,403,311 A | 4/1995 | Abele et al. |
| 5,411,551 A | 5/1995 | Winston et al. |
| 5,437,660 A | 8/1995 | Johnson et al. |
| 5,476,450 A | 12/1995 | Ruggio |
| 5,497,147 A | 3/1996 | Arms et al. |
| 5,522,394 A | 6/1996 | Zurbrügg |
| 5,551,953 A | 9/1996 | Lattin et al. |
| 5,554,914 A | 9/1996 | Miyazawa |
| 5,569,968 A | 10/1996 | Lal et al. |
| 5,574,347 A | 11/1996 | Neubauer |
| 5,593,434 A | 1/1997 | Williams |
| 5,599,324 A | 2/1997 | McAlister et al. |
| 5,610,488 A | 3/1997 | Miyazawa |
| 5,624,398 A | 4/1997 | Smith et al. |
| 5,632,754 A | 5/1997 | Farley et al. |
| 5,643,296 A | 7/1997 | Hundertmark et al. |
| 5,662,587 A * | 9/1997 | Grundfest et al. ............ 600/114 |
| 5,669,874 A | 9/1997 | Feiring |
| 5,674,276 A | 10/1997 | Andersen et al. |
| 5,688,269 A | 11/1997 | Newton et al. |
| 5,695,457 A | 12/1997 | St. Goar et al. |
| 5,697,967 A | 12/1997 | Dinh et al. |
| 5,702,432 A | 12/1997 | Chen et al. |
| 5,705,293 A | 1/1998 | Hobson |
| 5,728,089 A | 3/1998 | Lal et al. |
| 5,737,279 A | 4/1998 | Carter |
| 5,782,798 A | 7/1998 | Rise |
| 5,804,563 A | 9/1998 | Still et al. |
| 5,807,395 A | 9/1998 | Mulier et al. |
| 5,819,736 A | 10/1998 | Avny et al. |
| 5,827,190 A | 10/1998 | Palcic et al. |
| 5,830,179 A | 11/1998 | Mikus et al. |
| 5,830,207 A | 11/1998 | Leeb et al. |
| 5,831,012 A | 11/1998 | Nilsson et al. |
| 5,833,603 A | 11/1998 | Kovacs et al. |
| 5,843,139 A | 12/1998 | Goedeke et al. |
| 5,855,801 A | 1/1999 | Lin et al. |
| 5,873,835 A | 2/1999 | Hastings et al. |
| 5,908,027 A | 6/1999 | Butterfield et al. |
| 5,921,982 A | 7/1999 | Lesh et al. |
| 5,947,119 A | 9/1999 | Reznick |
| 5,951,600 A | 9/1999 | Lemelson |
| 5,954,675 A | 9/1999 | Dellagatta |
| 5,964,773 A | 10/1999 | Greenstein |
| 6,004,269 A | 12/1999 | Crowley et al. |
| 6,016,449 A | 1/2000 | Fischell et al. |
| 6,019,729 A | 2/2000 | Itoigawa et al. |
| 6,022,316 A | 2/2000 | Eppstein et al. |
| 6,053,873 A | 4/2000 | Govari et al. |
| 6,086,528 A | 7/2000 | Adair |
| 6,102,845 A | 8/2000 | Woodard et al. |
| 6,111,520 A | 8/2000 | Allen et al. |
| 6,128,538 A | 10/2000 | Fischell et al. |
| 6,134,474 A | 10/2000 | Fischell et al. |
| 6,149,603 A | 11/2000 | Parker |
| 6,159,230 A | 12/2000 | Samuels |
| 6,164,284 A | 12/2000 | Schulman et al. |
| 6,170,488 B1 | 1/2001 | Spillman, Jr. et al. |
| 6,179,789 B1 | 1/2001 | Tu et al. |
| 6,185,452 B1 | 2/2001 | Schulman et al. |
| 6,186,986 B1 | 2/2001 | Berg et al. |
| 6,187,599 B1 | 2/2001 | Asher et al. |
| 6,197,013 B1 | 3/2001 | Reed et al. |
| 6,219,577 B1 | 4/2001 | Brown, III et al. |
| 6,221,099 B1 | 4/2001 | Andersen et al. |
| 6,240,312 B1 | 5/2001 | Alfano et al. |
| 6,240,316 B1 | 5/2001 | Richmond et al. |
| 6,248,345 B1 | 6/2001 | Goldenheim et al. |
| 6,249,076 B1 | 6/2001 | Madden et al. |
| 6,255,361 B1 | 7/2001 | Rajagopalan et al. |
| 6,278,379 B1 | 8/2001 | Allen et al. |
| 6,295,990 B1 | 10/2001 | Lewis et al. |
| 6,296,638 B1 | 10/2001 | Davison et al. |
| 6,322,532 B1 | 11/2001 | D'Sa et al. |
| 6,337,997 B1 | 1/2002 | Rise |
| 6,372,248 B1 | 4/2002 | Qin et al. |
| 6,383,162 B1 | 5/2002 | Sugarbaker |
| 6,384,741 B1 | 5/2002 | O'Leary, Sr. |
| 6,385,472 B1 | 5/2002 | Hall et al. |
| 6,398,280 B1 | 6/2002 | Parker et al. |
| 6,402,678 B1 | 6/2002 | Fischell et al. |
| 6,409,674 B1 | 6/2002 | Brockway et al. |
| 6,436,120 B1 | 8/2002 | Meglin |
| 6,442,413 B1 | 8/2002 | Silver |
| 6,450,937 B1 | 9/2002 | Mercereau et al. |
| 6,453,199 B1 | 9/2002 | Kobozev |
| 6,464,687 B1 | 10/2002 | Ishikawa et al. |
| 6,475,639 B2 | 11/2002 | Shahinpoor et al. |
| 6,490,483 B2 | 12/2002 | Willis |
| 6,497,714 B1 | 12/2002 | Ishikawa et al. |
| 6,500,174 B1 | 12/2002 | Maguire et al. |
| 6,512,949 B1 | 1/2003 | Combs et al. |
| 6,512,950 B2 | 1/2003 | Li et al. |
| 6,514,237 B1 | 2/2003 | Maseda |
| 6,530,950 B1 | 3/2003 | Alvarado et al. |
| 6,547,825 B1 | 4/2003 | Shimizu et al. |
| 6,548,982 B1 | 4/2003 | Papanikolopoulos et al. |
| 6,554,798 B1 | 4/2003 | Mann et al. |
| 6,575,969 B1 | 6/2003 | Rittman, III et al. |
| 6,585,763 B1 | 7/2003 | Keilman et al. |
| 6,591,137 B1 | 7/2003 | Fischell et al. |
| 6,592,567 B1 | 7/2003 | Levin et al. |
| 6,597,954 B1 | 7/2003 | Pless et al. |
| 6,607,553 B1 | 8/2003 | Healy et al. |
| 6,616,676 B2 | 9/2003 | Bashiri et al. |
| 6,623,519 B2 | 9/2003 | Edwin et al. |
| 6,632,216 B2 | 10/2003 | Houzego et al. |
| 6,638,273 B1 | 10/2003 | Farley et al. |
| 6,648,908 B2 | 11/2003 | Dobak, III et al. |
| 6,666,860 B1 | 12/2003 | Takahashi |
| 6,669,683 B2 | 12/2003 | Santini, Jr. et al. |
| 6,673,042 B1 | 1/2004 | Samson et al. |
| 6,673,363 B2 | 1/2004 | Luo et al. |
| 6,679,893 B1 | 1/2004 | Tran |
| 6,709,388 B1 | 3/2004 | Mosse et al. |
| 6,711,423 B2 | 3/2004 | Colvin, Jr. |
| 6,712,835 B2 | 3/2004 | Mazzocchi et al. |
| 6,719,684 B2 | 4/2004 | Kim et al. |
| 6,735,474 B1 | 5/2004 | Loeb et al. |
| 6,735,475 B1 | 5/2004 | Whitehurst et al. |
| 6,743,211 B1 | 6/2004 | Prausnitz et al. |
| 6,754,536 B2 | 6/2004 | Swoyer et al. |
| 6,755,802 B2 | 6/2004 | Bell |

| Patent/Publication | Date | Inventor(s) |
|---|---|---|
| 6,755,803 B1 | 6/2004 | Le et al. |
| 6,764,441 B2 | 7/2004 | Chiel et al. |
| 6,773,429 B2 | 8/2004 | Sheppard, Jr. et al. |
| 6,797,522 B1 | 9/2004 | Still et al. |
| 6,802,811 B1 | 10/2004 | Slepian |
| 6,824,508 B2 | 11/2004 | Kim et al. |
| 6,824,510 B2 | 11/2004 | Kim et al. |
| 6,824,561 B2 | 11/2004 | Soykan et al. |
| 6,849,183 B2 | 2/2005 | Gorsuch et al. |
| 6,855,115 B2 | 2/2005 | Fonseca et al. |
| 6,860,867 B2 | 3/2005 | Seward et al. |
| 6,861,001 B2 | 3/2005 | Lee et al. |
| 6,875,209 B2 | 4/2005 | Zvuloni et al. |
| 6,889,091 B2 | 5/2005 | Hine et al. |
| 6,890,303 B2 | 5/2005 | Fitz |
| 6,898,464 B2 | 5/2005 | Edell et al. |
| 6,911,004 B2 | 6/2005 | Kim et al. |
| 6,911,496 B2 | 6/2005 | Rhee et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | Von Alten |
| 6,936,003 B2 | 8/2005 | Iddan |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |
| 6,959,215 B2 | 10/2005 | Gliner et al. |
| 6,960,227 B2 | 11/2005 | Jones et al. |
| 6,963,792 B1 | 11/2005 | Green |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,037,343 B2 | 5/2006 | Imran |
| 7,042,184 B2 | 5/2006 | Oleynikov et al. |
| 7,066,180 B2 | 6/2006 | Aylsworth et al. |
| 7,101,386 B2 | 9/2006 | Dobak, III |
| 7,115,109 B2 | 10/2006 | Gerdts et al. |
| 7,125,382 B2 | 10/2006 | Zhou et al. |
| 7,131,979 B2 | 11/2006 | DiCarlo et al. |
| 7,160,258 B2 | 1/2007 | Imran et al. |
| 7,181,261 B2 | 2/2007 | Silver et al. |
| 7,195,641 B2 | 3/2007 | Palmaz et al. |
| 7,228,162 B2 | 6/2007 | Ward et al. |
| 7,236,821 B2 | 6/2007 | Cates et al. |
| 7,245,954 B2 | 7/2007 | Glukhovsky |
| 7,297,113 B1 | 11/2007 | Russell et al. |
| 7,341,577 B2 | 3/2008 | Gill |
| 7,365,509 B2 | 4/2008 | Park et al. |
| 7,383,071 B1 | 6/2008 | Russell et al. |
| 7,572,228 B2 | 8/2009 | Wolinsky et al. |
| 7,625,338 B2 | 12/2009 | Gilad et al. |
| 7,684,840 B2 | 3/2010 | Palti |
| 7,713,196 B2 | 5/2010 | Baker, Jr. |
| 7,736,300 B2 | 6/2010 | Ziegler et al. |
| 7,744,542 B2 | 6/2010 | Piaget et al. |
| 7,801,626 B2 | 9/2010 | Moser |
| 7,840,271 B2 | 11/2010 | Kieval et al. |
| 7,857,767 B2 | 12/2010 | Ferren et al. |
| 2001/0029348 A1 | 10/2001 | Willis |
| 2001/0051766 A1 | 12/2001 | Gazdzinski |
| 2002/0065509 A1 | 5/2002 | Lebel et al. |
| 2002/0068080 A1 | 6/2002 | Lerner |
| 2002/0090388 A1 | 7/2002 | Humes et al. |
| 2002/0116029 A1 | 8/2002 | Miller et al. |
| 2002/0116034 A1 | 8/2002 | Miller et al. |
| 2002/0147480 A1 | 10/2002 | Mamayek |
| 2002/0156462 A1 | 10/2002 | Stultz |
| 2002/0165592 A1 | 11/2002 | Glukhovsky et al. |
| 2002/0169436 A1 | 11/2002 | Gurm et al. |
| 2002/0171385 A1 | 11/2002 | Kim et al. |
| 2002/0188323 A1 | 12/2002 | Penner et al. |
| 2002/0193679 A1 | 12/2002 | Malave et al. |
| 2002/0193874 A1 | 12/2002 | Crowley |
| 2002/0198470 A1 | 12/2002 | Imran et al. |
| 2002/0198521 A1 | 12/2002 | Maguire |
| 2002/0198604 A1 | 12/2002 | Schulman et al. |
| 2003/0024534 A1 | 2/2003 | Silvestri et al. |
| 2003/0040704 A1 | 2/2003 | Dorros et al. |
| 2003/0065358 A1 | 4/2003 | Frecker et al. |
| 2003/0069475 A1 | 4/2003 | Banik et al. |
| 2003/0069523 A1 | 4/2003 | Williams et al. |
| 2003/0151524 A1 | 8/2003 | Clark |
| 2003/0152823 A1 | 8/2003 | Heller |
| 2003/0158584 A1 | 8/2003 | Cates et al. |
| 2003/0163177 A1 | 8/2003 | Eggers et al. |
| 2003/0167000 A1 | 9/2003 | Mullick et al. |
| 2003/0214579 A1 | 11/2003 | Iddan |
| 2003/0214580 A1 | 11/2003 | Iddan |
| 2003/0220556 A1 | 11/2003 | Porat et al. |
| 2004/0008853 A1 | 1/2004 | Pelrine et al. |
| 2004/0018508 A1 | 1/2004 | Friedman |
| 2004/0019374 A1 | 1/2004 | Hojeibane et al. |
| 2004/0064093 A1 | 4/2004 | Hektner et al. |
| 2004/0073177 A1 | 4/2004 | Hickle |
| 2004/0073190 A1 | 4/2004 | Deem et al. |
| 2004/0092825 A1* | 5/2004 | Madar et al. .................. 600/473 |
| 2004/0097819 A1 | 5/2004 | Duarte |
| 2004/0098030 A1 | 5/2004 | Makower et al. |
| 2004/0133147 A1 | 7/2004 | Woo |
| 2004/0138517 A1 | 7/2004 | Osorio et al. |
| 2004/0147939 A1 | 7/2004 | Rabkin et al. |
| 2004/0148034 A1 | 7/2004 | Kagan et al. |
| 2004/0162469 A1 | 8/2004 | Imran |
| 2004/0162501 A1 | 8/2004 | Imran |
| 2004/0176664 A1 | 9/2004 | Iddan |
| 2004/0199246 A1 | 10/2004 | Chu et al. |
| 2004/0225325 A1 | 11/2004 | Bonutti |
| 2004/0225326 A1 | 11/2004 | Weiner et al. |
| 2004/0260391 A1 | 12/2004 | Santini, Jr. et al. |
| 2004/0267240 A1 | 12/2004 | Gross et al. |
| 2005/0004553 A1 | 1/2005 | Douk |
| 2005/0021023 A1 | 1/2005 | Guglielmi et al. |
| 2005/0027236 A1 | 2/2005 | Douk |
| 2005/0058701 A1 | 3/2005 | Gross et al. |
| 2005/0065592 A1 | 3/2005 | Holzer |
| 2005/0069925 A1 | 3/2005 | Ford et al. |
| 2005/0079132 A1 | 4/2005 | Wang et al. |
| 2005/0107870 A1 | 5/2005 | Wang et al. |
| 2005/0113460 A1 | 5/2005 | Glick |
| 2005/0121411 A1 | 6/2005 | Cohen |
| 2005/0126916 A1 | 6/2005 | Lockard et al. |
| 2005/0149170 A1 | 7/2005 | Tassel et al. |
| 2005/0151524 A1 | 7/2005 | Sae-Ueng et al. |
| 2005/0177223 A1 | 8/2005 | Palmaz |
| 2005/0182482 A1 | 8/2005 | Wang et al. |
| 2005/0203613 A1 | 9/2005 | Arney et al. |
| 2005/0216074 A1 | 9/2005 | Sahatjian et al. |
| 2005/0221529 A1 | 10/2005 | Bang et al. |
| 2005/0228259 A1 | 10/2005 | Glukhovsky et al. |
| 2005/0234393 A1 | 10/2005 | Wood, Jr. |
| 2005/0234440 A1 | 10/2005 | Wood, Jr. |
| 2005/0238689 A1 | 10/2005 | Carpenter et al. |
| 2005/0272806 A1 | 12/2005 | Falotico et al. |
| 2005/0272974 A1 | 12/2005 | Iddan |
| 2005/0277839 A1 | 12/2005 | Alderman et al. |
| 2005/0278020 A1 | 12/2005 | Wang et al. |
| 2006/0004395 A1 | 1/2006 | Chiel et al. |
| 2006/0009810 A1 | 1/2006 | Mann et al. |
| 2006/0015146 A1 | 1/2006 | Girouard et al. |
| 2006/0037617 A1 | 2/2006 | Walke et al. |
| 2006/0074479 A1 | 4/2006 | Bailey et al. |
| 2006/0119304 A1 | 6/2006 | Farritor et al. |
| 2006/0167339 A1 | 7/2006 | Gilad et al. |
| 2007/0010868 A1 | 1/2007 | Ferren et al. |
| 2007/0066929 A1 | 3/2007 | Ferren et al. |
| 2007/0088334 A1 | 4/2007 | Hillis et al. |
| 2008/0063703 A1 | 3/2008 | Gross et al. |
| 2008/0066929 A1 | 3/2008 | Costa et al. |
| 2008/0103440 A1 | 5/2008 | Ferren et al. |
| 2008/0243056 A1 | 10/2008 | Hillis et al. |

FOREIGN PATENT DOCUMENTS

| | | |
|---|---|---|
| EP | 1 245 201 A1 | 10/2002 |
| EP | 1 618 831 A2 | 1/2006 |
| EP | 2 163 206 A1 | 3/2010 |
| JP | 2001-506871 | 3/1998 |

| | | |
|---|---|---|
| JP | 2002-153569 | 5/2002 |
| JP | 2005-74229 | 3/2005 |
| WO | WO 96/39999 | 12/1996 |
| WO | WO 98/09582 | 3/1998 |
| WO | WO 98/14243 | 4/1998 |
| WO | WO 99/20335 | 4/1999 |
| WO | WO 99/44665 | 9/1999 |
| WO | WO 00/69515 | 11/2000 |
| WO | WO 01/08548 A1 | 2/2001 |
| WO | WO 01/24731 A1 | 4/2001 |
| WO | WO 03/072157 | 9/2003 |
| WO | WO 03/090618 A2 | 11/2003 |
| WO | WO 03/106966 A2 | 12/2003 |
| WO | WO 2004/028335 A2 | 4/2004 |
| WO | WO 2004/058041 A2 | 7/2004 |
| WO | WO 2004/086958 A1 | 10/2004 |
| WO | WO 2005/082248 A1 | 9/2005 |

OTHER PUBLICATIONS

UK Intellectual Property Office Examination Report Under Section 18(3); App. No. GB0821526.1; Nov. 11, 2009; 1-5.

UK Examination Report Under Section 18(3); App. No. GB0821524.6; bearing a date of May 6, 2010; pp. 1-3.

U.S. Appl. No. 11/454,343, Jung et al.

U.S. Appl. No. 11/455,010, Jung et al.

"001_08 Comparison of Capsule Cameras: M2A (Given Imaging) vs. NORIKA3 (RF System lab)" RF System lab; bearing dates of 2001-2004; pp. 1-2; located at http://www.rfnorika.com/eng/system/sys_008.html; printed on May 4, 2006.

Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.

"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html.

"Agile new plastics change shape with heat"; MIT Tech Talk; Nov. 22, 2006; p. 5 (1 page).

Ananthaswamy, Anil; "First robot moved by muscle power"; bearing a date of Feb. 27, 2004; pp. 1-3; New Scientist; located at http://www.newscientist.com/article.ns?id=dn4714; printed on Sep. 12, 2006.

Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.

Behkam, Bahareh; Sitti, Metin; "Towards Hybrid Swimming Microrobots: Bacteria Assisted Propulsion of Polystyrene Beads"; Proceedings of the 28$^{th}$ IEEE EMBS Annual International Conference; bearing dates of Aug. 30-Sep. 3, 2006 and 2006; pp. 2421-2424; IEEE.

Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; located at www.nejm.org.

Bezrouk, A.; Hanuš, J.; Záhora, J.; "Temperature Characteristics of Nitinol Spiral Stents"; Scripta Medica (BRNO); bearing dates of Aug. 2005, Oct. 2005; pp. 219-226; vol. 78, No. 4.

Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois.

Chen, Ting; Barton, Scott Calabrese; Binyamin, Gary; Gao, Zhiqiang; Zhang, Yongchao; Kim, Hyug-Han; Heller, Adam; "A Miniature Biofuel Cell"; Journal of the American Chemical Society, Aug. 11, 2001; pp. 8630-8631; vol. 123; 2001; American Chemical Society.

Christensen, Bill; "Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006.

Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.

Costamagna; Guido M.D.; "PillCam™ SB Capsule Endoscopy"; Given Imaging.com; bearing dates of 2001-2006; pp. 1-4; located at http://www.givenimaging.com/Cultures/en-US/Given/English/Products/CapsuleEndoscopy/; printed on May 4, 2006.

Dario, P.; Carrozza, M.C.; Lencioni, L.; Magnani, B.; D'Attanasio, S.; "A Micro Robotic System for Colonoscopy"; Proceedings of the 1997 IEEE International Conference on Robotics and Automation; bearing dates of Apr. 1997 and 1997; pp. 1567-1572; IEEE.

Dongxiang, Chi; Guozheng, Yan; "An earthworm based miniature robot for intestinal inspection"; Proceedings of SPIE; bearing dates of Nov. 7-9, 2001; pp. 396-400; vol. 4601; SPIE.

Freitas Jr., Robert A.; "8.2.1.2 Arteriocenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hanna, Darrin M.; Oakley, Barbara A.; Stryker, Gabrielle A.; "Using a System-on-a-Chip Implantable Device to Filter Circulating Infected Cells in Blood or Lymph"; IEEE Transactions on Nanobioscience; bearing dates of Jan. 25, 2003, Mar. 2003; pp. 6-13; vol. 2, No. 1; IEEE.

Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24-28, 2000; pp. 1-8; vol. 2.

Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.

Kassim, Irwan; Phee, Louis; Ng, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.

Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.

Lu, Zhao; Martel, Sylvain; "Preliminary Investigation of Bio-carriers Using Magnetotactic Bacteria"; Proceedings of the 28$^{th}$ IEEE EMBS Annual International Conference; bearing dates of Aug. 30-Sep. 3, 2006 and 2006; pp. 3415-3418; IEEE.

Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; located at http://biorobots.cwru.edu/publications/ICRA02_Mangan_Endoscope.pdf.

Martel, Sylvain; "Fundamentals of high-speed piezo-actuated three-legged motion for miniature robots designed for nanometer-scale operations"; pp. 1-8.

Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28$^{th}$ IEEE EMBS Annual International Conference; bearing dates of Aug. 30-Sep. 3, 2006 and 2006; pp. 3399-3402; IEEE.

Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.

Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.

Meier, P.; Oberthür, S.; Lang, M.; "Development of a compliant device for minimally invasive surgery"; Proceedings of the 28th IEEE EMBS Annual International Conference; bearing dates of Aug. 30-Sep. 3, 2006 and 2006; pp. 331-334; IEEE.

"MEMS at the cutting edge®, Patent Pending"; Verimetra; pp. 1-2; located at http://www.verimetra.com/flow.htm; printed on May 4, 2006.

Menciassi, A.; Park, Jong H.; Lee, S.; Gorini, S.; Dario, P.; Park, Jong-Oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.

Mohseni, Kamran; "Biomimetic & Bio-Inspired Aerial and Underwater Vehicles"; bearing a date of Sep. 23, 2006; pp. 1-10; printed on Jan. 4, 2007; located at http://enstrophy.colorado.edu/~mohseni/MicroVehicles1.html#UUV1#UUV1.

Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.

Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; located at http://www.pharmscitech.com/.

Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"New Medical Device Combines Wireless and MEMS Technology"; Georgia Institute of Technology; pp. 1-4; PhysOrg.com; located at: http://www.physorg.com/printnews.php?newsid=10533; printed on Feb. 20, 2006.

Nieuwenhuizen-Berkovits, P.; "lubrelastic medical appliances"; Lubrelastic Medical Appliances; pp. 1-4; located at: http://www.xs4all.nl/~plien070/caeng.html; printed on Feb. 20, 2006.

Nyitrai, Zsolt; Illyefalvi-Vitéz, Zsolt; Pinkola, János; "Preparing Stents with Masking & Etching Technology"; 26th International Spring Seminar on Electronics Technology; bearing dates of May 8-11, 2003 and 2003; pp. 321-324; IEEE.

Patronik, N.A.; Ota, T.; Zenati, M.A.; Riviere, C.N.; "Improved Traction for a Mobile Robot Traveling on the Heart"; Proceedings of the 28th IEEE EMBS Annual International Conference; bearing dates of Aug. 30-Sep. 3, 2006 and 2006; pp. 339-342; IEEE.

"Remote-Control Electrostimulation Capsule"; Popular Science; bearing dates of 2002 and 2003; pp. 1-2; located at http://www.popsci.com/popsci/brown/2003/article/0,18881,537028,00.html; printed on May 4, 2006.

"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; located at http://www.underwatertimes.com/print.php?article_id=51030782641.

Rice, Mike; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725.

Rice, Mike; "New Products, Emphasis on Miniaturization Driving Medical Device Innovation"; bearing a date Aug. 23, 2006; pp. 1-3; Advantage Business Media; located at http://www.mdtmag.com/scripts/ShowPR.asp?PUBCODE=046&ACCT=0006109&ISSUE=0603&RELTYPE=PR&PRODCODE=0790&PRODLETT=A; printed on Aug. 23, 2006.

Saltzman, John R.; "Endoscopic Advances—A View Toward the Future"; bearing dates of May 4, 2006, May 17, 2005, and 2005; pp. 1-4; Medscape; located at http://www.medscape.com/viewarticle/505100; printed on May 4, 2006.

Schmidt, W.; Behrens, P.; Behrend, D.; Schmitz, K.-P.; Andresen, R.; "Experimental Study of Peripheral, Balloon-expandable Stent Systems"; Progress in Biomedical Research; pp. 246-255; bearing a date of May 2001.

Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; located at www.elsevier.com/locate/jconrel.

Serruys, Patrick W.; Kutryk, Michael J.B.; Ong, Andrew T.L.; "Coronary-Artery Stents"; The New England Journal of Medicine; bearing dates of Feb. 2, 2006 and Feb. 15, 2006; pp. 483-495; vol. 354;5; Massachusetts Medical Society.

Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.

Stoeckel, Dieter; Pelton, Alan; Duerig, Tom; "Self-expanding nitinol stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlag GmbH-SpringerLink—Article; located at: http://www.springerlink.com/(1begg455gtgjfseqqptyb43m)/app/home/contribution.asp?referrer=parent&backto=issue,17,26;journal,27,147;browsepublicationsresults,444,1551; printed on Feb. 22, 2006.

Strauss, Bradley H., M.D., Ph.D.; Li, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit Iliac Artery Model"; Int. J. Radiation Oncology Biol. Phys.; bearing dates of Oct. 23, 2001, May 13, 2002 and May 15, 2002 and 2002; pp. 551-561; vol. 54, No. 2; Elsevier Science Inc.

"Trying to control pain can be a double-edged sword, say scientists"; PhysOrg.com; printed on Nov. 2, 2006; pp. 1-2; located at http://www.physorg.com/printnews.php?newsid=81599312.

Tummala, R. Lal; Mukherjee, R; Aslam, D.; Xi, Ning; Mahadevan, S.; Weng, J.; "Reconfigurable Adaptable Micro-robot"; IEEE; bearing a date of 1999; pp. 687-691.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com/nature.

"Zyvex NanoEffector Microgrippers"; Nanotechnology at Zyvex; printed on Dec. 7, 2006; pp. 1-2; located at http://www.zyvex.com/Products/Grippers_Features.html.

"Zyvex NanoEffector Microgrippers"; Zyvex.com; bearing a date of 2006; pp. 1-2; Zyvex Corporation.

UK Intellectual Property Office Examination Report Under Section 18(3); App. No. GB0821524.6; Aug. 9, 2010; pp. 1-2.

UK Intellectual Property Office Examination Report Under Section 18(3); App. No. GB0821519.6; Aug. 9, 2010; pp. 1-3.

UK Intellectual Property Office Examination Report Under Section 18(3); App. No. GB0706802.6; bearing a date of Dec. 1, 2008; pp. 1-2.

U.S. Appl. No. 11/726,031, Ferren et al.
U.S. Appl. No. 11/726,025, Ferren et al.
U.S. Appl. No. 11/725,982, Ferren et al.
U.S. Appl. No. 11/645,358, Ferren et al.
U.S. Appl. No. 11/645,357, Ferren et al.

U.S. Appl. No. 11/541,492, Jung et al.
U.S. Appl. No. 11/541,452, Jung et al.
U.S. Appl. No. 11/541,448, Jung et al.
U.S. Appl. No. 11/541,378, Jung et al.
U.S. Appl. No. 11/541,377, Jung et al.
U.S. Appl. No. 11/526,203, Jung et al.
U.S. Appl. No. 11/526,201, Jung et al.
U.S. Appl. No. 11/526,144, Jung et al.
U.S. Appl. No. 11/526,089, Jung et al.
Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.
Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; located at: www.elsevier.com/locate/bios.
Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.
Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; located at: www.nature.com/naturematerials.
Cui, Xinyan; Hetke, Jamille F.; Wiler, James A.; Anderson, David J.; Martin, David C.; "Electrochemical Deposition and Characterization of Conducting Polymer Polypyrrole/PPS on Multichannel Neural Probes"; Sensors and Actuators A Physical; bearing a date of 2001; pp. 8-18; vol. 93; Elsevier Science B.V.; located at: www.elsevier.com/locate/sna.
Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telemetry System"; Annals of Otology Rhinology and Laryngology; bearing a date of May 2002; pp. 407-414; vol. 111, No. 5; Annals Publishing Company.
Donoghue, John P.; "Review: Connecting Cortex to Machines: Recent Advances in Brain Interfaces"; Nature Neuroscience Supplement; bearing a date on Nov. 2002; pp. 1085-1088; Vol. 5; Nature Publishing Group; located at: http://www.nature.com/natureneuroscience.
Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.
Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.
Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods, bearing a date of 1998; pp. 35-46; vol. 37; Elsevier Science B.V.
Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; located at: http://www.nature.com/natureprotocols.
Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.
Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.

Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.
Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.
Inmann, Andreas; Haugland, Morten; Haase, Jens; Biering-sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.
Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.
"Japanese Researchers Unveil Medical Mini Robot"; Yahoo! News; bearing a date of Mar. 8, 2007; pp. 1-2; Yahoo! Inc.; located at: http://news.yahoo.com/s/afp/20070308/hl_afp/afplifestyleshealthscience; printed on Mar. 8, 2007.
Ji, Jin; Najafi, Khalil, Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.
Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.
Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.
Loeb, Gerald E.; Peck, Raymond A.; Moore, William H.; Hood, Kevin; "BION System for Distributed Neural Prosthetic Interfaces"; Medical Engineering and Physics; bearing a date of 2001; pp. 9-18; vol. 23; Elsevier Science Ltd.; located at: www.elsevier.com/locate/medengphy.
Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.
Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.
Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal using a Conventional Clinical Magnetic Resonance Imaging System"; Applied Physics Letters; 2007; pp. 114105-1-114105-3; vol. 90, No. 114105; American Institute of Physics.
McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.
Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; located at: www.sciencemag.org; printed on Jan. 25, 2007.
Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2-4, 2002; pp. 237-240; IEEE.
Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.

Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.

Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.

Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.

Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.

Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.

Robinson, David A.; "The Electrical Properties of Metal Microelectrodes"; Proceedings of the IEEE; bearing a date of Jun. 1968; pp. 1065-1071; vol. 56, No. 6.

Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.

Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.

Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.

Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; located at: www.nature.com.

Snoek, GJ; Ijzerman, MJ; In 'T Groen, Facg; Stoffers, TS; Zilvold, G; "Use of the NESS Handmaster to Restore Handfunction in Tetraplegia: Clinical Experiences in Ten Patients"; Spinal Cord; bearing a date of 2000; pp. 244-249; vol. 38; International Medical Society of Paraplegia.

Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.

Taylor, Dawn M.; Helms Tillery, Stephen I.; Schwartz, Andrew B.; "Research Article: Direct Cortical Control of 3D Neuroprosthetic Devices"; Science; bearing a date of Jun. 7, 2002; pp. 1829-1832; vol. 296; located at: www.sciencemag.org.

"Tiny Robot Reduces Need for Surgery"; Pink Tentacle; bearing a date of Feb. 26, 2007; p. 1; located at: http://www.pinktentacle.com/2007/02/tiny-robot-reduces-need-for-surgery; printed on Mar. 8, 2007.

Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.

Warland, David K.; Reinagel, Pamela; Meister, Markus; "Decoding Visual Information from a Population of Retinal Ganglion Cells"; bearing a date of 1997; pp. 2336-2350; The American Physiological Society.

Weis, Rolf; Müller, Bernt; Fromherz, Peter; "Neuron Adhesion on a Silicon Chip Probed by an Array of Field-Effect Transitors"; Physical Review Letters; bearing a date of Jan. 8, 1996; pp. 327-330; vol. 76, No. 2; The American Physical Society.

Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; located at: www.nature.com.

White, Dave; "Mini Robot Explores, Gives you Medicine from Within"; Mobile Magazine; bearing a date of Feb. 27, 2007; p. 1; located at: http://www.mobilemag.com/content/100/313/C11869/; printed on Mar. 8, 2007.

UK Intellectual Property Office Examination Report Under Section 18(3); App. No. GB0821526.1; bearing a date of Jul. 15, 2010; pp. 1-2.

UK Intellectual Property Office Examination Report Under Section 18(3), App. No. GB0821523.8; Jul. 2, 2009; pp. 1-2.

U.S. Appl. No. 11/478,368, Ferren et al.
U.S. Appl. No. 11/403,230, Ferren et al.
U.S. Appl. No. 11/485,619, Hillis et al.
U.S. Appl. No. 11/417,898, Hillis et al.
U.S. Appl. No. 10/949,186, Hillis et al.
U.S. Appl. No. 12/075,480, Hillis et al.
U.S. Appl. No. 10/827,572, Wood, Jr.
U.S. Appl. No. 10/827,576, Wood, Jr.
U.S. Appl. No. 10/827,578, Wood, Jr.
U.S. Appl. No. 10/827,390, Wood, Jr.
U.S. Appl. No. 11/891,333, Wood, Jr.
U.S. Appl. No. 11/891,355, Wood, Jr.
U.S. Appl. No. 11/891,334, Wood, Jr.
U.S. Appl. No. 11/891,356, Wood, Jr.
U.S. Appl. No. 11/891,573, Wood, Jr.
U.S. Appl. No. 11/891,371, Wood, Jr.

"A Hydrogel-based CO2 sensor"; BIOS—The lab on a chip group; bearing a date of Aug. 29, 2005; pp. 1-2; located at: http://bios.ewi.utwente.nl/research/analysissystemssenors/ahydrogelbased.doc/index.html; printed on Apr. 25, 2006; University of Twente; the Netherlands.

Smith, Michael; "PAS: Nasal Spray Flu Vaccine Seems Safe and Effective in Young"; May 2, 2006; pp. 1-2; MedPage Today, LLC; bearing dates of 2004-2006; printed on May 4, 2006; located at http://www.medpagetoday.com/tbprint.cfm?tbid=3213.

UK Intellectual Property Office Examination Report Under Section 18(3); App. No. GB0706802.6; Nov. 23, 2009; pp. 1-2.

Japanese Office Action; Japanese App. No. 2007-533572; Sep. 22, 2010; pp. 1-4; (no English translation currently available).

UK Intellectual Property Office Examination Report Under Section 18(3); App. No. GB0821519.6; Oct. 19, 2010; 1 page.

UK Intellectual Property Office Examination Report under Section 18(3); App. No. GB0821521.2; Jan. 12, 2011; 4 pages.

U.S. Appl. No. 12/928,455, Wood, Jr., Lowell L.

UK Intellectual Property Office Combined Search and Examination Report Under Sections 17 & 18(3); App. No. GB1016383.0; Nov. 1, 2010; pp. 1-4.

UK Intellectual Property Office Examination Report Under Section 18(3); App. No. GB0821530.3; Aug. 27, 2010; pp. 1-6.

U.S. Appl. No. 12/930,916, Wood, Jr., Lowell.

* cited by examiner

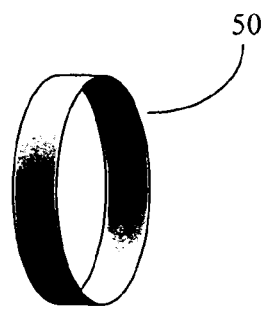
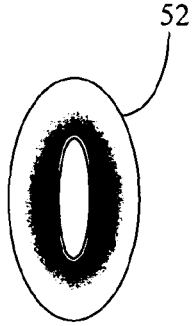
FIG. 2A  FIG. 2B
FIG. 2C
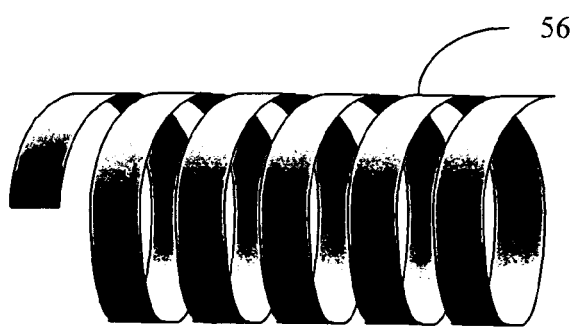
FIG. 2D

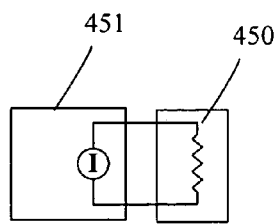
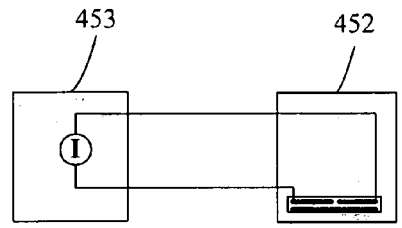
FIG. 7A
FIG. 7B
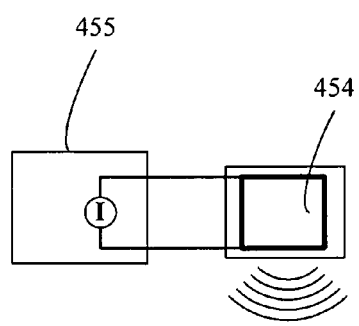
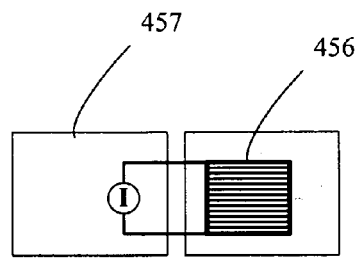
FIG. 7C
FIG. 7D

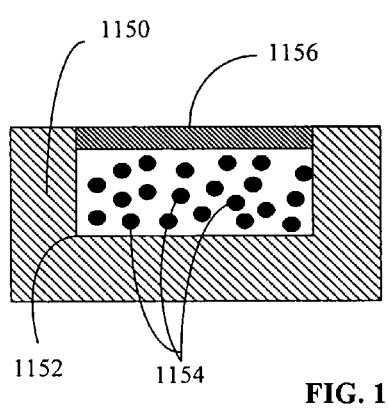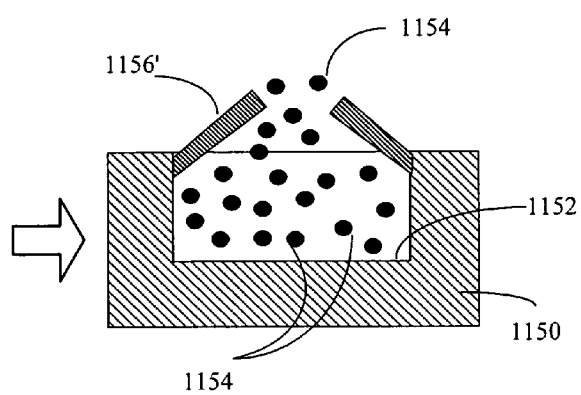
FIG. 19A   FIG. 19B
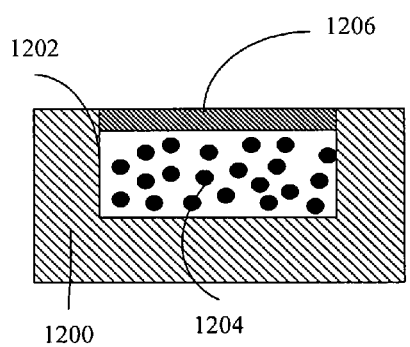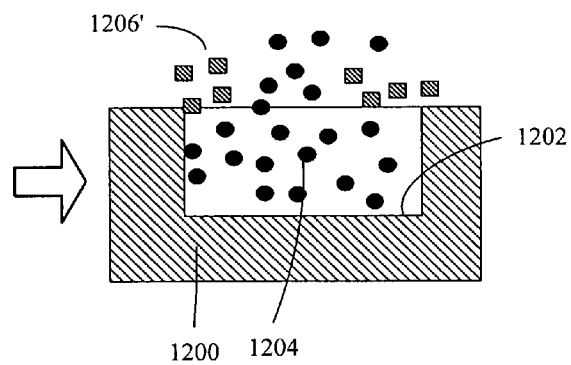
FIG. 20A   FIG. 20B
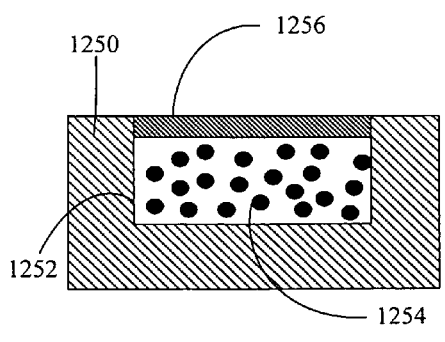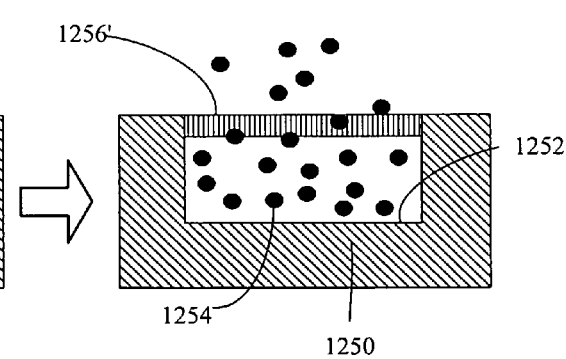
FIG. 21A   FIG. 21B

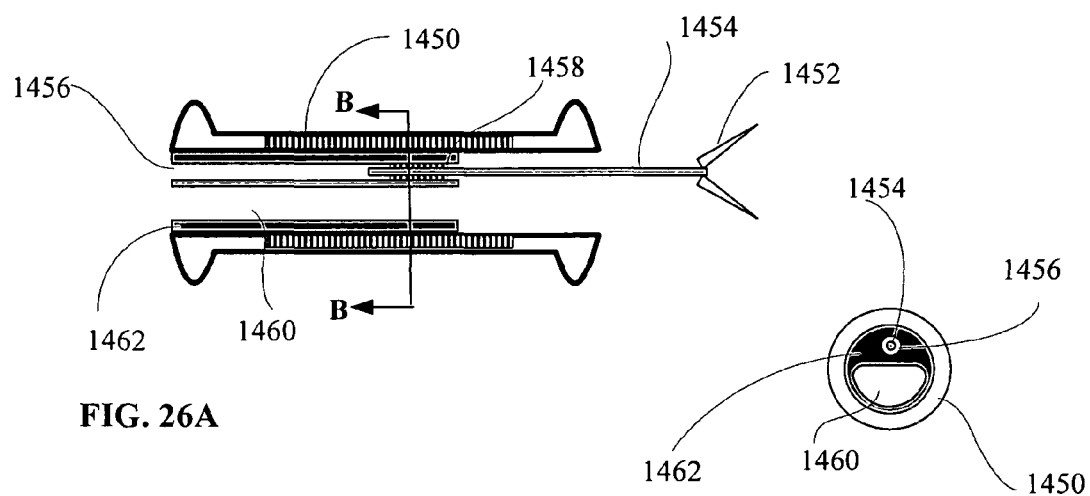
FIG. 26A
FIG. 26B
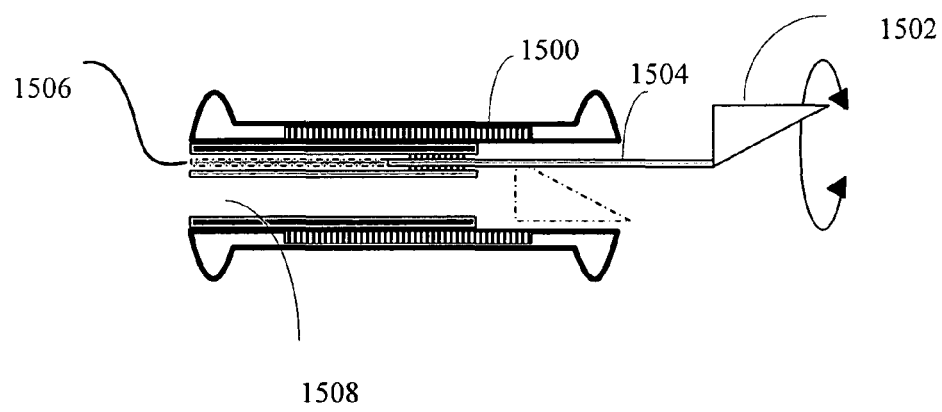
FIG. 27

2260 performing an action with an active portion of the lumen-traveling device in response to the response initiation signal wherein performing an action with the active portion includes collecting a material from the body lumen 2270 wherein performing an action with the active portion includes collecting a sample from a fluid within the body lumen 2272 wherein performing an action with the active portion includes collecting a sample from a wall region of the body lumen 2274 wherein performing an action with the active portion includes producing heating. 2276 including propelling the lumen-traveling device through the body lumen to a location in the vicinity of the preoptic area, wherein performing an action with the active portion includes producing heating in the vicinity of the preoptic area. 2278 heating in male reproductive system to destroy gametes 2280 wherein performing an action with the active portion includes producing cooling. 2282 wherein performing an action with the active portion includes securing the lumen-traveling device into position within the body lumen. 2284

FIG. 40B

LUMEN-TRAVELING DELIVERY DEVICE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 10/949,186, entitled A CILIATED STENT-LIKE SYSTEM, naming Richa Wilson, Victoria Y. H. Wood, W. Daniel Hillis, Clarence T. Tegreene, Muriel Y. Ishikawa, and Lowell L. Wood, Jr. as inventors, filed 24 Sep. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 10/827,576, entitled A SYSTEM FOR PERFUSION MANAGEMENT, naming Lowell L. Wood, Jr. as inventor, filed 19 Apr. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 10/827,578, entitled A SYSTEM WITH A SENSOR FOR PERFUSION MANAGEMENT, naming Lowell L. Wood, Jr. as inventor, filed 19 Apr. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 10/827,572, entitled A SYSTEM WITH A RESERVOIR FOR PERFUSION MANAGEMENT, naming Lowell L. Wood, Jr. as inventor, filed 19 Apr. 2004 now U.S. Pat. No. 7,850,676, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 10/827,390, entitled A TELESCOPING PERFUSION MANAGEMENT SYSTEM, naming Lowell L. Wood, Jr. as inventor, filed 19 Apr. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/403,230, entitled LUMENALLY-ACTIVE DEVICE, naming Bran Ferren, W. Daniel Hillis, Roderick A. Hyde, Muriel Y. Ishikawa, Edward K. Y. Jung, Nathan P. Myhrvold, Elizabeth A. Sweeney, Clarence T. Tegreene, Richa Wilson, Lowell L. Wood, Jr. and Victoria Y. H. Wood as inventors, filed 12 Apr. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/417,898, entitled CONTROLLABLE RELEASE NASAL SYSTEM, naming W. Daniel Hillis, Roderick A. Hyde, Muriel Y. Ishikawa, Elizabeth A. Sweeney, Clarence T. Tegreene, Richa Wilson, Lowell L. Wood, Jr. and Victoria Y. H. Wood as inventors, filed 4 May 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,368, entitled LUMENALLY-ACTIVE DEVICE, naming Bran Ferren, W. Daniel Hillis, Roderick A. Hyde, Muriel Y. Ishikawa, Edward K. Y. Jung, Nathan P. Myhrvold, Elizabeth A. Sweeney, Clarence T. Tegreene, Richa Wilson, Lowell L. Wood, Jr. and Victoria Y. H. Wood, as inventors, filed 28 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/485,619, entitled CONTROLLABLE RELEASE NASAL SYSTEM, naming W. Daniel Hillis, Roderick A. Hyde, Muriel Y. Ishikawa, Elizabeth A. Sweeney, Clarence T. Tegreene, Richa Wilson, Lowell L. Wood, Jr. and Victoria Y. H. Wood as inventors, filed 11 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/645,357, entitled LUMEN-TRAVELING DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Elizabeth A. Sweeney, Clarence T. Tegreene, Lowell L. Wood, Jr. and Victoria Y. H. Wood as inventors, filed 21 Dec. 2006 now U.S. Pat. No. 7,857,767, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/645,358, entitled LUMEN-TRAVELING DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Elizabeth A. Sweeney, Clarence T. Tegreene, Lowell L. Wood, Jr. and Victoria Y. H. Wood as inventors, filed 21 Dec. 2006, which is currently co-pending, or is an application of which a currently co-pending application is entitled to the benefit of the filing date.

The U.S. Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Devices and systems have been developed for use in various body lumens, particularly in the cardiovascular system, digestive tract, and urogenital tract. Catheters are used for performing a variety of sensing, material delivery or surgical tasks. Stents are implanted in blood vessels for the purpose of preventing stenosis or restenosis of blood vessels. Capsules containing sensing and imaging instrumentation that may be swallowed by a subject and which travel passively through the digestive tract have also been developed. Robotic devices intended to move through the lower portion of the digestive tract under their own power are also under development.

SUMMARY

The present application describes devices, systems, and related methods for performing delivering a material with a lumen-traveling device.

In one aspect, a lumen-traveling delivery device may include a propelling mechanism; a material release portion; and control circuitry located at least in part on the delivery device, the control circuitry capable of controlling the operation of the propelling mechanism to move the delivery device through the body lumen to a treatment target and controlling the material release portion to release the deliverable material when the delivery device may be in the vicinity of the treatment target.

In another aspect, a lumen-traveling delivery device may include a structural element sized to fit within a body lumen in the vicinity of a treatment target; at least two wall-engaging structures operable to alternately engage and disengage a wall of the body lumen; a propelling mechanism capable of producing relative extension and retraction of the at least two wall-engaging structures with respect to each other in combination with alternate engagement and disengagement of the body lumen wall to produce movement of the lumen-traveling delivery device with respect to the body lumen wall; and a material release portion configured to release a deliverable material when the lumen-traveling delivery device may be located in the vicinity of the treatment target.

In another aspect, a method of delivering a material to a subject may include the steps of moving a self-propelling delivery device through a body lumen toward a target site; detecting the arrival of the delivery device in the vicinity of a target site; stopping movement of the delivery device; blocking the flow of fluid through the body lumen by extending or expanding a portion of the delivery device; and releasing a material into the body lumen from a portion of the delivery device.

In addition to the foregoing, other device and system aspects are described in the claims, drawings, and text forming a part of the present disclosure.

In addition to the foregoing, other method aspects are described in the claims, drawings, and text forming a part of the present disclosure.

Various aspects of the operation of such lumen-traveling devices may be performed under the control of hardware, software, firmware, or a combination thereof. In one or more aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 2A-2D are illustrations of several embodiments of lumen-traveling device structural elements;

FIGS. 7A-7D are illustrations of several embodiments of lumen-traveling device active portions;

FIGS. 19A and 19B are depictions of the release of a stored deliverable material from a reservoir via a rupturable barrier;

FIGS. 20A and 20B are depictions of the release of a stored deliverable material from a reservoir via a degradable barrier;

FIGS. 21A and 21B are depictions of the release of a stored deliverable material from a reservoir via a barrier having controllable permeability;

FIG. 26A is an illustration of a lumen-traveling device including a cutting tool;

FIG. 26B is a cross-sectional view of the lumen-traveling device of FIG. 26A;

FIG. 27 is an illustration of a lumen-traveling device including a scraping tool;

FIGS. 40A-40F form a flow diagram showing further variants of a method implemented with a lumen-traveling device;

DETAILED DESCRIPTION

Figure 1:
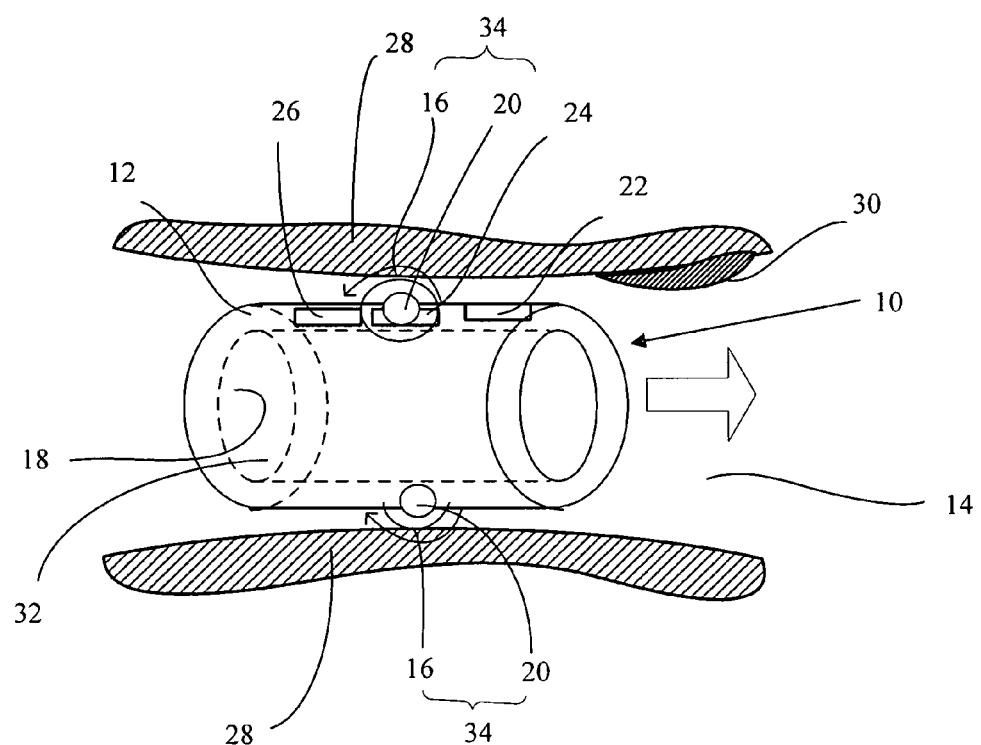
FIG. 1 is an illustration of an embodiment of a lumen-traveling device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A lumen-traveling device is an example of a lumenally active device. Lumenally active devices, and related methods and systems, are described in U.S. patent application Ser. No. 11/403,230, entitled "Lumenally Active Device," filed Apr. 12, 2006, which is incorporated herein by reference. U.S. patent application Ser. No. 11/403,230 describes a lumenally-active system that may include a structural element configured to fit within at least a portion of a body lumen, the structural element including a lumen-wall-engaging portion and a fluid-contacting portion configured to contact fluid within the body lumen; a sensor capable of detecting a condition of interest in the fluid; response initiation circuitry operatively connected to the sensor and configured to generate a response initiation signal upon detection of the condition of interest in the fluid by the sensor; and an active portion operatively connected to the response initiation circuitry and capable of producing a response upon receipt of the response initiation signal.

As illustrated in FIG. 1, an embodiment of a lumen-traveling device 10 may include a structural element 12 configured to fit within at least a portion of a body lumen 14. The structural element 12 may include a lumen-wall-engaging portion 16 and a fluid-contacting portion 18 configured to contact fluid within the body lumen. Lumen-traveling device 10 may also include a propelling mechanism 20 capable of producing movement of the structural element 12 through a body lumen 14 in which the structural element is deployed, a sensor 22 capable of detecting a condition of interest in the body lumen, response initiation circuitry 24 operatively connected to the sensor 22 and configured to generate a response initiation signal upon detection of a condition of interest in the body lumen (e.g., plaque 30); and an active portion 26 operatively connected to the response initiation circuitry and capable of producing a response upon receipt of the response initiation signal. Body lumen 14 is defined by wall portions 28, which may be the walls of a blood vessel or other lumen-containing structure within the body of an organism. In this example, a body fluid flows through lumen 14 in the direction indicated by the arrow. Fluid flows through the central opening 32 of structural element 12, with the interior surface of structural element 12 forming fluid-contacting portion 18. In the embodiment of FIG. 1, sensor 22 and active portion 26 may be located at a fluid-contacting portion 18. Lumen-wall-engaging portions 16 may be, for example, rotating wheels, which function to frictionally engage wall portions 28, and which may also, in combination with a rotary motor 20, function as a propelling mechanism 34 to move lumen-traveling device 10 through body lumen 14. In other embodiments of lumenally traveling devices, other structures and methods for engaging the lumen wall and/or propelling the device through the lumen may be employed.

Embodiments of a lumen-traveling device or system may be configured for use in (e.g., configured to fit within) body lumens of an organism including, for example, the respiratory tract, the cardiovascular system (e.g., a blood vessel), a portion of a CSF-space (cerebro-spinal fluid space) of the nervous system (e.g., the spinal canal, the ventricles of the brain, the sub-arachnoid space, etc.), a portion of the urinary tract (for example a ureter), a portion of the lymphatic system, a portion of the abdominal cavity, a portion of the thoracic cavity, a portion of the digestive tract, a portion of a reproductive tract, either the female reproductive tract (e.g., a lumen of a fallopian tube) or the male reproductive tract (including various lumens including but not limited to the epididymis, vas deferens or ductul deferens, efferent duct, ampulla, seminal duct, ejaculatory duct, or urethra), the biliary tract, a nostril or nasal cavity, the oral cavity, the digestive tract, the tear ducts, or a glandular system. Other body lumens may be found in the auditory or visual system, or in interconnections thereof, e.g., the Eustachian tubes. Some of the devices and systems described herein may be used in body lumens through which fluid flows, but it is not intended that such devices or systems are limited to use in tubular lumen-containing structures containing moving fluid; in some applications a lumen-traveling device may be used in a body lumen containing relatively unmoving, or intermittently moving fluid.

Also included within the scope of the term "body lumen" are man-made lumens within the body, including vascular catheters, spinal fluid shunts, vascular grafts, bowel re-anastomoses, bypass grafts, indwelling stents of various types (e.g., vascular, gastrointestinal, tracheal, respiratory, ureteral, genitourinary, etc.) and surgically created fistulas.

The term fluid, as used herein, may refer to liquids, gases, and other compositions, mixtures, or materials exhibiting fluid behavior. The fluid within a body lumen may include a liquid, or a gas or gaseous mixtures. As used herein, the term fluid may encompass liquids, gases, or mixtures thereof that also include solid particles in a fluid carrier. Liquids may include mixtures of two or more different liquids, solutions, slurries, or suspensions. Body fluids may include components such as, for example, cells, cellular fractions or components, collections or aggregations of cells, bacterial, viral or fungal species, ions, molecules, gas bubbles, dissolved gas, suspended particles, or a variety of other materials that may be present in the body fluid. Body fluid components may be materials that are normally present in the body fluid, materials that are naturally derived but not normally present in the body fluid, or foreign materials that have entered or been introduced to the body fluid (including but not limited to pathogens, toxins, pollutants, or medications, for example). Examples of liquids present within body lumens include blood, lymph, serum, urine, semen, digestive fluids, tears, saliva, mucous, cerebro-spinal fluid, intestinal contents, bile, epithelial exudate, or esophageal contents. Liquids present within body lumens may include synthetic or introduced liquids, such as blood substitutes, or drug, nutrient, or saline solutions. Fluids may include liquids containing dissolved gases or gas bubbles, or gases containing fine liquid droplets or solid particles. Gases or gaseous mixtures found within body lumens may include inhaled and exhaled air, e.g. in the nasal or respiratory tract, or intestinal gases.

A lumen-traveling device may be configured to fit within a particular lumen through appropriate selection of device dimensions, material properties, and propelling mechanism. Configuration aspects may include size, shape, rigidity/flexibility, porosity, and biocompatibility, among others, which may depend on both the materials and construction of the device. Dimensions of a lumen-traveling device may be selected so that the device will be small enough to fit within the smallest expected dimension of the lumen of interest. A material that is both biocompatible and sufficiently durable for use in the lumen of choice may be selected based on standards well known to those of skill in the art. Wherever a lumen-traveling device or system is to be used, the dimensions and mechanical properties (e.g., rigidity) of the lumen-traveling system, and particularly of the structural element of the lumen-traveling system, may be selected for compatibility with the location of use, in order to provide for reliable positioning of the device and to prevent damage to the lumen-containing structure including the body lumen. The propelling mechanism may be selected for the type and nature of the lumen to be traveled. A lumen having a relatively uniform cross-section (height and/or width) over the length to be traveled may be traversed by most propelling mechanisms. A lumen that varies significantly in cross-section over the length to be traveled may pose a challenge for some propelling mechanisms that engage the lumen wall on all sides, but a lumen-traveling device that walks or rolls along one side of a lumen, or employs more than one mode of propulsion, may adapt well to changes in lumen cross-section. A lumen-traveling device that is capable of altering its dimensions (e.g. changing in length and diameter) may also be of utility in some applications. For example, see U.S. Patent Application 2005/0177223, which is incorporated herein by reference in its entirety. However, in many cases it may be possible to design a lumen-traveling device of fixed dimension suited for a particular application, or provide a set of lumen-traveling devices in several sizes, from which the best size can be selected for a particular application or particular patient, to variability in lumen dimensions between individual patients. The lumen-traveling device may include a structural element carrying at least one of the propelling mechanism, motion control circuitry, sensor, response initiation circuitry and active portion. Various materials may be used in the construction of the structural element. For example, the structural element may include a self-expanding material, a resilient material, or a mesh-like material. Flexibility may also be conferred by configuration as well as material: for example, the structural element may include a slotted structure. The structural element may include a biocompatible material, as noted above, and may include a bioactive component (such as a drug-releasing coating or bioactive material attached to or incorporated into the structural element).

FIGS. 2A-2D depict a number of possible configurations for structural elements of lumen-traveling devices for use in body lumens. In some embodiments, the structural element may be a substantially tubular structure. The structural element may include one or multiple lumens in fluid communication with the body lumen. In some embodiments, the structural element may have an adjustable diameter. Structural elements may have the form of a short cylinder 50, as shown in FIG. 2A; an annulus 52, as shown in FIG. 2B; a cylinder 54, as shown in FIG. 2C; or a spiral 56, as shown in FIG. 2D. A spiral structure is disclosed, for example, in Bezrouk et al, "Temperature Characteristics of Nitinol Spiral Stents"; Scripta Medica (BRNO); bearing dates of August 2005, October 2005; pp. 219-226; Vol. 78, No. 4, which is incorporated herein by reference in its entirety. Elongated forms such as cylinder 54 or spiral 56 may be suitable for use in tubular lumen-containing structures such as, for example, blood vessels.

Structural elements may be formed from various materials, including metals, polymers, fabrics, and various composite materials, including ones of either inorganic or organic character, the latter including materials of both biologic and a biologic origin, selected to provide suitable biocompatibility and mechanical properties. In these, and other examples of structural elements, it is contemplated that additional components, such as sensors, circuitry, and propelling mechanisms, for example, will be attached or connected to, manufactured on, or formed integrally with the structural element, but such additional components are not illustrated in these figures.

In some embodiments, the structural element may include a self-expanding material, or a resilient material. In some embodiments, the form as well as the material of the structural element may contribute to the expanding or flexing properties of the structural element. For example, the structural element may be formed from or include a mesh-like material or a slotted structure.

Figure 3A:
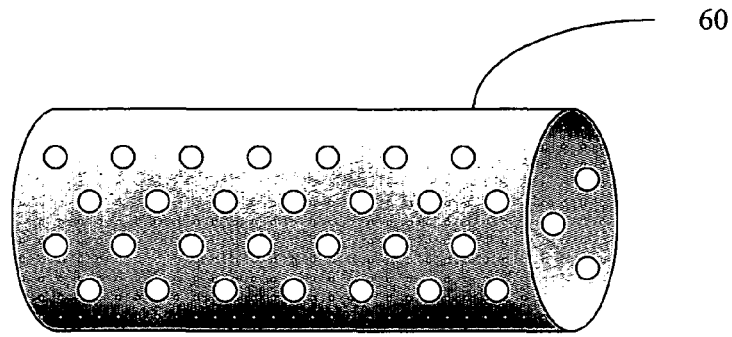
FIGS. 3A-3C are illustrations of several embodiments of lumen-traveling device structural elements.
Figure 3B:
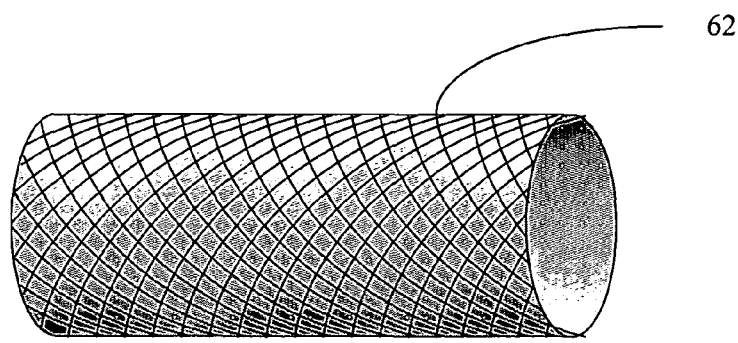
Figure 3C:
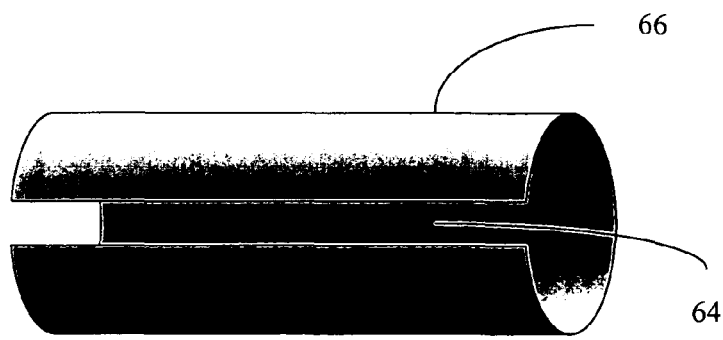
Figures 4A, 4B:
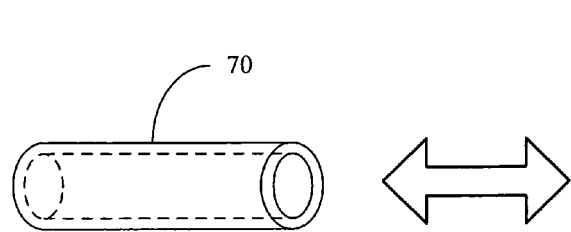
FIGS. 4A and 4B are illustrations of a device structure having a variable length and diameter.

As shown in FIGS. 3A-3C, the basic form of a structural element may be subject to different variations, e.g., by perforations, as shown in structural element 60 in FIG. 3A; a mesh structure, as shown in structural element 62 in FIG. 3B; or the inclusion of one or more slots 64 in structural element 66 in FIG. 3C. Slot 64 runs along the entire length of structural element 66; in other embodiments, one or more slots (or mesh or perforations) may be present in only a portion of the structural element. By using spiral, mesh, or slotted structural elements (as in FIGS. 2D, 3B, and 3C) formed from resilient material, elastic, springy or self-expanding/self-contracting structural elements may be formed. A self-expanding or self-contracting structural element may facilitate positioning of the structural element within a body lumen of an organism. In some embodiments, flexible material having adjustable diameter, taper, and length properties may be used. For example, some materials may change from a longer, narrower configuration 70 as shown in FIG. 4A, to a shorter, wider configuration 72 as shown in FIG. 4B, or may taper over their length. Structural elements that may exhibit this type of expansion/contraction property may include mesh structures formed of various metals or plastics, and some polymeric materials, for example. Examples of possible shape change materials are described in "Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html;

"Agile new plastics change shape with heat"; MIT Tech Talk; Nov. 22, 2006; p. 5 (1 page); and SHAHINPOOR, MOHSEN; KIM, KWANG J. ("Ionic polymer-metal composites: IV. Industrial and medical applications; Smart Materials and Structures; 2005; pp. 197-214; Vol. 14; Institute of Physics Publishing), all of which are incorporated herein by reference in their entirety.

Figure 5A:
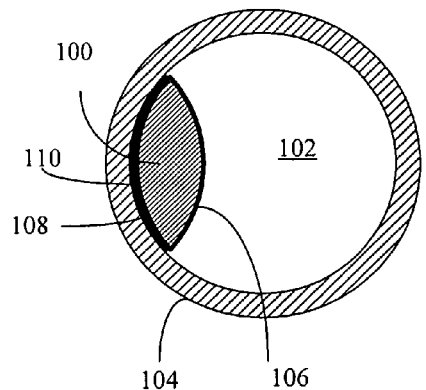
FIGS. 5A-5F are cross-sectional views of a number of embodiments of lumen-traveling device structures.

The exemplary embodiments depicted in FIGS. 2A-2C, 3A-3C, and 4A and 4B are substantially cylindrical, and hollow and tubular in configuration, with a single central opening. Thus, the exterior of the cylindrical structural element may contact and engage the wall of the body lumen, and the interior of the structural element (within the single central opening) may form a fluid-contacting portion of the structural element. Lumen-traveling devices according to various embodiments are not limited to cylindrical structural elements having a single central opening, however. Alternatively, a structural element may be configured to contact and move along a portion of a wall of a body lumen, contacting or engaging the lumen wall over a portion of its cross-section (as opposed to contacting the lumen wall along its entire cross-section) without obstructing the movement of fluid within the body lumen. Such an embodiment may be approximately hemi-spherical or hemi-elliptoid, with a cross-section as depicted in FIG. 5A. Other embodiments may be pill- or capsule-shaped, adapted to move through a central portion of a body lumen.

FIGS. 5A through 5F depict a variety of cross-sectional configurations for structural elements of lumen-traveling devices. In FIG. 5A, a lumen-traveling device 100 is positioned in lumen 102 of lumen-containing structure 104. In this embodiment, fluid-contacting portion 106 may be the surface of structural element 100 that faces lumen 102, while the lumen-wall-engaging portion 108 may include a layer of tissue adhesive on surface 110 of structural element 100. Tissue adhesives may be released from the lumen-traveling device when it has reached its destination. Lumen-traveling device 100 may be approximately hemi-spherical or hemi-ovoid. Lumen-wall-engaging portion 108 may have a curvature that corresponds approximately to the curvature of the lumen.

Figure 5B:
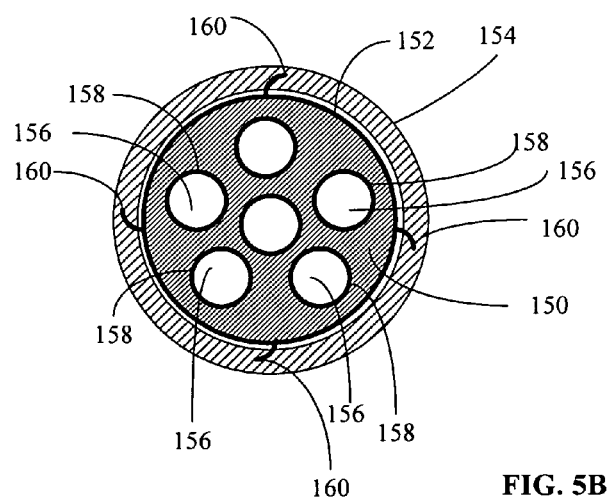

FIG. 5B depicts in cross-section a further embodiment of a structural element 150 in lumen 152 of lumen-containing structure 154. Structural element 150 includes multiple openings 156, each of which includes an interior surface 158 that forms a fluid-contacting portion. Structural element 150 may include one or more hook or claw-like structures 160 that serve as lumen-wall-engaging portions that maintain structural element 150 in position with respect to lumen-containing structure 154.

Figure 5C:
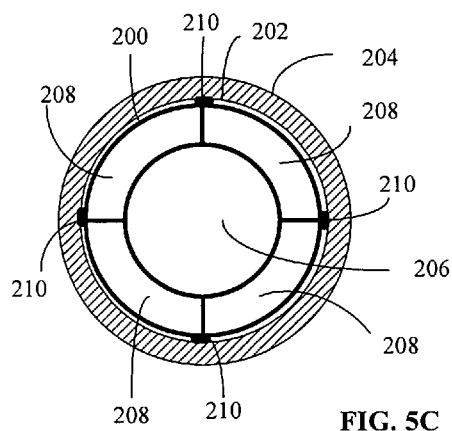

FIG. 5C depicts in cross-section an embodiment of a structural element 200 in lumen 202 of lumen-containing structure 204. Structural element 200 includes a large central opening 206 and multiple surrounding openings 208. The interior surface of each opening 206 or 208 serves as a fluid-contacting portion, while projections 210 function as lumen-wall-engaging portions, which may engage frictionally or may project slightly into the interior of the wall of lumen-containing structure 204.

Figure 5D:
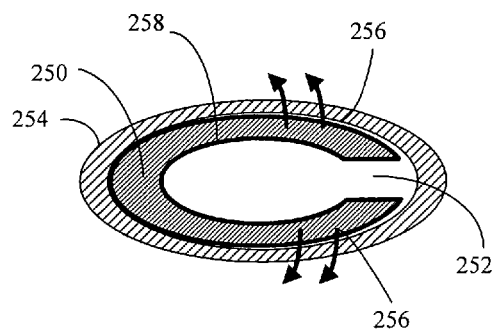

FIG. 5D depicts a further embodiment in which structural element 250 has a substantially oval cross-section and includes a slot 252. Lumen-containing structure 254 may be generally oval in cross section, or may be flexible enough to be deformed to the shape of structural element 250. Structural element 250 may be a compressed spring-like structure that produces outward forces as indicated by the black arrows, so that end portions 256 of structural element 250 thus press against and engage the lumen wall. Interior surface 258 of structural element 250 serves as the fluid-contacting portion of structural element 250.

Figure 5E:
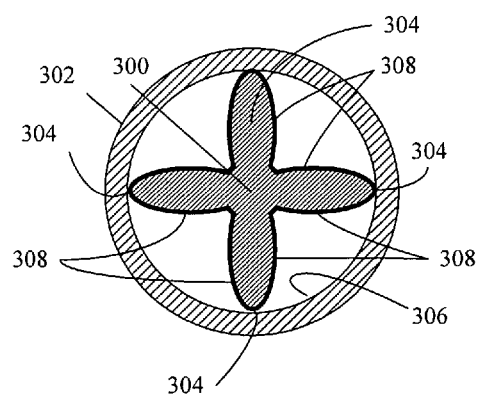

FIG. 5E is a cross-sectional view of a structural element 300 in a lumen-containing structure 302. Structural element 300 includes multiple projecting arms 304 which contact lumen wall 306 of lumen-containing structure 302, and function as lumen-wall-engaging portions. Inner surfaces 308 of arms 304 function as fluid-contacting portions of structural element 300.

Figure 5F:
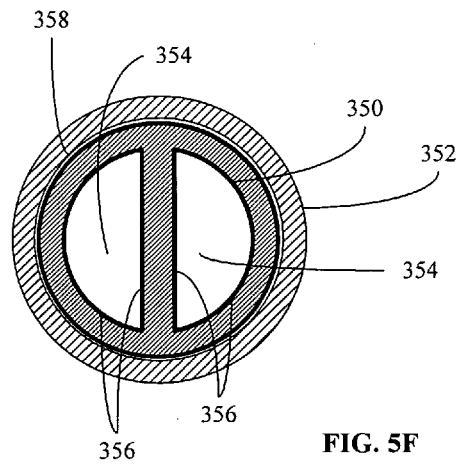

FIG. 5F depicts (in cross-section) another example of a structural element 350 positioned within a lumen-containing structure 352. Structural element 350 includes two openings 354. The interior surfaces 356 of openings 354 function as fluid-contacting portions, while the outer surface 358 of structural element 350 serves as a lumen-wall-engaging portion.

The structural elements depicted in FIGS. 1-5 are intended to serve as examples, and are in no way limiting. The choice of structural element size and configuration appropriate for a particular body lumen may be selected by a person of skill in the art. Structural elements may be constructed by a variety of manufacturing methods, from a variety of materials. Appropriate materials may include metals, ceramics, polymers, and composite materials having suitable biocompatibility, sterilizability, mechanical, and physical properties, as will be known to those of skill in the art. Examples of materials and selection criteria are described, for example, in *The Biomedical Engineering Handbook*, Second Edition, Volume I, J. D. Bronzino, Ed., Copyright 2000, CRC Press LLC, pp. IV-1—43-31. Manufacturing techniques may include injection molding, extrusion, die-cutting, rapid-prototyping, self-assembly, etc., and will depend on the choice of material and device size and configuration. Sensing portions, active portions, and propelling mechanisms or structures of the lumen-traveling device as well as associated circuitry (not depicted in FIGS. 2-5) may be fabricated on the structural element using various microfabrication and/or MEMS techniques, or may be constructed separately and subsequently assembled to the structural element, as one or more distinct components. Examples of microfabrication techniques include, for example, those disclosed in U.S. Patent Applications 2005/0221529, 2005/0121411, 2005/0126916, and NYITRAI, ZSOLT; ILLYEFALVI-VITÉZ, ZSOLT; PINKOLA, JÁNOS; "Preparing Stents with Masking & Etching Technology"; 26th International Spring Seminar on Electronics Technology; bearing dates of May 8, 2003-May 11, 2003 and 2003; pp. 321-324; IEEE, all of which are incorporated by reference in their entirety.

Figure 6:
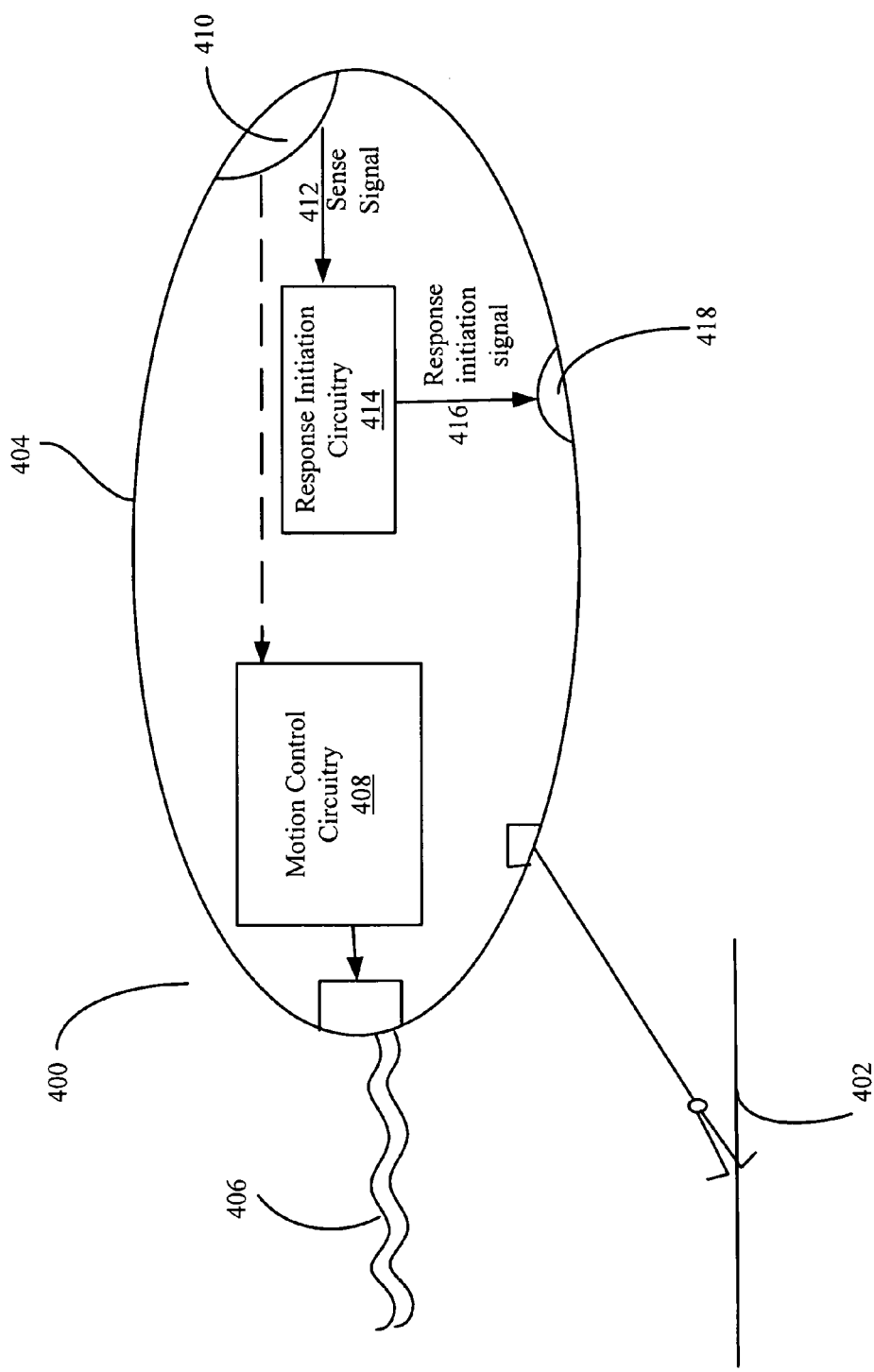
FIG. 6 illustrates an embodiment of a lumen-traveling device including a motion-arresting portion.

According to an embodiment as shown in FIG. 6, a lumen-traveling device 400 may include a motion-arresting portion 402; a fluid-contacting portion 404 configured to contact fluid within a body lumen and to at least intermittently permit flow of fluid through the body lumen; a propelling mechanism 406 capable of producing movement of the lumen-traveling device through a body lumen in which the lumen-traveling device is deployed; motion control circuitry 408 carried at least in part by said lumen-traveling device and configured to control the propelling mechanism 406 to control movement of the lumen-traveling device 400 through the body lumen; a sensor 410 capable of detecting a condition of interest in the body lumen and generating a sense signal 412 indicating detection of the condition of interest; response initiation circuitry 414 operatively connected to the sensor and configured to generate a response initiation signal 416 upon receipt of the sense signal indicating detection of a condition of interest in the body lumen; and an active portion 418 operatively connected to the response initiation circuitry and capable of producing a response upon receipt of the response initiation signal. In some embodiments, the condition of interest may be a local condition of interest (e.g. a condition related to the presence of injured or diseased tissue, an anatomical feature, etc.).

The motion control circuitry may be operatively connected to the sensor and configured to control the propelling mechanism at least in part in response to receipt of the sense signal indicating detection of the condition of interest in the body lumen.

The motion-arresting portion may take various forms, including, for example, an anchor capable of attaching at least temporarily to a wall of the lumen, as shown in FIG. 6; at least one hook or claw, e.g. as depicted in FIG. 5B; at least one adhesive material or glue, as shown in FIG. 5A; a brake to oppose the action of the propelling mechanism, or a shutoff for the propelling mechanism. In some embodiments, the motion-arresting portion may include a reversal mechanism for the propelling mechanism, in that to arrest motion it may be necessary to provide sufficient propulsion in the reverse direction to oppose a flow of fluid through the body lumen. The motion-arresting portion may be a part of, or associated with, the propelling mechanism (e.g. a shutoff for the propelling mechanism) or it may be a separate mechanism (adhesive, hook- or claw-like structure, anchor, etc.).

The lumen-traveling device may include an active portion capable of producing a response upon receipt of the response initiation signal. A lumen-traveling device may include a single active portion or multiple active portions, which may be of the same or different types. Active portions may perform related or complementary functions. A number of different types of active portion may be used in embodiments of the lumen-traveling device; a lumen-traveling device may include one or more active portions, and each active portion may perform one or more actions.

FIGS. 7-27 provide examples of different active portions which may be included in a lumen-traveling device. Some active portions may be most suitable for use in a lumen-traveling device while it is moving, and some active portions may be most suitable for use by a lumen-traveling device that is at rest within a body lumen. Many of the examples of active portions described herein may be adapted for use under either circumstance.

The active portion may include a heating element 450 as depicted in FIG. 7A, operatively coupled to the response initiation circuitry 451 and configured to produce heating in response to receipt of the response initiation signal. The heating element may be a resistive element that produces heat when current is passed through it, or it may be a magnetically active material that produces heat upon exposure to an electromagnetic field. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials; examples of electrically active materials include ferroelectrics, piezoelectrics and dielectrics. In some embodiments, heat may be generated through an exothermic chemical reaction. U.S. Patent Applications 2002/0147480 and 2005/0149170, provide examples of heating and/or cooling mechanisms and structures, and are incorporated herein by reference.

Alternatively, the active portion may include a cooling element 452 as depicted in FIG. 7B, operatively coupled to the response initiation circuitry 453 and configured to produce cooling in response to receipt of the response initiation signal. Cooling may be produced by a number of mechanisms and/or structures. For example, cooling may be produced by an endothermic reaction (such as the mixing of ammonium nitrate and water) initiated by opening of a valve or actuation of a container in response to a control signal. Other methods and/or mechanisms of producing cooling may include, but are not limited to, thermoelectric (Peltier Effect) and liquid-gas-vaporization (Joule-Thomson) devices.

In some embodiments, the active portion may include an electromagnetic radiation source 454 as depicted in FIG. 7C, operatively coupled to the response initiation circuitry 455 and configured to emit electromagnetic radiation in response to receipt of the response initiation signal. Electromagnetic radiation sources may include light sources, for example, such as light emitting diodes and laser diodes, or sources of other frequencies of electromagnetic energy or radiation, radio waves, microwaves, ultraviolet rays, infra-red rays, optical rays, terahertz beams, and the like.

The active portion may include an acoustic energy source 456 (e.g. a piezoelectric element) as depicted in FIG. 7D, operatively coupled to the response initiation circuitry 457 and configured to emit acoustic energy in response to receipt of the response initiation signal. An acoustic energy source may generate pressure pulses of various frequencies, including auditory frequencies, subsonic frequencies, and ultrasonic frequencies. A microscale acoustic transducer may be constructed, for example, in U.S. Pat. No. 5,569,968, which is incorporated herein by reference.

Figure 8A:
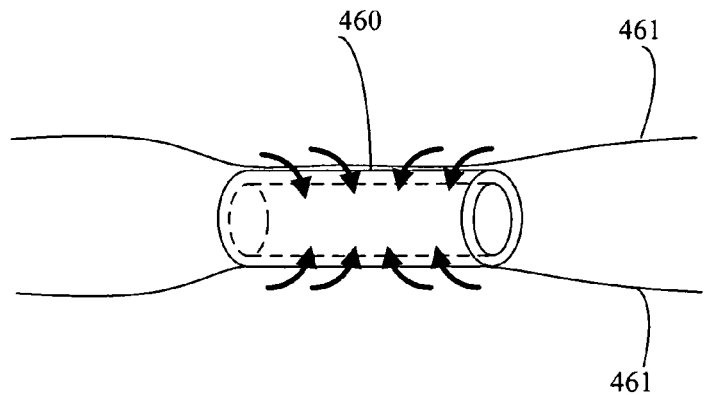
FIGS. 8A and 8B are illustrations of several further embodiments of lumen-traveling device active portions.
Figure 8B:
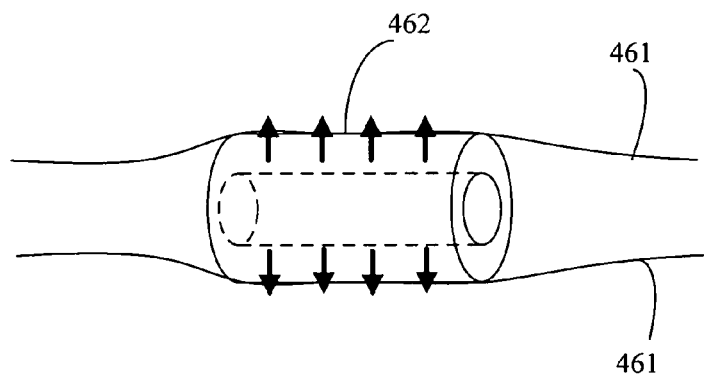

The active portion may include a pressure source operatively coupled to the response initiation circuitry and configured to apply pressure to the body lumen in response to receipt of the response initiation signal. Applied pressure may be positive pressure (e.g., to form a pressure fit of the device with the lumen wall, as described above, or to apply pressure to a particular location, e.g. to stop bleeding) or negative pressure (e.g., a vacuum, to adhere a portion of the lumen wall to the lumen-traveling device, for example to seal off a leak or aneurysm, or to position the device, as described previously). Pressure applied to a body lumen may influence one or both of the lumen walls or the contents of the lumen; in some cases application of pressure to a body lumen may increase (or decrease) the pressure in a fluid (gas or liquid) within the body lumen. A pressure source may include materials that expand through absorption of water or other materials, expand or contract due to generation or consumption of gas, or change conformation by chemical reactions or temperature changes, electrically-engendered Maxwell stresses, osmotic stress-generators, etc. FIG. 8A depicts a negative pressure source 460 capable of applying negative pressure (in this example, substantially radially-inward force) to lumen walls 461, while FIG. 8B depicts a positive pressure (expanding or expansion) source 462, capable of applying positive pressure (in this example, a substantially radially-outward force) to lumen walls 461.

Application of negative pressure to draw the lumen walls inward to form a seal with the lumen-traveling device, as depicted in FIG. 8A, may be useful for repairing or compensating for an aneurysm or other structural damage or imperfection to a lumen wall. Expansion and/or application of positive pressure by the lumen-traveling device may function to open a constricted lumen or secure a lumen-traveling device in place within a lumen, as depicted in FIG. 8B. Expansion of all or a portion of the lumen-traveling device may include expansion of a structural element or a portion thereof, which may be produced by inflation of one or more chambers with liquid or gas, or expansion or change in configuration of a shape-change material, bimetallic structure, etc.

Figures 9A, 9B:
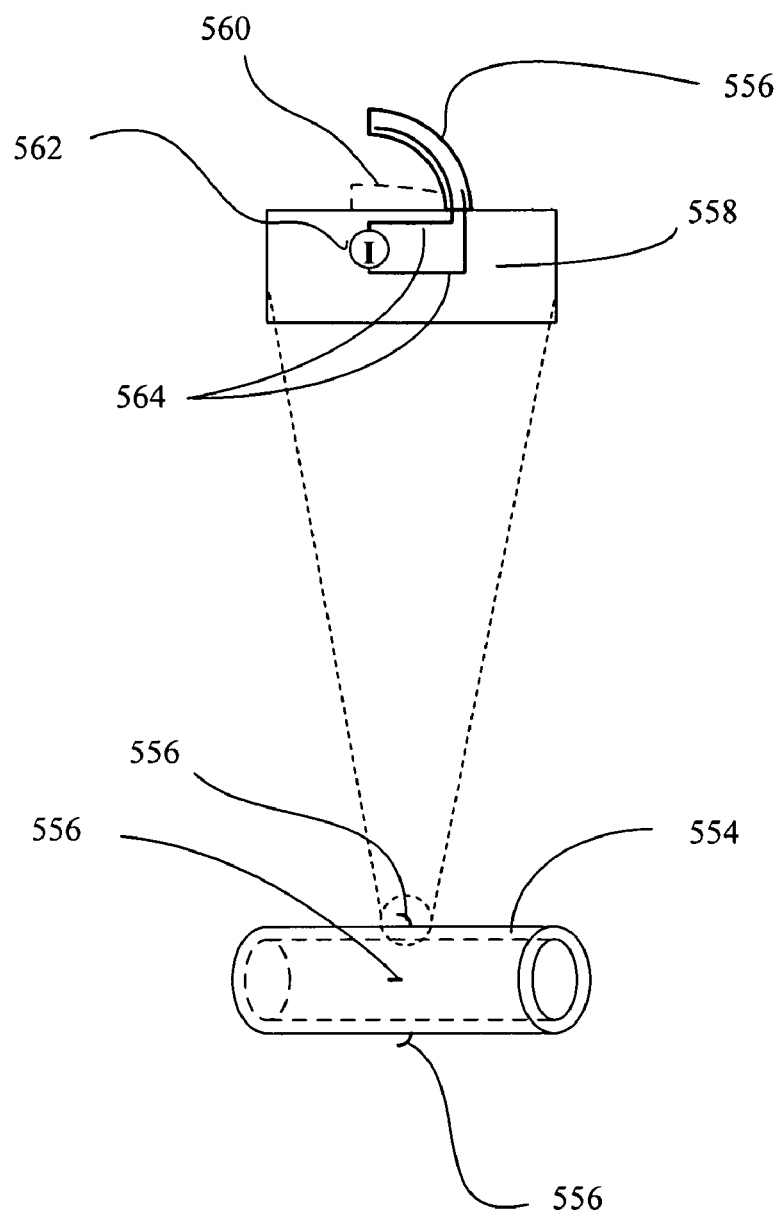
FIGS. 9A and 9B illustrate a positioning mechanism of a lumen-traveling device.

The active portion may include a positioning element operatively coupled to the response initiation circuitry and configured to secure the lumen-traveling device into position within the body lumen in response to receipt of the response initiation signal. A positioning element may be a hook or claw-like structure that may penetrate into or catch on the surface of the lumen wall, as in FIG. 5B, an expanding element that causes the lumen-traveling device to form a pressure-fit with the lumen, as in FIG. 8B, an adhesive material or glue, as in FIG. 5A, or other structure or material that may engage the lumen wall. A positioning element may also include a suction (negative pressure) generating mechanism that causes lumen-traveling device to adhere to the walls of the body lumen by suction, as depicted in FIG. 8A, for example. Claw or hook-like structures may be fixed or movable. Movable structures may include mechanical elements and/or materials that change shape or rigidity in response to temperature, electric field, magnetic field, or various other control signals. As an example, FIGS. 9A and 9B depict a lumen-traveling device 554 that includes positioning elements 556. Positioning elements such as positioning element 556 may be used as active portions in some embodiments of the invention. FIG. 9B is a close up view showing a portion 558 of lumen-traveling device 554, and detail of positioning element 556. Positioning element 556 is shown in an extended configuration (indicated by a solid outline) but may also be retracted (as indicated by the dashed outline and reference number 560). For example, positioning element 556 may change configuration on exposure to an electric current from current source 562 connected to positioning element 556 via circuitry 564. Positioning element 556 may be a claw-like projection that may be moved or extended to cause it to dig into a lumen wall to position lumen-traveling device 554 with respect to a lumen wall. Positioning element 556 may cause the lumen-traveling device to be retained in a desired position within a lumen for brief or extended periods of time. For example positioning elements may be extended to temporarily hold the lumen-traveling device in place and subsequently retracted to permit the lumen-traveling device to continue moving through the lumen. Alternatively, the lumen-traveling device may move through the lumen until it reaches a location of interest, and then the positioning elements may be extended substantially permanently to retain the lumen-traveling device at the location of interest substantially permanently. Various other types of positioning elements may be used, as well. For example, claws, clips, tensioning elements, expanding elements, and adhesives are all examples of positioning elements that may be used to retain a lumen-traveling device in a location. Certain positioning elements may be suited to retaining the lumen-traveling device in a location for extended periods, while other positioning elements may be more suited to retaining the lumen-traveling device in a location only briefly.

Figure 10A:
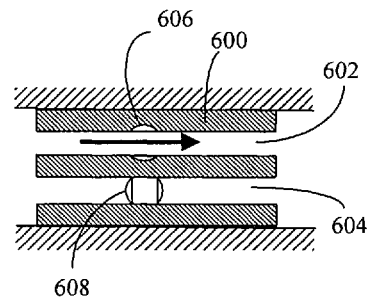
FIGS. 10A-10H depict examples of flow-modulating elements.

The active portion may include a flow-modulating element operatively connected to the response initiation circuitry and configured to modulate the flow of fluid through at least a portion of the body lumen in response to receipt of the response initiation signal. A flow-modulating element may modulate the flow of fluid through the body lumen to modify the amount of turbulence in the flow, the volume rate of flow, the fluid velocity, the direction of flow, or some other flow characteristic. A flow-modulating element may be, for example, a valve, a louver, a flow-directing element, a splitter or flow divider, a filter, a baffle, a channel restriction, a channel widening, or other structure capable of modifying the fluid flow according to principles of fluid dynamics known in the art. FIG. 10A illustrates lumen-traveling device portion 600 including a first channel 602 and a second channel 604, in which are located valves 606 and 608, respectively. Valve 606 is in the open position, allowing fluid flow as indicated by the arrow. Valve 608 is in the closed position, to block the flow of fluid. Valves 606 and 608 may be any of various types of controllable valves or microvalves.

Figure 10B:
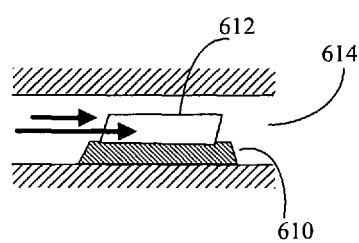

FIG. 10B illustrates a lumen-traveling device 610 including a louver 612, positioned within lumen 614. Louver 612 may modify the flow of fluid within lumen 614, e.g., by reducing turbulent flow or reducing flow velocity. Fluid may flow on either side of louver 612, as indicated by the arrows.

Figure 10C:
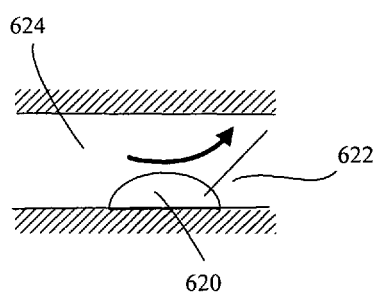

FIG. 10C illustrates a lumen-traveling device 620 including a flow-directing element 622. Flow-directing element 622 may direct the flow of fluid within lumen 624, so that fluid tends to move toward a particular portion of the lumen.

Figure 10D:
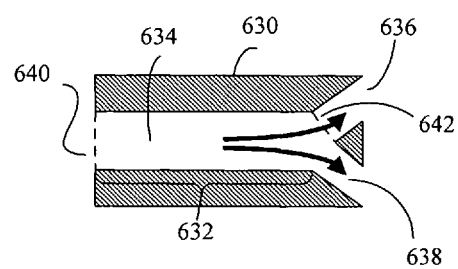

FIG. 10D depicts a portion 630 of a lumen-traveling device that includes a splitter (or flow divider) 632. Fluid may flow into main channel 634 and be divided so that it flows into branch channels 636 and 638, which may lead to additional structures within a lumen-traveling device or within the body lumen (e.g., if the lumen-traveling device was used in the vascular system, branch channels 636 and 638 could lead to particular blood vessels branching off of a larger blood vessel in which the lumen-traveling device resided). A valve placed across main channel entrance 640, or across the entrance of one or both branch channels (e.g., at entrance 642 of branch channel 636) may be used to control the operation of splitter 632.

Figure 10E:
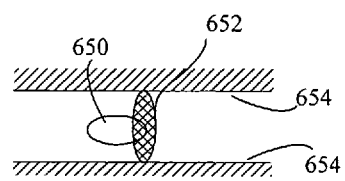

FIG. 10E depicts a lumen-traveling device 650 including a filter 652, in a body lumen defined by lumen walls 654. Filter 652 may be formed of screen, mesh, fibers, a sintered material, or various other materials, selected to remove particles in a particular size range or having particular affinity or binding properties from the fluid flowing though the filter.

Figure 10F:
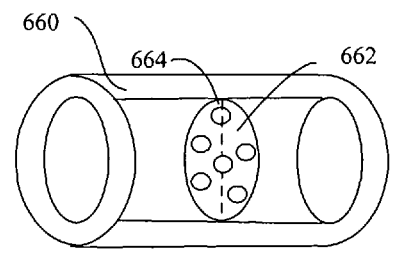

FIG. 10F depicts a lumen-traveling device 660 that include a baffle 662 for modifying the flow of fluid through the central opening 664 of lumen-traveling device 660. In some embodiments, e.g. as depicted in FIG. 10F, baffle 662 may be capable of rotating on axis 664 to move the baffle in an out of the channel to provide controlled modulation of fluid flow.

Figure 10G:
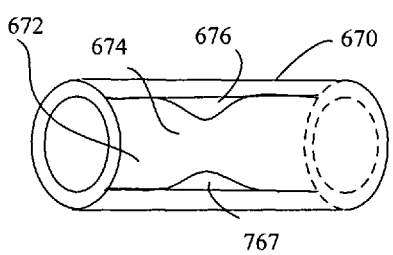

FIG. 10G depicts a lumen-traveling device portion 670 having a central channel 672 with a channel restriction 674. Channel restriction 674 may be formed by a projecting portion 676 extending around the circumference of channel 672. Projecting portion 676 may be an expandable or inflatable structure, to provide a controllable channel restriction.

Figure 10H:
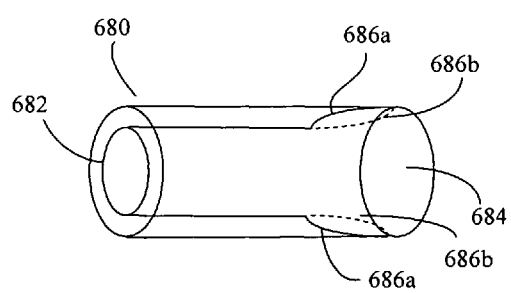

FIG. 10H depicts a lumen-traveling device portion 680 having a central channel 682 leading to a channel widening 684. Channel widening 684 may be formed by retraction of an expandable or inflatable structure 686 extending around the circumference of channel 682. Expandable or inflatable structure 686 is shown in retracted configuration 686a (thus forming channel widening 684) and in expanded configuration 686b, in which substantially no channel widening is formed. Expandable or inflatable structure 686 may be expanded to varying degrees to form varying sizes of channel widenings.

In some embodiments, the active portion of a lumen-traveling device may include a separator operatively connected to the response initiation circuitry and configured to selectively remove specific components from the fluid in response to detection of the condition of interest. A separator may be, for example, a molecular sieve or mechanical filter (including, for example, screen, mesh, fiber, etc., as depicted in FIG. 10E) having openings sized to allow passage of particles or structures of a particular size or size range, or a chemical or biochemical separator based on binding affinity, charge, surface energy, etc. as is well known to those in the art. For example, U.S. Patent Application 2005/0126916, which is incorporated herein by reference, provides an example of a microfabricated mesh. A separator may remove components that are not desired from the fluid (e.g., because they are foreign, harmful, etc.) or it may remove components for the purpose of collecting a sample for analysis. Thus, in related embodiments the active portion may include a sample collector. Either fluid or solid (e.g., tissue) samples may be collected or captured, depending on the type and/or design of the sample collector. Examples of sample collection structures and mechanisms are provided in U.S. Pat. Nos. 6,436,120 and 6,712,835, and HANNA, DARRIN M.; OAKLEY, BARBARA A.; STRYKER, GABRIELLE A.; "Using a System-on-a-Chip Implantable Device to Filter Circulating Infected Cells in Blood or Lymph"; IEEE Transactions on Nanobioscience; bearing dates of Jan. 25, 2003, March 2003; pp. 6-13; Vol. 2, No. 1; IEEE, all of which are incorporated herein by reference in their entirety. Another mechanism for capturing a solid material is a grasper as disclosed in U.S. Pat. No. 6,679,893, which is incorporated herein by reference.

Figure 11:
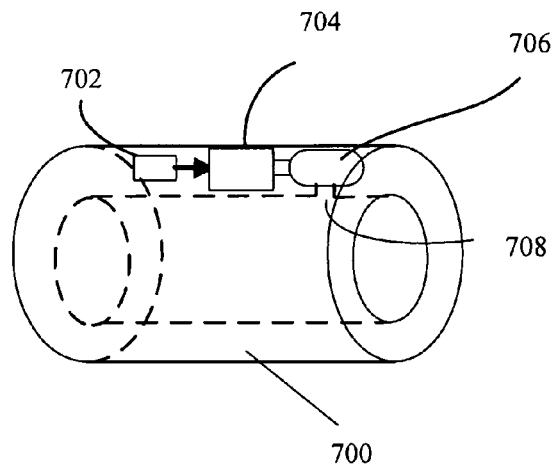
FIG. 11 is a depiction of a lumen-traveling device including a fluid-collection structure.

In some embodiments the active portion may include a fluid capture portion operatively coupled to the response initiation circuitry and configured to capture the detected material of interest. FIG. 11 depicts a device 700 including a fluid capture portion 706. Lumen-traveling device 700 includes sensor 702, response initiation circuitry 704, and fluid capture portion 706. Fluid enters fluid capture portion 706 via inlet 708. Fluid capture portion 706 may be a reservoir, for example, into which fluid is drawn by capillary action or by a negative pressure generated by a pump, for example. Captured fluid may be treated and released, or simply stored. In some applications, stored fluid may be subjected to analysis.

The sample collection portion may be a fluid capture portion configured to passively collect a fluid and/or constituents thereof, including cells or other biologics, within a matrix material, which might be located on the exterior of the lumen-traveling device in some embodiments, or contained in a chamber (e.g., fluid capture portion 706 in FIG. 11) in other embodiments. The matrix material may include an absorbent such as cotton, cellulose, natural or artificial sponge, a gel (a natural gel such as agarose, a natural and/or synthetic polymer gel, a hydrogel), a colloid, a gum base such as acacia gum, or micro particles. The sample collection portion may include a lipid monolayer, lipid bilayer, liposome, dendrimer, ligand affinity resin with conjugated peptide or antibody, ionophore, hydrosol, sol-gel, xerogel, aerogel, smart gel, hydrocarbon gel, or ferrogel. Many types of porous hydrogels are known, such as those used in the wound dressing of U.S. Pat. No. 6,372,248, incorporated herein by reference in its entirety. Alternatively, the sample collector may include a synthetic or natural adsorbent material such as a proteoglycan or charged polymer like polylysine, of a type that promotes the adhesion of one or more fluid constituent, e.g. a cell or protein. Other materials may include semi-specific or non-specific adsorbers, such as silica ($SiO_2$) or alumina ($Al_2O_3$) gel or ion exchange resin, possibly as part of the matrix material. Further examples of materials for sample collection are disclosed in U.S. Pat. Nos. 6,861,001 and 6,475,639, which are incorporated herein by reference. Alternatively or in addition, the sample collector may include one or more recognition elements of a type able to recognize and/or specifically bind a constituent of the fluid. Such a recognition element might be a biologic, such as a staphylococcus protein A complex, which generally binds immunoglobulins; a binding peptide or protein like an immunoglobulin; a DNA binding protein and/or genetically engineered protein; a nucleic acid, perhaps an aptamer; a carbohydrate; a lipid; a conjugate; or a synthetic molecule like an artificial antibody or other mimetic. U.S. Pat. Nos. 6,255,361; 5,804,563; 6,797,522; and 5,831,012 and U.S. Patent Application 2004/0018508 provide examples of such mimetics and are incorporated herein by reference in their entirety.

Figure 12:
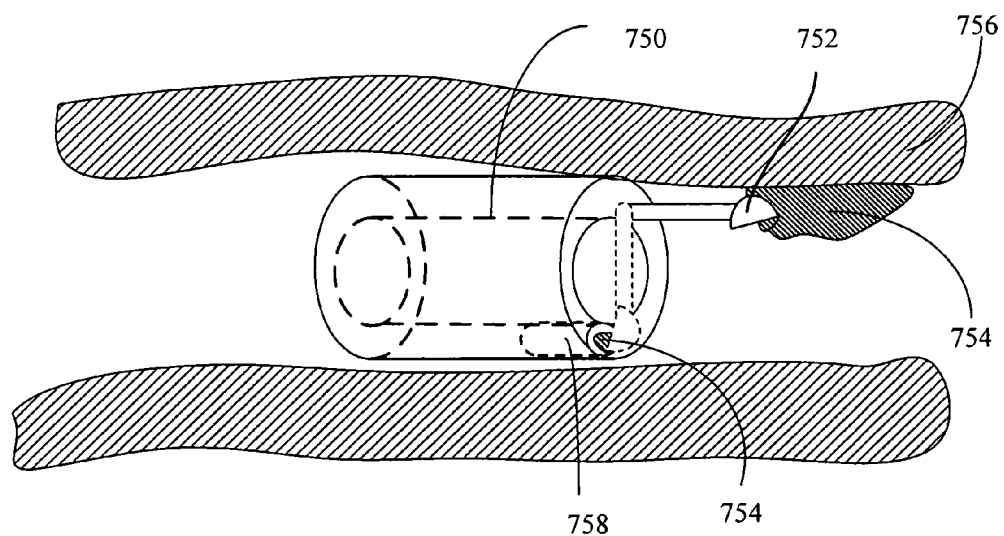
FIG. 12 is a depiction of a lumen-traveling device including a material collection structure.
Figure 13:
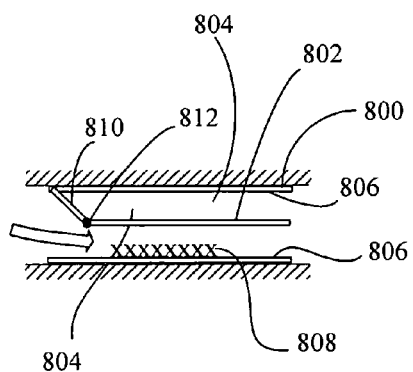
FIG. 13 illustrates an embodiment of an active portion of a lumen-traveling device.

FIG. 12 depicts lumen-traveling device 750 including a sample collection structure 752 capable of collecting a solid sample 754, e.g. for biopsy purposed and/or for removal of damaged, diseases, or otherwise unwanted tissue. In the example depicted in FIG. 12, solid sample 754 is a solid material found upon or immediately under the surface of the lumen-defining wall 756 (an arterial plaque, for example). Solid sample 754 placed in storage reservoir 758 by sample collection structure 752. In a related alternative embodiment, a lumen-traveling device may include a filter or selective binding region to remove materials from fluid moving past or through the lumen-traveling device.

In some embodiments, the active portion may include a catalytic portion operatively connected to the response initiation circuitry and configured to expose or activate a catalyst in response to receipt of the response initiation signal. Examples of catalysts include inorganic catalysts such as metal surfaces, and organic catalysts such as enzymes. A surface having catalytic properties (such as a metal) or having catalytic material adhered or bound thereto may be exposed or activated by directing the flow of fluid across, the surface, modifying a chemical property of the surface, or removing a covering from the surface. For example, as shown in cross-section in FIG. 13, a lumen-traveling device portion 800 may include a channel divider 802 separating two channels 804 and 806. Channel 806 includes catalytic material 808, which is capable of catalyzing a reaction with one or more component of fluid flowing through channel 806, as indicated by the arrow. A movable gate 810 on pivot 812 may block the flow of fluid into channel 804 while permitting the flow of fluid into channel 806 and across catalytic material 808, or it may be repositioned to block the flow of fluid into channel 806 while permitting the flow of fluid into channel 804. In some embodiments of a lumen-traveling device, the active portion may include a catalytic portion operatively connected to the response initiation circuitry and configured to expose a catalytic surface to the fluid in response to detection of the condition of interest. The catalytic surface may catalyze a reaction that modifies or destroys a material of interest, for example.

Figure 14:
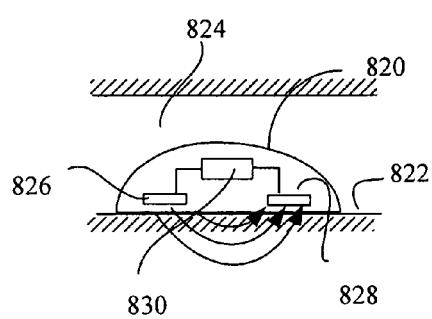
FIG. 14 illustrates an embodiment of an active portion of a lumen-traveling device.

The active portion may include an electric field source, as depicted in FIG. 14, operatively connected to the response initiation circuitry and configured to apply an electric field to the fluid and/or lumen wall or surrounding tissue in response to receipt of the response initiation signal. For example, a lumen-traveling device 820, here shown contacting wall 822 of lumen 824, may include a first contact 826 and second contact 828 connected to source 830. Source 830 may be a capacitor or other charge storing device, to generate a static electric field, or it may be current source capable of generating a dynamic electric field.

Figure 15:
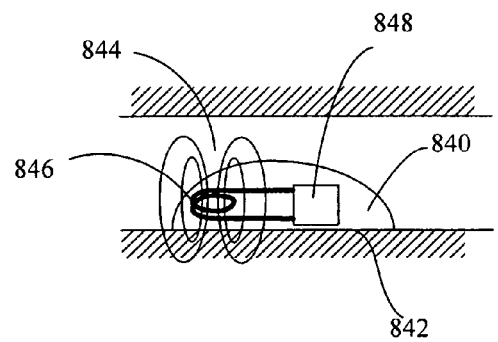
FIG. 15 illustrates an embodiment of an active portion of a lumen-traveling device.

Alternatively, as shown in FIG. 15, an active portion may include a magnetic field source operatively connected to the response initiation circuitry and configured to apply a magnetic field to the fluid and/or lumen wall or surrounding tissue in response to receipt of the response initiation signal. A lumen-traveling device 840 adjacent wall 842 of lumen 844 may include (for example) a coil 846 connected to current source 848. Current from current source 848 flowing through coil 846 will produce a magnetic field as indicated in FIG. 15. The magnetic field source need not include a coil; as known to those of skill in the art, a magnetic field may be generated by current flowing through various types of structures. Moreover, one or more fixed magnets may be included in a magnetic field source.

Figure 16:
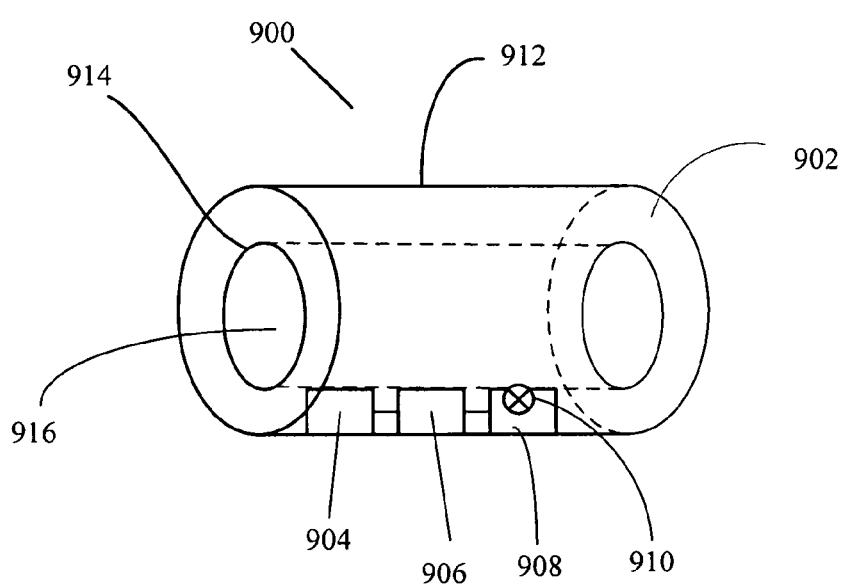
FIG. 16 is an illustration of a device including stored deliverable material.

In some embodiments, the active portion of a lumen-traveling device may include a material release structure operatively coupled to the response initiation circuitry and configured to release a material in response to receipt of the response initiation signal. FIG. 16 depicts a delivery device 900 including a structural element 902, sensor 904, control signal generation circuitry 906, and release structure 908 including release mechanism 910. Structural element 902 includes external surface 912, configured to fit within a body lumen, and internal surface 914 defining central opening 916, through which a fluid may flow. Upon sensing of a condition of interest in the fluid by sensor 904, control signal generation circuitry 906 may cause release of material from material release structure 908 by activating release mechanism 910. Release mechanism 910 may include a variety of different types of release mechanisms, including, for example, a controllable valve. Various types of valves and microvalves are known to those of skill in the art, and may be used to regulate the release of material from material release structure 908 in response to a control signal from control signal generation circuitry 906. Control signal generation circuitry 906 may activate release mechanism 910 by supplying a delivery control signal, which may be an electrical signal, for example. In some embodiments, other types of delivery control signals, including magnetic signals, optical signals, acoustic signals, or other types of signals may be used. Combinations of several types of signals may be used in some embodiments. In some embodiments, control signal generation circuitry 906 may cause release of material from material release structure in response to passage of a certain amount of time, as monitored, for example, by a timekeeping device. In some embodiments, material release structure 908 may include a pressurized reservoir of material. In still other embodiments, the material (or materials) to be released may be generated within the material release structure. In other embodiments, the material(s) may diffuse away from the release structure along a concentration gradient.

Figure 17:
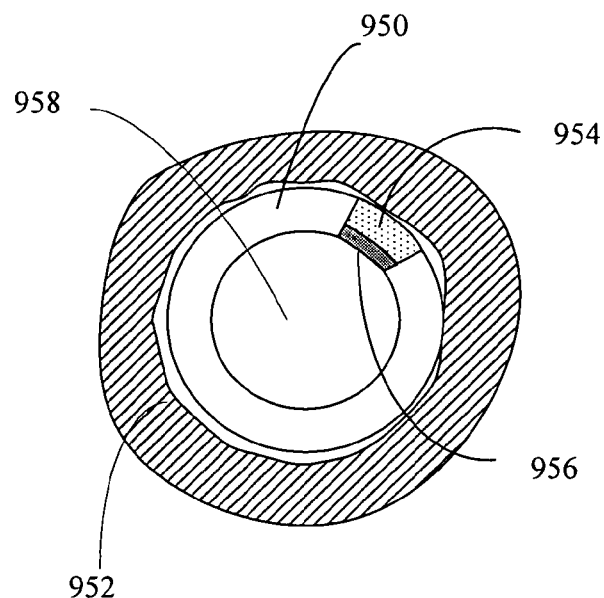
FIG. 17 is a cross-sectional view of an embodiment of a device including a stored deliverable material and a barrier release mechanism.

FIG. 17 illustrates, in cross sectional view, a structural element 950 of a lumen-traveling device positioned in a lumen-containing structure 952. A reservoir 954 contains stored deliverable material. Barrier 956 is a controllable barrier that control the release of the stored deliverable material into central opening 958, and thus into a fluid that fills and/or flows through lumen-containing structure 952.

Figure 18:
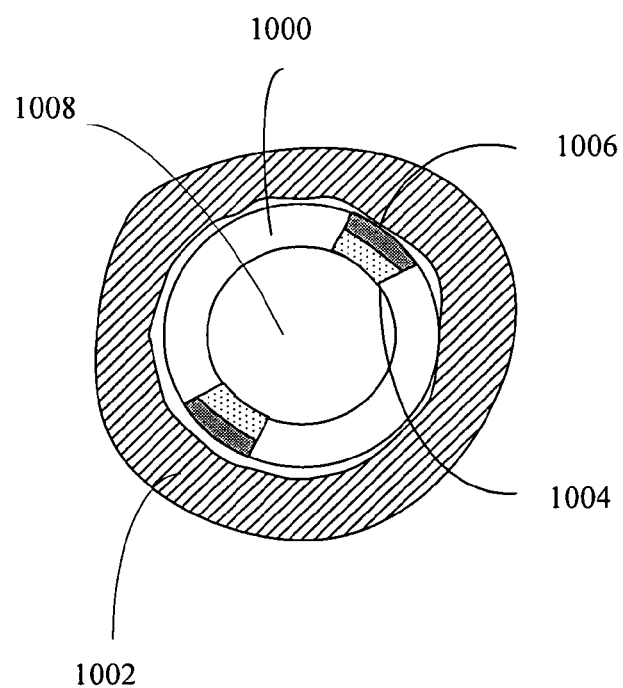
FIG. 18 is a cross-sectional view of another embodiment of a device including a stored deliverable material and a barrier release mechanism.

FIG. 18 illustrates an embodiment similar to that depicted in FIG. 20, including a structural element 1000 of a lumen-traveling device positioned in a lumen-containing structure 1002. A reservoir 1004 contains stored deliverable material. Barrier 1006 is a controllable barrier that controls the release of the stored deliverable material. In the embodiment of FIG. 18, activation of barrier 1006 causes release of the stored deliverable material toward the lumen wall of lumen-containing structure 1002, rather than into central opening 1008.

FIGS. 19A, 19B, 20A, 20B, 22A and 22B, illustrate several alternative embodiments of material release structures that include controllable barriers. In FIGS. 19A and 19B, release structure 1150 includes reservoir 1152 containing stored deliverable material 1154. As shown in FIG. 19A, while rupturable barrier 1156 is intact, stored deliverable material 1154 is contained within reservoir 1152. As shown in FIG. 19B, when rupturable barrier 1156 has been ruptured (as indicated by reference number 1156'), deliverable material 1154 may be released from reservoir 1152. Rupturable barrier 1156 may be ruptured by an increase of pressure in reservoir 1152 caused by heating, for example, which may be controlled by response initiation circuitry. In another alternative shown in FIGS. 20A and 20B, release structure 1200 includes reservoir 1202 containing stored deliverable material 1204. As shown in FIG. 20A, while degradable barrier 1206 is intact, stored deliverable material 1204 is contained within reservoir 1202. As shown in FIG. 20B, degradation of degradable barrier 1206 to degraded form 1206' causes stored deliverable material 1204 to be released from reservoir 1204. FIGS. 21A and 21B depict release structure 1250 including reservoir 1252 containing stored deliverable material 1254. FIG. 21A shows barrier 1256, which has a controllable permeability, in a first, impermeable state, while FIG. 21B shows barrier 1256 in a second, permeable state (indicated by reference number 1256'). Stored deliverable material 1254 passes through barrier 1256', when it is in its permeable state, and is released. Rupturable barriers as described above may be formed from a variety of materials, including, but not limited to, metals, polymers, crystalline materials, glasses, ceramics, semiconductors, etc. Release of materials through rupture or degradation of a barrier is also described in U.S. Pat. No. 6,773,429, and U.S. Patent Application 2004/0260391, which are incorporated herein by reference. Semipermable barriers having variable permeability are described, for example, in U.S. Pat. No. 6,669,683, which is incorporated herein by reference. Those of skill in the art will appreciate that barriers can be formed and operated reversibly through multiple release cycles, in addition to the single-release functionality available from a rupturable barrier.

Figure 22:
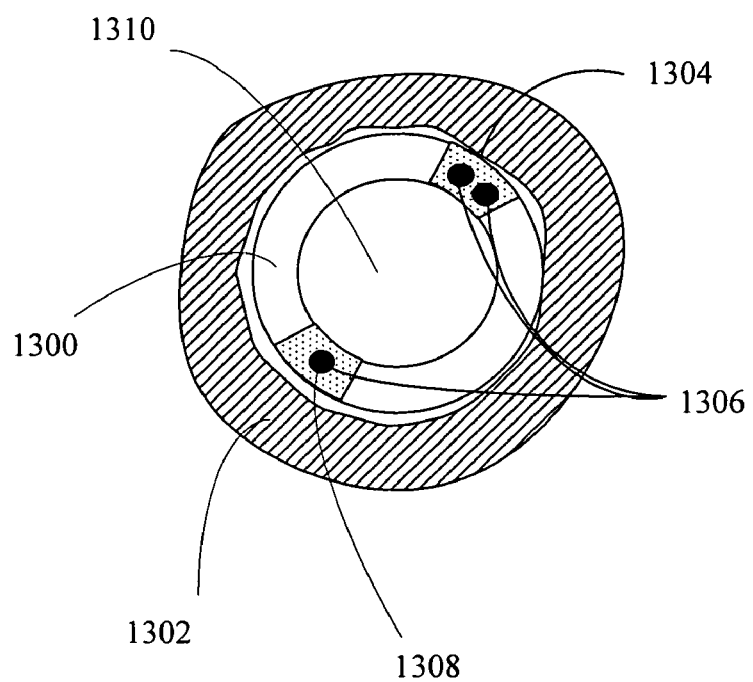
FIG. 22 is a cross-sectional view of another embodiment of a device including a stored deliverable material.

FIG. 22 depicts another embodiment of a structural element of a lumen-traveling device 1300 in a lumen containing structure 1302. Lumen-traveling device 1300 includes stored deliverable material 1304 dispersed in a carrier material 1306. Stored deliverable material 1304 may be released from carrier material 1306 by release mechanism 1308 upon activation of release mechanism 1308. Released deliverable material 1304 may be released into central opening 1310 of lumen-traveling device 1300 and/or into the area around the lumen-traveling device.

Figure 23A:
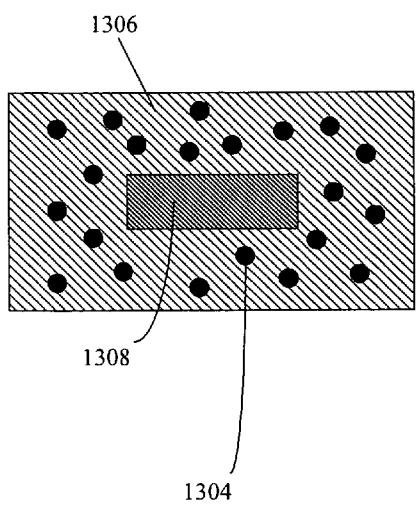
FIGS. 23A and 23B are depictions of the release of a stored deliverable material from a carrier material.
Figure 23B:
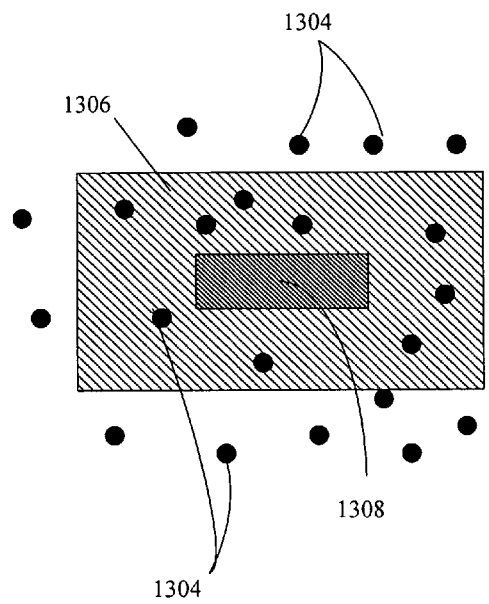

FIGS. 23A and 23B depict in greater detail the release of stored deliverable material from the carrier material. In FIG. 23A, deliverable material 1304 is stored in carrier material 1306. Carrier material 1306 may be, for example, a polymeric material such as a hydrogel, and deliverable material is dispersed or dissolved within carrier material 1306. Release mechanism 1308 may be a heating element, for example a resistive element connected directly to response initiation circuitry, or an electrically or magnetically responsive material that may be caused to move, vibrate or heat, by an externally applied electromagnetic field, which in turn causes release of deliverable material 1304 from carrier material 1306, as shown in FIG. 23B. See, for example, U.S. Pat. Nos. 5,019,372 and 5,830,207, which are incorporated herein by reference. In some embodiments, an electrically or magnetically active component may be heatable by an electromagnetic control signal, and heating of the electrically or magnetically active component may cause the polymer to undergo a change in configuration. An example of a magnetically responsive polymer is described, for example, in Neto, et al, "Optical, Magnetic and Dielectric Properties of Non-Liquid Crystalline Elastomers Doped with Magnetic Colloids"; Brazilian Journal of Physics; bearing a date of March 2005; pp. 184-189; Volume 35, Number 1, which is incorporated herein by reference. Other exemplary materials and structures are described in Agarwal et al., "Magnetically-driven temperature-controlled microfluidic actuators"; pp. 1-5; located at: http://www.unl.im.dendai.ac.jp/INSS2004/INSS2004_papers/OralPresentations/C2.pdf or in U.S. Pat. No. 6,607,553, both of which are incorporated herein by reference. In connection with the release of materials and/or detection of a local condition, in some embodiments the permeability of the lumen wall to the released material may be increased by the use of retractable protrusions that penetrate the lumen wall, as described in U.S. Pat. No. 6,991,617; by hollow microneedles capable of penetrating the lumen wall, as described in U.S. Pat. No. 6,743,211; by introduction of a magnetic or electromagnetic field (Physical and Chemical Permeation Enhancers in Transdermal Delivery of Terbutaline Sulphate, *AAPS PharmSciTech*, 2001; 2 (1) 1-5; http://www.aapspharmscitech.org/view.asp?art=pt0201_tn1); by a chemical permeability enhancer as described in U.S. Pat. No. 6,673,363, which may be released from the lumen-traveling delivery device along with the material or from a separate reservoir or other source or which may be incorporated within a component of the device for example as a coating; or by an electrical permeability enhancer, such as a voltage source for producing electroporation and/or iontophoresis, as in U.S. Pat. Nos. 6,022,316, 6,219,577, 6,512,950; or by sonophoresis or phonophoresis, perhaps using techniques based on those in U.S. Pat. No. 6,322,532; all of which patents are incorporated herein by reference in their entirety. Chemical permeation enhancers may include, for example, isopropyl myristate, bile salts, surfactants, fatty acids and derivatives, chelators, cyclodextrins, or chitosan. Other technologies that might be useful for enhancing permeability may include inotophoresis, microdialysis, ultrafiltration, electromagnetic, osmotic, electroosmosis, sonophoresis, suction, electroporation, thermal poration, microporation, microfine cannulas, skin permeabilization, or a laser.

Figure 24:
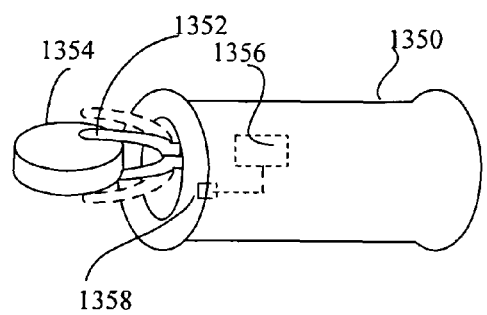
FIG. 24 illustrates a lumen-traveling device including a device release structure.

The active portion may include a device release structure operatively coupled to the response initiation circuitry and configured to release a device in response to receipt of the response initiation signal. For example, FIG. 24 illustrates a lumen-traveling device 1350 including device release structure 1352 (which in this example is a grasper type structure) holding a device 1354 that is to be released into a body lumen. A response initiation circuitry 1356 may receive a sense signal from sensor 1358, and generate a response initiation signal to cause device release structure 1352 to release device 1354. Device 1354 may be any type of device small enough to be carried by a lumen-traveling device. For example, device 1354 might be a sensor with a transmitter, a device that releases a drug or other compound, or an electrical or magnetic stimulation device. The device configuration illustrated in FIG. 24 is intended as an example only, and the device released by a device release structure of a lumen-traveling device may have various configurations. It will be appreciated that the device release structure may be designed to be compatible with a particular type of device, or may be suitable for use with a number of types of devices.

Figure 25A:
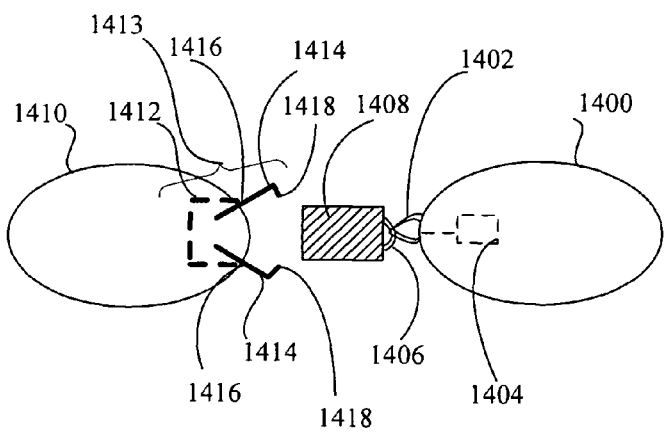
FIGS. 25A and 25B illustrate lumen-traveling devices including delivery and receiving structures.
Figure 25B:
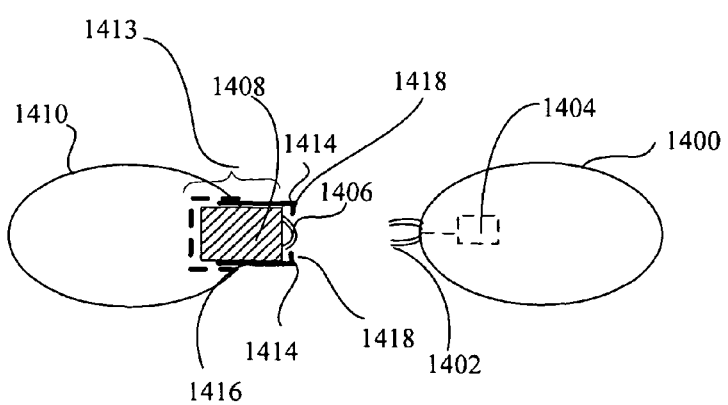

As illustrated in FIGS. 25A and 25B, the active portion of a lumen-traveling device 1400 may include a delivery structure 1402 operatively coupled to the response initiation circuitry 1404 and configured to deliver a material or structure 1408 to a receiving device in 1410 response to receipt of the response initiation signal. In FIG. 25A, lumen-traveling device 1400 includes delivery structure 1402, which is capable of attaching to connector 1406 on structure 1408, thus permitting structure 1408 to be carried by lumen-traveling device 1400. In use, lumen-traveling device 1400 may carry structure 1408 to receiving device 1410. A response initiation signal may be generated by response initiation circuitry 1404 when lumen-traveling device 1400 is close to receiving device 1410. Receiving device 1410 may include a receiving structure 1413 made up of recess 1412 and receiving arms 1414 mounted on pivots 1416. Receiving device 1410 may be a non-mobile device or structure that has been implanted or placed in the lumen, or, in some embodiments, receiving device 1410 may be a second lumen-traveling device. The second lumen-traveling device may include various features as described previously; the active portion may include a receiving structure (e.g., receiving structure 1413 in FIGS. 25A and 25B) operatively coupled to the response initiation circuitry and configured to receive a material or structure (e.g., structure 1408) from a delivering device 1400 in response to receipt of the response initiation signal. As structure 1408 is pushed into receiving recess 1412, receiving arms 1414 may be caused to move on pivots 1416 to allow structure 1408 to slide into recess 1412, where it may be retained by projections 1418, as illustrated in FIG. 25B.

The active portion may include a collecting structure operatively coupled to the response initiation circuitry and configured to collect a structure (including, but not limited to, a man-made structure) from the body lumen in response to receipt of the response initiation signal. The collecting structure may be comparable to a device release structure as depicted previously, and may collect a structure from the body lumen by attaching to a connector such as connector 1406. In related embodiments, the collecting structure may grasp the body of a device-to-be-collected, generally as depicted in FIG. 24. In other embodiments, a collecting structure may be large enough to receive the structure to be collected within the body of the lumen-traveling device.

The active portion of a lumen-traveling device may include an attachment structure operatively coupled to the response initiation circuitry and configured to attach to a structure (particularly a man-made structure) present in the body lumen in response to receipt of the response initiation signal. The attachment structure may be a grasper shown in FIG. 24 or the device release structure shown in FIGS. 25A and 25B. Other attachment mechanisms may include various other mechanical mechanisms, or be based on magnetic attraction, electrostatic forces, chemical bonding, surface interactions, etc. Microscale structures for gripping or grasping are described in U.S. Pat. No. 6,398,280, and "Zyvex NanoEffector Microgrippers"; Nanotechnology at Zyvex; printed on Dec. 7, 2006; pp. 1-2; located at http://www.zyvex.com/Products/Grippers_Features.html and "Zyvex NanoEffector Microgrippers"; Zyvex.com; bearing a date of 2006; pp. 1-2; Zyvex Corporation, all of which are incorporated herein by reference.

The active portion may include one or more tools, especially surgical tools, e.g., tools for cutting, as depicted in FIGS. 26A and 26B, scraping, as depicted in FIG. 27, suturing, or cauterizing. In FIG. 26A, a lumen-traveling device 1450 includes a cutting tool 1452 mounted on shaft 1454, which may be retracted into channel 1456, driven by translation motor 1458. In the embodiment depicted in FIG. 26A, lumen-traveling device 1450 includes main lumen 1460. A cross-section of lumen-traveling device 1450 taken at section line B-B, showing shaft 1454, channel 1456, and main lumen 1460 is illustrated in FIG. 26B. Channel 1456 and main lumen 1460 pass through core portion 1462 of lumen-traveling device 1450.

FIG. 27 depicts a lumen-traveling device 1500, generally similar to lumen-traveling device 1450 in FIGS. 26A and 26B, but including a scraping tool 1502. Scraping tool 1502 is mounted on shaft 1504 which may retract in channel 1506. Shaft 1504 may also rotate in channel 1506, both during use of scraping tool 1502, as illustrated with the double-headed arrow, and also to permit the scraping tool 1502 to be retracted into main lumen 1508 of the lumen-traveling device, to the position shown in dashed lines. An example of a scraping tool is presented in JP 2005-74229, which is incorporated herein by reference.

Various examples of suturing tools are disclosed and described in U.S. Pat. Nos. 7,131,979 and 5,964,773, both of which are incorporated herein by reference. A cauterizing tool may be a specialized form of a heating element, as depicted in FIG. 7A, or electromagnetic radiation source as depicted in FIG. 7C. Tools may be micro-scale tools formed by MEMS manufacturing techniques, e.g., as described in U.S. Pat. No. 5,728,089, which is incorporated herein by reference. It will be appreciated that various other active portions disclosed herein may also have surgical utility: for example, active portions for performing sample collection, material release, heating, cooling, etc. may all have surgical applications.

Figure 28:
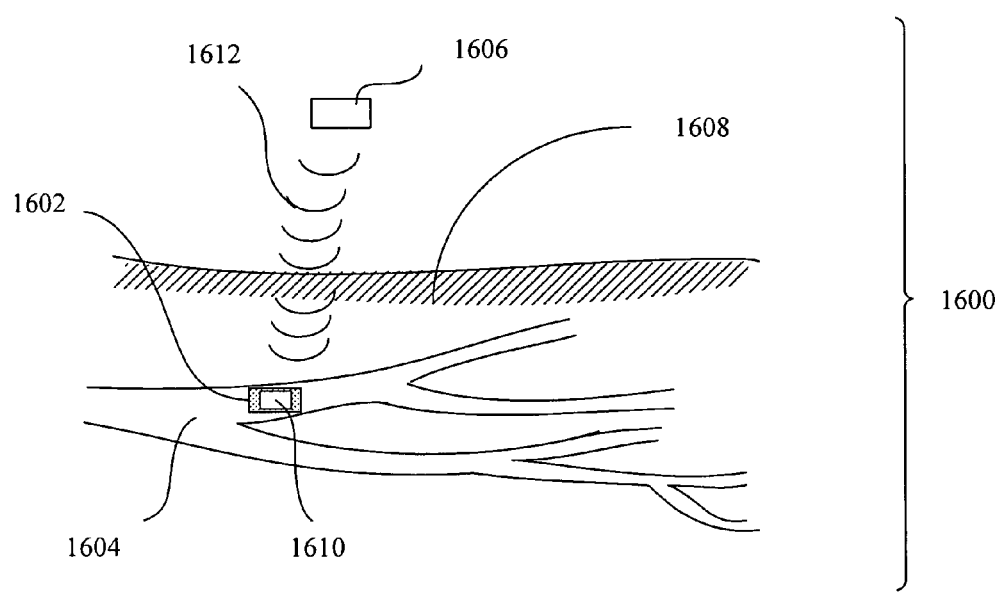
FIG. 28 is an illustration of a lumen-traveling system that includes an external control portion.

FIG. 28 depicts a system 1600 including a lumen-traveling device 1602 located in a body lumen 1604 (here, a portion of the circulatory system) and a remote portion 1606, which in this example is located outside body surface 1608. The active portion of a lumen-traveling device 1602 may include a transmitter 1610 operatively coupled to the response initiation circuitry and configured to transmit a detection signal 1612 to a remote location (e.g., remote portion 1606) in response to receipt of the response initiation signal. The detection signal may be used to inform a medical caregiver about a condition of the subject so that suitable treatment may be provided by the caregiver, or the detection signal may contain information usable by an automated system to control operation of the lumen-traveling device.

Various types of propelling mechanisms may be used to move the lumen-traveling device through the body lumen. Examples are provided in U.S. Pat. Nos. 5,337,732; 5,386,741; 5,662,587; and 6,709,388; and KASSIM, IRWAN; PHEE, LOUIS; N G, WAN S.; GONG, FENG; DARIO, PAOLO; MOSSE, CHARLES A. ("Locomotion Techniques for Robotic Colonoscopy"; IEEE ENGINEERING IN MEDICINE AND BIOLOGY MAGAZINE; bearing dates of May/June 2006 and 2006; pp. 49-56; IEEE); CHRISTENSEN, BILL ("Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006); ANANTHASWAMY, ANIL ("First robot moved by muscle power"; bearing a date of Feb. 27, 2004; pp. 1-3; New Scientist; located at http://www.newscientist.com/article.ns?id=dn4714; printed on Sep. 12, 2006); and FREITAS JR., ROBERT A. ("8.2.1.2 Arteriovenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine Volume I: Basic Capabilities"; bearing a date of 1999; pp. 211-214, pp. 316-318; Landes Bioscience; Georgetown, Tex., USA); all of which are incorporated herein by reference in their entirety. The propelling mechanism of the lumen-traveling device may include one or more cilium-like or flagellum-like structures, for example, as described in U.S. Patent Application 2004/0008853; MATHIEU, J-B.; MARTEL, S.; YAHIA, L'H.; SOULEZ, G.; BEAUDOIN, G. ("MRI Systems as a Mean of Propulsion for a Microdevice in Blood Vessels"; bearing a date of 2003; pp. 3419-3422; IEEE); LU, ZHAO; MARTEL, SYLVAIN ("Preliminary Investigation of Bio-carriers Using Magnetotactic Bacteria"; Proceedings of the 28th IEEE EMBS Annual International Conference; bearing dates of Aug. 30, 2006-Sep. 3, 2006 and 2006; pp. 3415-3418; IEEE), [INCLUDE 'PROPULSION SYSTEM FOR FANTASTIC VOYAGE ROBOT'] and MARTEL, SYLVAIN ("Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28th IEEE EMBS Annual International Conference; bearing dates of Aug. 30, 2006-Sep. 3, 2006 and 2006; pp. 3399-3402; IEEE), all of which are incorporated herein by reference. The propelling mechanism may include rollers or wheel-like structures, as shown in U.S. Pat. No. 7,042,184 and U.S. Patent Application 2006/0119304, both of which are incorporated herein by reference; screw-like structures, as disclosed in IKEUCHI, K.; YOSHINAKA, K.; HASHIMOTO, S.; TOMITA, N. ("Locomotion of Medical Micro Robot with Spiral Ribs Using Mucus"; Seventh International Symposium on Micro Machine and Human Science; bearing a date of 1996; pp. 217-222; IEEE), which is incorporated herein by reference; appendages capable of walking motion, as described, for example, in U.S. Pat. No. 5,574,347; CHRISTENSEN, BILL ("Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006) and MARTEL, SYLVAIN ("Fundamentals of high-speed piezo-actuated three-legged motion for miniature robots designed for nanometer-scale operations"; pp. 1-8), incorporated herein by reference, and others. Appendage-like structures may intermittently engage the lumen wall and push the structural element with respect to the lumen wall with a walking-type motion, or may push against fluid within the lumen in a paddling or swimming motion. In some embodiments, the propelling mechanism may drive rotational movement of a lumen-wall-engaging structure with respect to the structural element, e.g., as in turning of a wheel or a screw element to propel the structural element through a lumen. Propelling mechanisms may include mechanical or micromechanical structures driven by at least one motor, micromotor, or molecular motor, or by expansion or change in configuration of a shape change polymer or metal. A molecular motor may be a biomolecular motor that runs on a biological chemical such as ATP, kinesin, RNA polymerase, myosin dynein, adenosinetriphosphate synthetase, rotaxanes, or a viral protein.

FIG. 1 depicts an example of a lumen-traveling device that includes a propelling mechanism which drives rotational movement of a lumen-wall-engaging structure. Lumen-traveling device 10 may include a structural element 12 configured to fit within at least a portion of a body lumen 14. The structural element 12 may include a lumen-wall-engaging portion 16. Lumen-traveling device 10 may also include a propelling mechanism 20 capable of producing movement of the structural element 12 through a body lumen 14 in which the structural element is deployed. Here, propelling mechanism 20 includes two rotating wheels, the outer rims of which form lumen-wall-engaging portions 16.

Figure 29A:
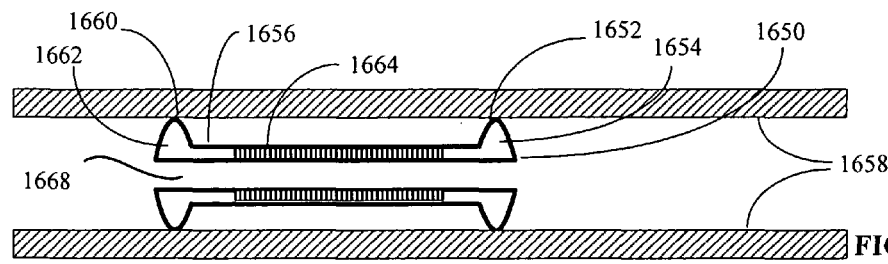
FIGS. 29A-29E illustrate a propelling mechanism of a lumen-traveling device.
Figure 29B:
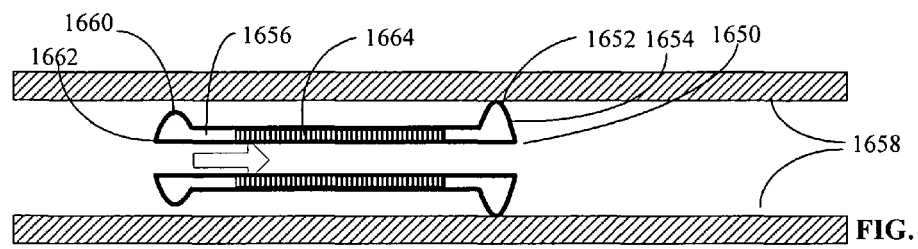
Figure 29C:
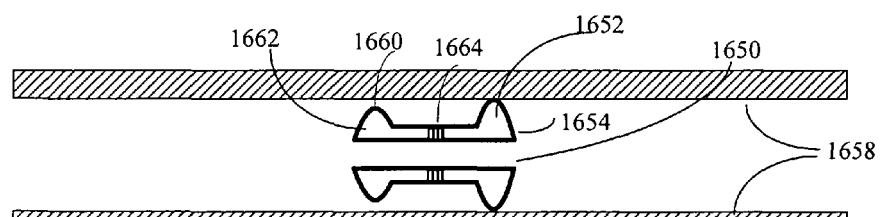
Figure 29D:
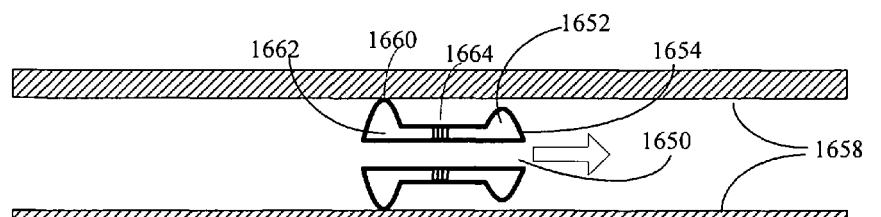
Figure 29E:
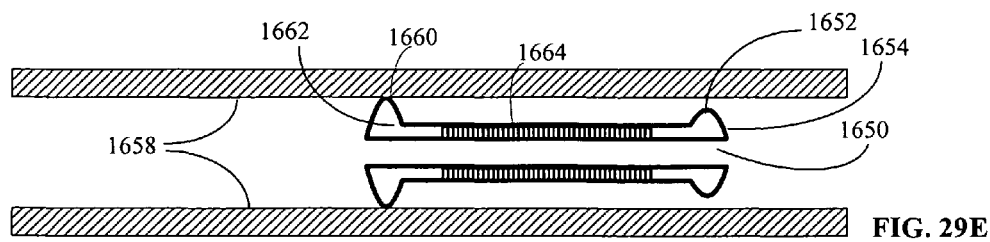

In several alternative approaches, two (or more) lumen-wall-engaging portions may engage the lumen walls intermittently. FIGS. 29A-29E depict (in cross-section) an embodiment of a lumen-traveling device 1650 which includes a motion-arresting portion including a first lumen-wall-engaging structure 1652 on first portion 1654 of the lumen-traveling device, capable of at least intermittently engaging an inner surface 1658 of body lumen in which the lumen-traveling device 1650 is deployed. The device may also include at least one second lumen-wall-engaging structure 1660 on second portion 1662 of the lumen-traveling device, wherein the propelling mechanism produces lengthening and shortening of the distance, between the first lumen-wall-engaging structure 1652 and the second lumen-wall-engaging structure 1660 in coordination with alternate engagement of the first lumen-wall-engaging structure 1652 and the second lumen-wall-engaging structure 1660 with the inner surface 1658 of the body lumen in which the lumen-traveling device is deployed. In the present example, the lengthening and shortening of the distance between the first and second lumen-wall-engaging structures may take place in region 1664, but in other embodiments, the distance between the first and second lumen-wall-engaging structures may change due to change in position of the lumen-wall-engaging structures, e.g., in limbs that move relative to each other to produce walking-type motion. Portions of the lumen-traveling device (e.g. end portion 1656) may not change in length, in order to provide a stable location for mounting of control circuitry (not shown). The alternate engagement and disengagement of the lumen wall by the first and second lumen-wall-engaging structures may produce inchworm-type propulsion of the device through the body lumen. Lumen-traveling device 1650 includes a propelling mechanism capable of producing relative extension and retraction of the at least two lumen-wall-engaging structures (1652 and 1660) with respect to each other in combination with alternate engagement and disengagement of the body lumen wall to produce inch-worm-like movement of the lumen-traveling stimulation device with respect to the body lumen wall. The embodiment of the lumen-traveling device depicted in FIGS. 29A-29E has a tubular structure with a central lumen 1668, to permit movement of fluid through the device. FIG. 29A depicts lumen-traveling device in which lumen-wall-engaging structures 1652 and 1660 are extended to engage with inner surface 1658. In FIG. 29B, second lumen-wall-engaging structure 1660 has been retracted, and region 1664 shortened to cause movement of second portion 1662 of lumen-traveling device 1650 in the direction indicated by the arrow, to attain the configuration shown in FIG. 29C. Second lumen-wall-engaging structure 1660 is then extended to engage inner surface 1658, and first lumen-wall-engaging structure 1652 is retracted, to attain the configuration shown in FIG. 29D. Then, as indicated in the arrow in FIG. 29D, region 1664 is extend to move first portion 1654 of lumen-traveling device 1650 in the direction indicated by the arrow in FIG. 29D. At the end of the movement cycle, lumen-traveling device 1650 has attained the configuration shown in FIG. 29E. First lumen-wall-engaging structure 1652 may then be extended to engage inner surface 1658, as depicted in FIG. 29A. It will be appreciated that by repeating the motion cycle illustrated in FIGS. 29A-29E, movement of the lumen-traveling device through the lumen may be accomplished. Various types of lumen-wall-engaging structures may be used in devices that produce inchworm-type motion, and in addition to lumen-wall-engaging structures that expand or extend, structures that engage the lumen wall through other mechanisms (for example, with suction mechanisms, adhesives, claws or hooks) may be used. Lumen-traveling devices that utilize an inchworm-type propulsion mechanism with suction mechanisms for engaging the surface of the heart are disclosed in PATRONIK, N. A.; OTA, T.; ZENATI, M. A.; RIVIERE, C. N. ("Improved Traction for a Mobile Robot Traveling on the Heart"; Proceedings of the 28th IEEE EMBS Annual International Conference; bearing dates of Aug. 30, 2006-Sep. 3, 2006 and 2006; pp. 339-342; IEEE); DARIO, P.; CARROZZA, M. C.; LENCIONI, L.; MAGNANI, B.; D'ATTANASIO, S. ("A Micro Robotic System for Colonoscopy"; Proceedings of the 1997 IEEE International Conference on Robotics and Automation; bearing dates of April 1997 and 1997; pp. 1567-1572; IEEE) and DONGXIANG, CHI; GUOZHENG, YAN ("An earthworm based miniature robot for intestinal inspection"; Proceedings of SPIE; bearing dates of Nov. 7, 2001-Nov. 9, 2001; pp. 396-400; Volume 4601; SPIE); all of which are incorporated herein by reference in their entirety.

Radially and longitudinally expanding or extending structures may be mechanical or micromechanical structures, expandable materials, inflatable structures, or shape-changing materials or structures. While reference is made to expandable and inflatable materials and structures here, and throughout the specification, it will be appreciated that structures that are specified as being expandable and inflatable may also be contractable or deflatable, and thus capable of reversible change in dimension. Reversible changes of dimension may be used in generating cyclical motions for propelling a lumen-traveling device. In some embodiments, expansion/contraction may force fluid out of the device to generate jet or vortext propulsion. Nevertheless, it is contemplated that, in some applications, materials and structures that change dimension in one direction (only expansion or only contraction) may be used.

Figure 30A:
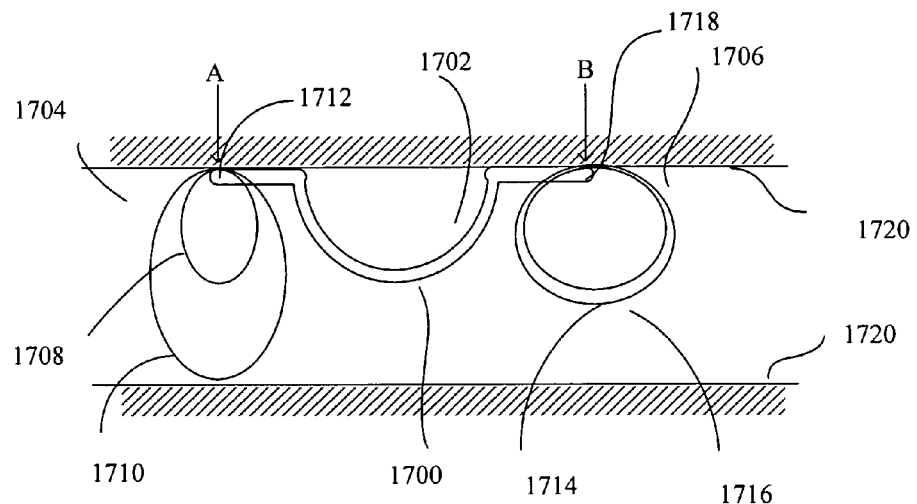
FIGS. 30A and 30B illustrate an example of a lumen-traveling device including expanding and extending structures.
Figure 30B:
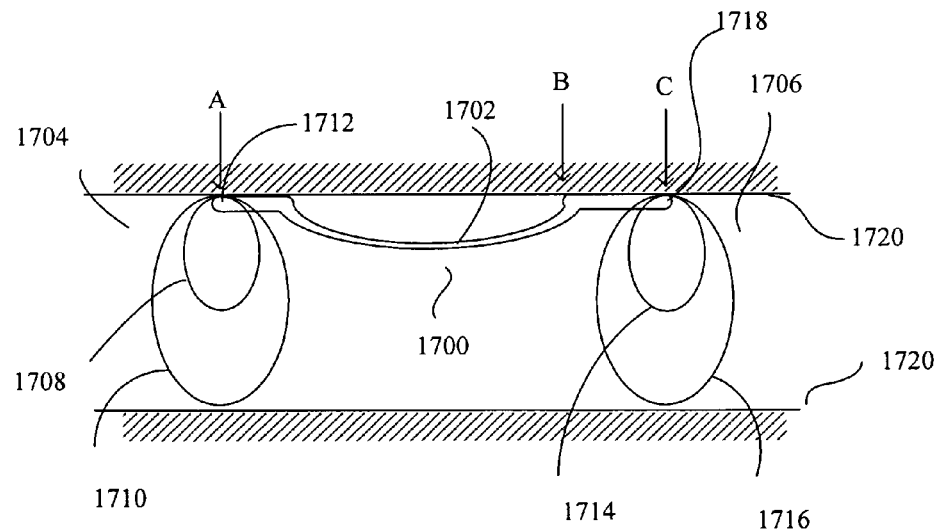

FIGS. 30A and 30B depict the use of shape-changing structure for engagement of a lumen wall and extension of a body structure of a lumen-traveling device. In FIG. 30A, lumen-traveling device 1700 includes shape-changing arc 1702, which may have a curved configuration, as shown in FIG. 30A, or an extended configuration as shown in FIG. 30B. Such a change in configuration may be produced by heating of a bimetallic strip, or by the use of a shape memory material having at least two configurations, and may be used to provide lengthening and shortening of lumen-traveling device 1700. Lumen-traveling device may include a first lumen-wall-engaging structure 1704 and second lumen-wall-engaging structure 1706. First lumen-wall-engaging structure 1704 is formed from a strip of material formed into first and second loops 1708 and 1710, respectively. In FIG. 30A, first loop 1708 is small, and second loop 1710 is large, so that it engages lumen walls 1720. Second lumen-wall-engaging structure 1706 is formed of first loop 1714 and second loop 1716, which in FIG. 30A are of medium size, so that neither engages lumen walls 1720. First lumen-wall-engaging structure 1704 is connected to lumen-traveling device 1700 at mounting point 1712, which includes a translational mechanism for moving first loop 1708 with respect to second loop 1712 to change the size of the two loops. Similarly, second lumen-wall-engaging structure 1706 is connected to lumen-traveling device 1700 at mounting point 1718, which includes a translational mechanism for moving first loop 1714 with respect to second loop 1716 to change the size of the two loops. In FIG. 30B, arc 1702 is extended, so that second lumen-wall-engaging structure 1706 has moved from point B (in FIG. 30A) to point C (in FIG. 30B). First loop 1714 of second lumen-wall-engaging structure 1706 has been reduced in size by a translational mechanism at mounting point 1718, while second loop 1716 has been increased in size to engage lumen walls 1720. Inchworm motion similar to that depicted in FIGS. 29A-29E can thus be produced by an embodiment of lumen-traveling device as depicted in FIGS. 30A and 30B.

Figure 31:
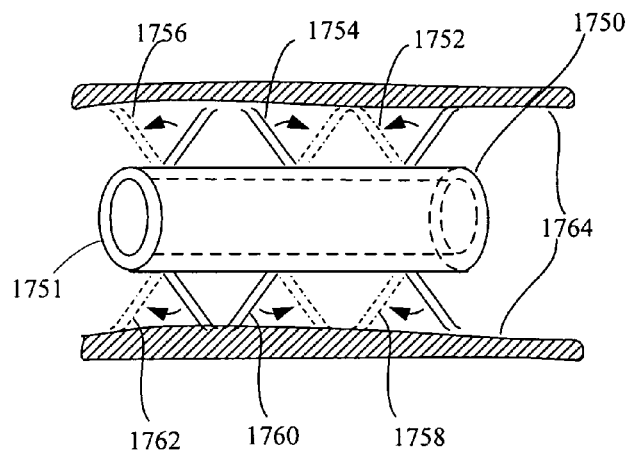
FIG. 31 illustrates a propelling mechanism of a lumen-traveling device.

FIG. 31 depicts a further embodiment of a lumen-traveling device adapted to travel through the body lumen with a propelling mechanism that produces walking-type motion. The lumen-traveling device may include two or more lumen-wall-engaging structures on a portion of the lumen-traveling device capable of at least intermittently engaging an inner surface of a body lumen in which the lumen-traveling device is deployed, wherein the propelling mechanism drives walking movement of the two or more lumen-wall-engaging structures with respect to inner surface of the body lumen. Lengthening and shortening of the distance between the lumen-wall-engaging structures is produced by change in leg configuration rather than by lengthening or shortening of the main structure (e.g. body structure) of the lumen-traveling device. Lumen-traveling device 1750 includes a structural element 1751 sized to fit within a body lumen; at least two lumen wall-engaging structures operable to alternately engage and disengage a wall of the body lumen (in FIG. 31, 6 lumen-wall-engaging structures 1752, 1754, 1756, 1758, 1760, and 1762 are shown); a propelling mechanism capable of producing relative extension and retraction of the at least two lumen-wall-engaging structures with respect to each other in combination with alternate engagement and disengagement of the body lumen wall 1764 to produce movement of the lumen-traveling stimulation device with respect to the body lumen wall. Lumen-traveling device 1750 may also include motion control circuitry carried at least in part by the lumen-traveling device and configured to control the propelling mechanism to control movement of the lumen-traveling device through the body lumen; a sensor capable of detecting a condition of interest in the body lumen; and an active portion carried by the structural element and configured to perform an action in response to detection of the condition of interest by the sensor, not shown in FIG. 31 but operating as described elsewhere herein. The at least two lumen-wall-engaging structures may include at least two appendages configured for walking motion. In the embodiment shown in FIG. 31, legs 1752 and 1754 extend and retract with respect to each other, for example, so that as one leg swings forward, the other swings back. Larger or smaller numbers of legs, distributed in various patterns about the structural element, may be used to propel the lumen-traveling device through the body lumen, and the embodiment depicted in FIG. 31 represents one possible example.

Leg structures for lumen-traveling devices may be formed of various materials and structures, including nanotubes and nanotube bundles, carbon fibers and carbon fiber bundles, silicon, metal, polymers, and other materials as described herein. Legs may be moved to produce walking motion may be actuated by various mechanisms. In some embodiments the legs formed from shape-changing material may be moved through change in configuration of the leg structure itself, while in other embodiments the leg may have a substantially rigid or fixed configuration that may be moved by separate actuation mechanism. Shape-changing materials that may be used in leg structures or actuators may be of various types, for example, stacked piezoelectric elements, electroactive polymers, heat sensitive polymers, magnetic field responsive polymers, and ferromagnetic materials, as described elsewhere herein. In some embodiments, motors and actuators may be used to drive leg motion, as known to those of skill in the art.

In another embodiment of a propelling mechanism, as depicted in FIGS. 32 and 32, multiple lumen-wall-engaging structures, operating in sequence to alternately engage and disengage the lumen wall, may be used to produce "peristaltic" motion of the lumen-traveling device. Examples of devices that produce this type of motion are described in U.S. Pat. No. 6,764,441; U.S. Patent Application 2006/0004395; MANGAN, ELIZABETH V.; KINGSLEY, DAN A.;

QUINN, ROGER D.; CHIEL, HILLEL J.; "Development of a Peristaltic Endoscope"; IEEE International Conference on Robotics & Automation 2002; pp. 1-6; located at http://biorobots.cwru.edu/publications/ICRA02_Mangan_Endoscope.pdf; and MEIER, P.; OBERTHÜR, S.; LANG, M.; "Development of a compliant device for minimally invasive surgery"; Proceedings of the 28$^{th}$ IEEE EMBS Annual International Conference; bearing dates of Aug. 30, 2006-Sep. 3, 2006 and 2006; pp. 331-334; IEEE; all of which are incorporated herein by reference.

Figure 32A:
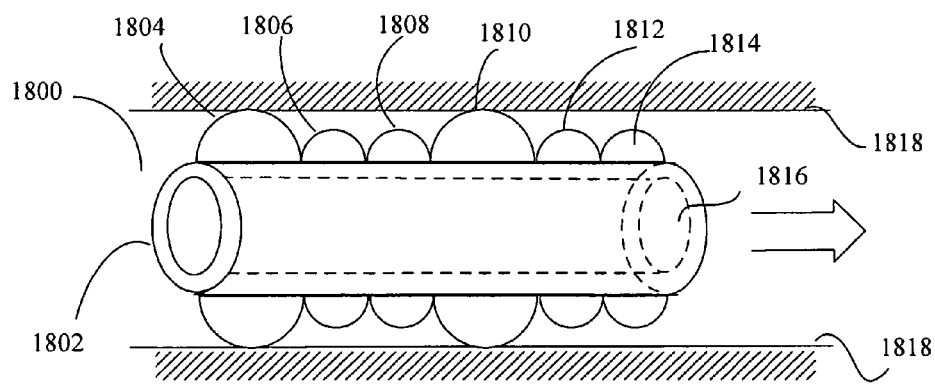
FIGS. 32A and 32B illustrate another embodiment of a propelling mechanism.
Figure 32B:
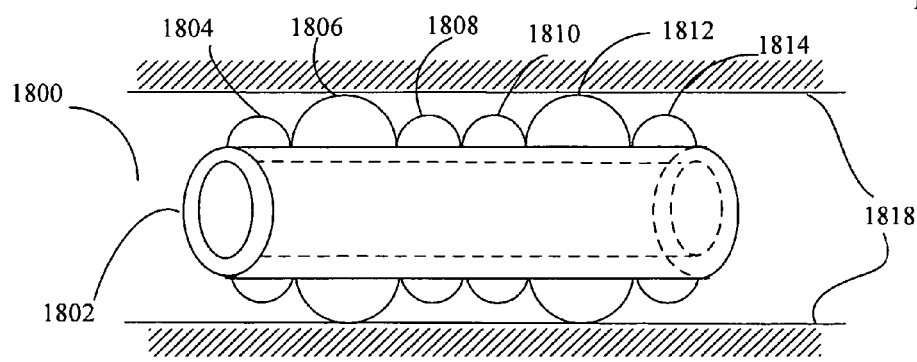

In FIGS. 32A and 32B, lumen-traveling device 1800 includes structural element 1802, which may be formed of a resilient material. Structural element 1802 may be a substantially tubular structure with a central lumen 1816, for example. A plurality of expanding or extending structures 1804, 1806, 1808, 1810, 1812, 1814, and 1818 may be positioned along the length of structural element 1802. Expanding or extending structures may expand in a lengthwise direction as well as expanding in a radially outward direction. For example, in FIG. 32A, expanding or extending structures 1804 and 1810 are shown in their expanded configurations, in which they are both wider and longer than in their contracted configurations as shown in FIG. 32B. Conversely, expanding or extending structures 1806, 1808, 1812, and 1814 are shown in the contracted configurations in FIG. 32A, and in their expanded configurations in FIG. 32B. By expanding and contracting the expanding or extending structures in sequence, as depicted in FIGS. 32A and 32B, movement of the lumen-traveling device through the body lumen may be accomplished.

Figure 33:
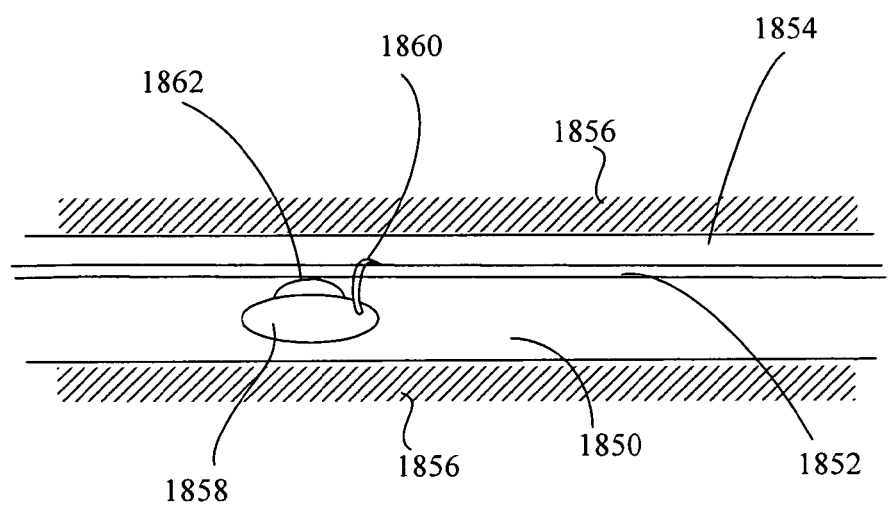
FIG. 33 illustrates another embodiment of a propelling mechanism.

In some embodiments, a propelling mechanism may be configured to drive movement of the lumen-traveling device along a wire, catheter, cannula, or tube within the body lumen. For example, as shown in FIG. 33, lumen-traveling device 1850 moves along elongated structure 1852 (which may be, for example, a wire, catheter, cannula, tube or other structure) located within body lumen 1854, surrounded by lumen walls 1856. Lumen-traveling device 1850 includes body structure 1858, retainer 1860, and propelling mechanism 1862. In the example depicted in FIG. 33, retainer 1860 is a hook-like structure that holds lumen-traveling device 1850 against elongated structure 1852 while allowing it to move along elongated structure 1852, while propelling mechanism 1862 causes lumen-traveling device 1850 to move along elongated structure 1852. In the embodiment of FIG. 33, propelling mechanism 1862 is a rotating wheel that moves lumen-traveling device 1850 along elongated structure 1852, but in other embodiment, other propelling mechanisms may be used to move a lumen-traveling device along an elongated structure.

Finally, as noted elsewhere herein, in some embodiments, the lumen-traveling device may be propelled through the body lumen by one or more paddles, propellers, vortex generators, jets, flagellum-like structures, or the like, which push against fluid contained within the lumen rather than engaging the wall of the body lumen, e.g. as described in U.S. Pat. No. 6,240,312 or in BEHKAM, BAHAREH; SITTI, METIN; "TOWARDS HYBRID SWIMMING MICROROBOTS: BACTERIA ASSISTED PROPULSION OF POLYSTYRENE BEADS"; Proceedings of the 28$^{th}$ IEEE EMBS Annual International Conference; bearing dates of Aug. 30, 2006-Sep. 3, 2006 and 2006; pp. 2421-2424; IEEE; CHRISTENSEN, BILL; "Propulsion System for 'Fantastic Voyage' Robot", bearing a date of Nov. 10, 2006, printed on Jan. 4, 2007, located at http://technovelgy.com/ct/Science-Fiction-News.asp?NewsNum=811; or "Researchers: Squid-Inspired Vortex Generators Could Mean Better Propulsion for Unmanned Underwater Vehicles"; UnderwaterTimes.com; Dec. 12, 2006; pp. 1-2; printed on Jan. 4, 2007; located at http://www.underwatertimes.com/print.php?article_id=51030782641; or MOHSENI, KAMRAN; "Biomimemetic & Bio-Inspired Aerial and Underwater Vehicles"; bearing a date of Sep. 23, 2006; pp. 1-100 printed on Jan. 4, 2007, located at http://enstrophy.colorado.edu/~mohseni/MicroVehicles1.html#UUV1#UUV1 all of which are incorporated herein by reference.

The direction of movement produced by the various propelling mechanisms described herein may be reversed by simply reversing the operation of the propelling mechanisms.

In various embodiments as described herein, a lumen-traveling device may include a power source configured to provide power to at least one of the propelling mechanism, the motion control circuitry, the sensor, the response initiation circuitry, and the active portion. The power source may be a battery or microbattery, a fuel cell or biofuel cell, or a nuclear battery. One or more power sources of the same or different types may be included in the lumen-traveling device, without limitation. Batteries may be located on the lumen-traveling device, possibly a microbattery like those available from Quallion LLC (http://www.quallion.com) or designed as a film (U.S. Pat. Nos. 5,338,625 and 5,705,293), which are incorporated herein by reference. Alternatively, the power source could be one or more fuel cell such as an enzymatic, microbial, or photosynthetic fuel cell or other biofuel cell (US2003/0152823A1; WO03/106966A2; or Chen T et al. J. Am. Chem. Soc. 2001, 123, 8630-8631, A Miniature Biofuel Cell, all of which are incorporated herein by reference), and could be of any size, including the micro- or nano-scale. In some embodiments, the power source may be a nuclear battery. The power source may be an energy-scavenging device such as a pressure-rectifying mechanism that utilizes pulsatile changes in blood pressure, for example, or an acceleration-rectifying mechanism as used in self-winding watches, or other types of flow-rectifying mechanism capable of deriving energy from other flow parameters. In some embodiments, the power source may be an electrical power source located remote from the structural element and connected to the structural element by a wire, or an optical power source located remote from the structural element and connected to the structural element by a fiber-optic line or cable. In some embodiments, the power source may be a power receiver capable of receiving power from an external source, for example, an acoustic source or electromagnetic source (e.g., infrared energy, or inductively coupled, as described in U.S. Pat. No. 6,170,485 or U.S. Patent Application No. 2005/0228259, which are incorporated herein by reference). In some embodiments, the power source may include an electrical power source located remote from the lumen-traveling device and connected to the lumen-traveling device by a wire, or an optical power source located remote from the lumen-traveling device and connected to the lumen-traveling device by an optical fiber.

In some embodiments, the lumen-traveling device may include a power transmitter capable of transmitting power from the lumen-traveling device to a secondary location. The power transmitter may be capable of transmitting at least one of acoustic power, electrical power, or optical power. The secondary location may be, for example, another device within the body, either in a body lumen or elsewhere, that includes a power receiver and structures for using, storing and/or re-transmitting the received power.

Figure 34:
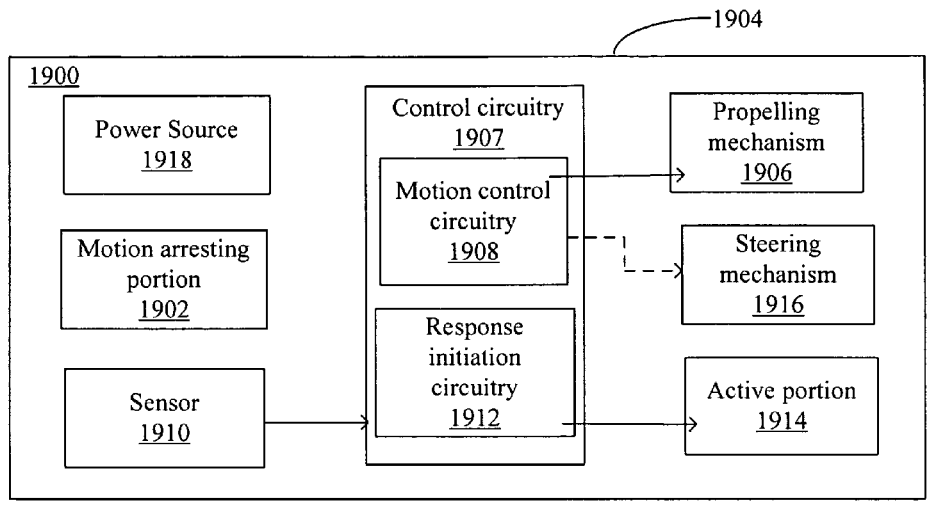
FIG. 34 is a schematic diagram of a lumen-traveling device.

FIG. 34 is a block diagram depicting a further embodiment of a lumen-traveling device 1900, which includes a motion-arresting portion 1902; a fluid-contacting portion 1904 configured to contact fluid within the body lumen and to at least intermittently permit flow of fluid through the body lumen; a propelling mechanism 1906 capable of producing movement of the lumen-traveling device through a body lumen in which the lumen-traveling device is deployed; motion control circuitry 1908 carried at least in part by said lumen-traveling device and configured to control propelling mechanism 1906 to control movement of the lumen-traveling device through the body lumen; a sensor 1910 capable of detecting a condition of interest in the body lumen and generating a sense signal indicating detection of the condition of interest; response initiation circuitry 1912 operatively connected to sensor 1910 and configured to generate a response initiation signal upon receipt of the sense signal indicating detection of a condition of interest in the body lumen; and an active portion 1914 operatively connected to response initiation circuitry 1912 and capable of producing a response upon receipt of the response initiation signal. Motion control circuitry 1908 and response initiation circuitry 1912 make up part of control circuitry 1907, which may also include other components not specifically described herein. The embodiment of FIG. 34 also includes a steering mechanism 1916 capable of modifying the direction of movement of the lumen-traveling device; wherein the motion control circuitry 1908 may be configured to control the steering mechanism 1916 to control movement of the lumen-traveling device through the body lumen. The embodiment of FIG. 34 may include power source 1918 configured to provide power to at least one of propelling mechanism 1906, steering mechanism 1916, motion control circuitry 1908, sensor 1910, response initiation circuitry 1912 and active portion 1914. Components of the embodiment of FIG. 34 may be generally as described elsewhere herein. Steering mechanism 1916 may be any of various structures, depending on the type of propelling mechanism used. If the propelling mechanism is a paddle or propeller that causes the lumen-traveling device to move in the fluid in the lumen, the steering mechanism may be a rudder. If the propelling mechanism includes multiple wheels or limb-like structures, they may be activated differentially on different sides of the lumen-traveling device to steer it in one direction or another. In embodiments in which the lumen-traveling device contacts the lumen walls on all sides of the device, the steering mechanism may be used only in the cases that the lumen-traveling device encounters a branch point in the lumen, and once the front portion of the device (defined by the direction of travel) is steered to cause the device to enter a selected branch, the back portion of the device will follow without the need for additional steering.

Various embodiments of the lumen-traveling device may include a marker or tag. The marker or tag may be an imaging marker or tag detectable by a remote imaging system to indicate the position of the lumen-traveling device within the body of a subject (for example, a radio-opaque marker for x-ray imaging). Alternatively, the marker or tag may be detectable by a sensing device or structure within the body of the subject.

Figure 35:
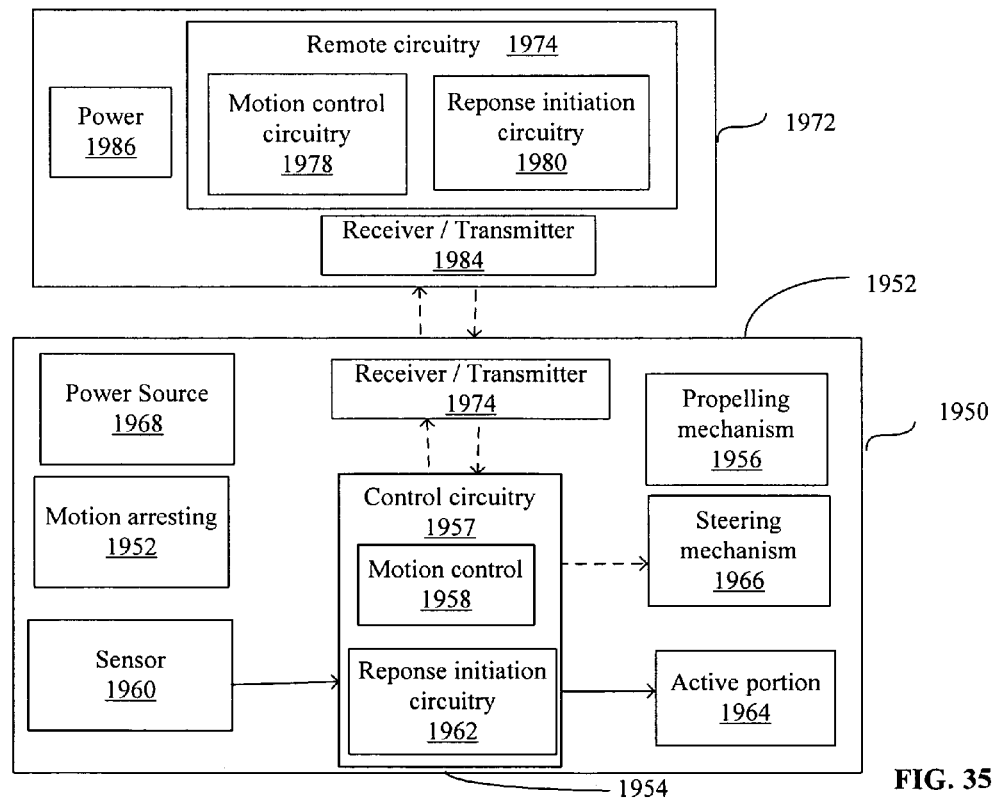
FIG. 35 is a schematic diagram of a lumen-traveling device including a remote portion.

In some embodiments, as depicted in FIG. 35, at least a portion of the circuitry that controls the operation of the lumen-traveling device 1950 may be located remote from the lumen-traveling device in remote device portion 1972, outside the body of the subject as shown in FIG. 28, or at a location within the body of the subject at a distance from the lumen-traveling device. In the embodiment of FIG. 35, lumen-traveling device 1950 includes a motion-arresting portion 1952; a fluid-contacting portion 1954 configured to contact fluid within the body lumen and to at least intermittently permit flow of fluid through the body lumen; a propelling mechanism 1956 capable of producing movement of the lumen-traveling device through a body lumen in which the lumen-traveling device is deployed; motion control circuitry 1958 carried at least in part by said lumen-traveling device and configured to control propelling mechanism 1956 to control movement of the lumen-traveling device through the body lumen; a sensor 1960 capable of detecting a condition of interest in the body lumen and generating a sense signal indicating detection of the condition of interest; response initiation circuitry 1962 operatively connected to sensor 1960 and configured to generate a response initiation signal upon receipt of the sense signal indicating detection of a condition of interest in the body lumen; and an active portion 1964 operatively connected to response initiation circuitry 1962 and capable of producing a response upon receipt of the response initiation signal. The embodiment of FIG. 35 includes a steering mechanism 1966 capable of modifying the direction of movement of the lumen-traveling device; wherein the motion control circuitry 1958 may be configured to control the steering mechanism 1966 to control movement of the lumen-traveling device through the body lumen. At least a portion of the control circuitry for lumen-traveling device 1950, remote circuitry 1974, may be located remote from lumen-traveling device 1950 in remote portion 1972. Remote circuitry 1974 may include a remote portion of the motion control circuitry 1978 and remote portion of the response initiation circuitry 1980. Lumen-traveling device 1950 may include receiver/transceiver 1984 that may include data reception and/or transmission circuitry configured to receive a wireless control signal from the remote portion of the motion control circuitry 1978, transmitted from transceiver 1984. Data may be transmitted from lumen-traveling device 1950 to remote portion 1972. Remote portion 1972 may include a power source 1986. Alternatively, the motion control circuitry may be located in or on the lumen-traveling device. The embodiment of FIG. 35 may include power source 1968 configured to provide power to at least one of propelling mechanism 1956, steering mechanism 1966, motion control circuitry 1958, sensor 1960, response initiation circuitry 1962 and active portion 1964. Components of the embodiment of FIG. 35 may be generally as described elsewhere herein. Steering mechanism 1966 may be as described above in connection with FIG. 34. In some embodiments, power may be transmitted to lumen-traveling device 1950 from remote portion 1972.

The motion control circuitry may be operatively connected to the sensor, and configured to control at least one of steering mechanism and propelling mechanism to control the movement of the lumen-traveling device at least in part in response to receipt of the sense signal indicating detection of the condition of interest in the body lumen. Similarly, the response initiation circuitry may be located in or on the lumen-traveling device in some embodiments, while in other embodiments at least a portion of the response initiation circuitry may be located remote from the lumen-traveling device, wherein the lumen-traveling device may include data transmission and reception circuitry configured for communicating with the at least a portion of the response initiation circuitry located remote from the lumen-traveling device.

The control circuitry for the lumen-traveling device, located either on the lumen-traveling device or in a remote portion, and including response initiation circuitry and/or motion control circuitry, may include a microprocessor, and/or at least one of hardware, software, and firmware. Examples of devices and/or systems for communicating within devices in the body are provided in U.S. Pat. No. 5,843,139; 6,409,674; or 7,125,382; U.S. Patent Application 2002/0198604, and RICE, MIKE; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725, all of which are incorporated herein by reference in their entirety.

Various embodiments of lumen-traveling devices as depicted and described herein may include a lumen-wall-engaging portion; a fluid-contacting portion configured to contact fluid within the body lumen and to at least intermittently permit flow of fluid through the body lumen; a propelling mechanism capable of producing movement of the lumen-traveling device through a body lumen in which the lumen-traveling device may be deployed; at least one sensor capable of detecting a condition of interest in the body lumen and generating a sense signal indicating detection of the condition of interest; motion control circuitry carried at least in part on said lumen-traveling device and configured to control the propelling mechanism at least in part based upon the sense signal; response initiation circuitry operatively connected to the sensor and configured to generate a response initiation signal upon receipt of the sense signal indicating detection of a condition of interest in the body lumen; and an active portion operatively connected to the response initiation circuitry and capable of producing a response upon receipt of the response initiation signal. A fluid contacting portion configured to contact fluid within the body lumen and at least intermittently permit flow of fluid through the body lumen is though to be a useful feature for lumen-traveling device used in lumens through which fluid travel, such as, for example, blood vessels, portions of the respiratory tract, digestive tract or CSF space. In some cases, blockage of flow may cause serious problems. Thus, lumen-traveling devices which are configured to permit the flow of fluid at least a portion of the time may be of value. For example, fluid may flow through a channel or lumen passing through the lumen-traveling device (e.g., as depicted in FIG. 1, 29, or 32), or past a lumen-traveling device that has an cross section that does not fill the cross-section of the lumen, as in FIG. 5A, 5E, 30A, 30B, or 33, for example.

As shown in various of the figures, a lumen-traveling device may include a power source configured to provide power to at least one of the propelling mechanism, the motion control circuitry, the sensor, the response initiation circuitry, and the active portion. The power source may be located on the lumen-traveling device, or (at least in part) on a remote portion as illustrated in FIG. 35, with power being transmitted to the lumen-traveling device.

A lumen-traveling device may include various types of sensing or information gathering devices or structures. A lumen-traveling device may include one or multiple sensors of the same or different types, which may include but are not limited to, pressure sensors, temperature sensors, flow sensors, viscosity sensors, shear sensors (e.g., for measuring the effective shear modulus of the fluid at a frequency or strain-rate), pH sensors, chemical sensors for determining the concentration of a chemical compound or species, optical sensors, acoustic sensors, biosensors, electrical sensors, magnetic sensors, clocks or timers. Examples of a variety of sensor which may be used in embodiments as described herein are provided in U.S. Pat. Nos. 5,522,394; 5,873,835; 6,053,837; 6,409,674; 6,111,520; 6,278,379; 6,475,639; 6,855,115, and U.S. Patent Applications 2005/0277839 and 2005/0149170, all of which are incorporated herein by reference. U.S. Pat. No. 6,802,811, which is included herein by reference, provides additional examples of sensing and/or monitoring. In some embodiments, an imaging device (e.g., a CCD array) may be operatively connected to lumen-traveling device, e.g. connected to the structural element.

An optical sensor may be configured to measure the optical absorption, optical emission, fluorescence, or phosphorescence of at least a portion of the fluid, for example. Such optical properties may be inherent optical properties of all or a portion of the fluid or tissue, or may be optical properties of materials added or introduced to the fluid, such as tags or markers for materials of interest. Optical sensing of materials in blood is described, for example, in KRUEGER, CURTIS; "New light on blood testing"; Oct. 20, 2006; pp. 1-2; St. Petersburg Times; printed on Dec. 24, 2006; located at http://www.sptimes.com/2006/10/20news_pf/Tampabay/New_light_on_blood_te.shtml, which is incorporated herein by reference.

A biosensor may detect materials including, but not limited to, a biological marker, an antibody, an antigen, a peptide, a polypeptide, a protein, a complex, a nucleic acid, a cell (and, in some cases, a cell of a particular type, e.g. by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, or a tag. A biosensor may include an antibody or other binding molecule such as a receptor or ligand. As used herein a sensor may include a single sensor or an array of sensors, and is not limited to a particular number or type of sensors. A sensor might comprise, in part or whole, a gas sensor such as an acoustic wave, chemiresistant, or piezoelectric sensor, or perhaps an electronic nose. A sensor may be very small, comprising a sensor or array that is a chemical sensor ("Chemical Detection with a Single-Walled Carbon Nanotube Capacitor," Snow, E. S., Science, Vol. 307, pp. 1942-1945, 2005), a gas sensor ("Smart single-chip gas sensor microsystem," Hagleitner, C. et al., Nature, Vol. 414, pp. 293-296, 2001), an electronic nose, a nuclear magnetic resonance imager ("Controlled multiple quantum coherences of nuclear spins in a nanometer-scale device", Go Yusa, 2005, Vol. 343: pp. 1001-1005, Nature). The foregoing references are incorporated herein by reference. Further examples of sensors are provided in The Biomedical Engineering Handbook, Second Edition, Volume I, J. D. Bronzino, Ed., Copyright 2000, CRC Press LLC, pp. V-1-51-9, and U.S. Pat. No. 6,802,811, both of which are incorporated herein by reference.

A sensor may be configured to measure various parameters, including, but not limited to, the electrical resistivity of fluid, tissue, or other material, the density or sound speed of a material, the pH, the osmolality, or the index of refraction of the fluid at least one wavelength. The selection of a suitable sensor for a particular application or use site is considered to be within the capability of a person having skill in the art. In some embodiments, a sensor may include some signal processing or pre-processing capability integrated therewith.

The condition of interest detected by the sensor may include an anatomical feature (for example, a branching point) that indicates proximity to a treatment target, or indicates the presence of the treatment target itself. The condition of interest may include a man-made structure, such as an implantable device of some sort, potentially including another lumen-traveling device. Alternatively, the condition of interest may include one or more of an electrical field, magnetic field, temperature, flow condition, time, location, pressure, pH, presence or concentration of a chemical compound or species.

A sensor may sense a wide variety of physical or chemical properties. In some embodiments, detecting a condition of interest may include detecting the presence (or absence) of a material or structure of interest.

In some applications, detecting a condition of interest in the fluid within the body lumen may include detecting the presence of a material of interest in the fluid within the body lumen. A material of interest in a fluid may include, for example, an object such as a blood clot, a thrombus, an embolus, a plaque, a lipid, a kidney stone, a dust particle, a pollen particle, an aggregate, a cell, a specific type of cell, a cell fragment, a cellular component, a platelet, an organelle, a collection or aggregation of cells or components thereof, a gamete, a pathogen, or a parasite.

Lumen-traveling devices may be used in a number of different ways. In some embodiments, a lumen-traveling device may travel through the lumen performing an action at selected locations that are identified as the device travels through the lumen. A device may move through the body lumen performing "surveillance" for periods of time ranging from a few minutes, to hours, days, weeks, or years. When the lumen-traveling device identifies a location of interest (e.g., a location where some sort of medical treatment is needed), it may perform an action, which may include delivering a medical treatment, transmitting a signal indicating the need for medical treatment to a monitoring system, or recording information about the location of interest, for example. A lumen-traveling device performing surveillance in a body lumen may perform an action "on the fly" as it moves past the location of interest, or it may pause or cease moving at or near a location of interest in order to perform an action.

Sensors in combination with logic circuitry (hardware, firmware, and/or software) may be used to detect a condition of interest in or on the wall of the body lumen, in the tissue that forms or surrounds the body lumen, or in the fluid within the body lumen. A location of interest in a body lumen may include a location of anatomical interest (e.g., a branching point), a location near an organ, a tumor, an injury, etc, a diseased or damaged region (e.g. a fistula or aneurysm), area of scar tissue, a polyp, a blockage or constriction formed by a bacterial plaque, blood clot, or vasospasm, for example. Locations of interest may be detected by the detection of chemical markers or fingerprints, by altered mechanical, optical, thermal, electrical or acoustic properties, by imaging, and by other detection methods as known to those of skill in the art. The lumen-traveling device may perform one or more actions with an active portion in response to detection of a location of interest. Tissue condition can be detected with the use of pressure pulses, as described in U.S. Pat. No. 6,170,488 and U.S. Patent Applications 2003/0220556 and 2004/0225325, all of which are incorporated herein by reference.

In some embodiments, a lumen-traveling device may perform an action continuously or intermittently as it moves through a body lumen. Performance of the action may not necessarily always be associated with detection of a region of interest within a body lumen.

In some embodiments, a lumen-traveling device may move through a body lumen until it reaches a particular location and then cease traveling in order to reside, either temporarily or substantially permanently, at the location. At the location, it may perform an action on the local tissue forming the lumen or perform an action on fluid within the lumen, which may be flowing or moving in some other manner, either continuously or intermittently, or may be substantially unmoving. The location at which a lumen-traveling device stops and resides may be pre-selected, in which case the device may be targeted to the location. Alternatively, the location may be selected as the device is traveling through the lumen, based on one or more features of the location, which may be sensed by the device. Features of the location may include, but are not limited to, indicators of injuries, pathologies or disease conditions to be treated by the device, or anatomical characteristics (size, proximity to an organ or other structure, etc.) that make the location a suitable site for the device to be positioned. Features of locations of interest may include chemical, thermal, mechanical, optical, or other properties as may be sensed with various types of sensors as described elsewhere herein. A parameter may be measured at a single point in time/space or may be measured over multiple dimensions (spatial, temporal, or other—e.g. frequency) to generate an image of a region that may include features of interest. Signal processing to perform analysis of the signal or image may be used to detect features/locations of interest from signal or image.

In one application, a lumen-traveling device traveling within the male reproductive tract may detect pH, flow, or viscosity of semen, for example, and based upon the value of the detected parameter, may perform an action to alter it to either enhance fertility or provide contraception.

In some embodiments, the lumen-traveling device may be used to deliver treatment to a location that is relatively inaccessible by other means. For example, a lumen-traveling device may move through vasculature within the brain in order to access brain regions for delivery of drugs, therapeutics, chemotherapy agents, chemical, mechanical, optical, electrical or magnetic stimuli, etc.

Figure 36:
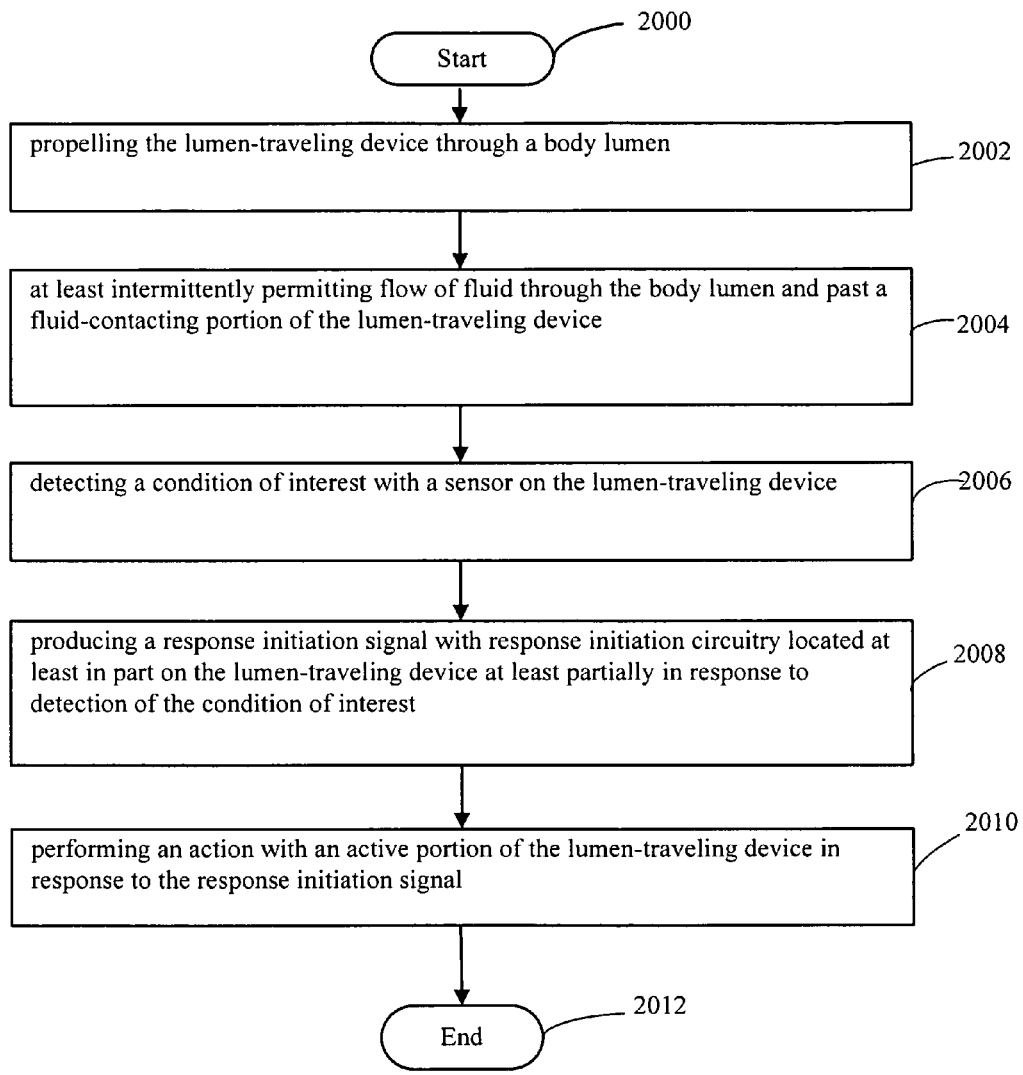
FIG. 36 is flow diagram of a method implemented with a lumen-traveling device.

FIG. 36 shows steps of a method implemented with a lumen-traveling device. The method steps include propelling the lumen-traveling device through a body lumen at step 2002; at least intermittently permitting flow of fluid through the body lumen and past a fluid-contacting portion of the lumen-traveling device at step 2004; detecting a condition of interest with a sensor on the lumen-traveling device at step 2006; producing a response initiation signal with response initiation circuitry located at least in part on the lumen-traveling device at least partially in response to detection of the condition of interest at step 2008; and performing an action with an active portion of the lumen-traveling device in response to the response initiation signal at step 2010.

Figure 37:
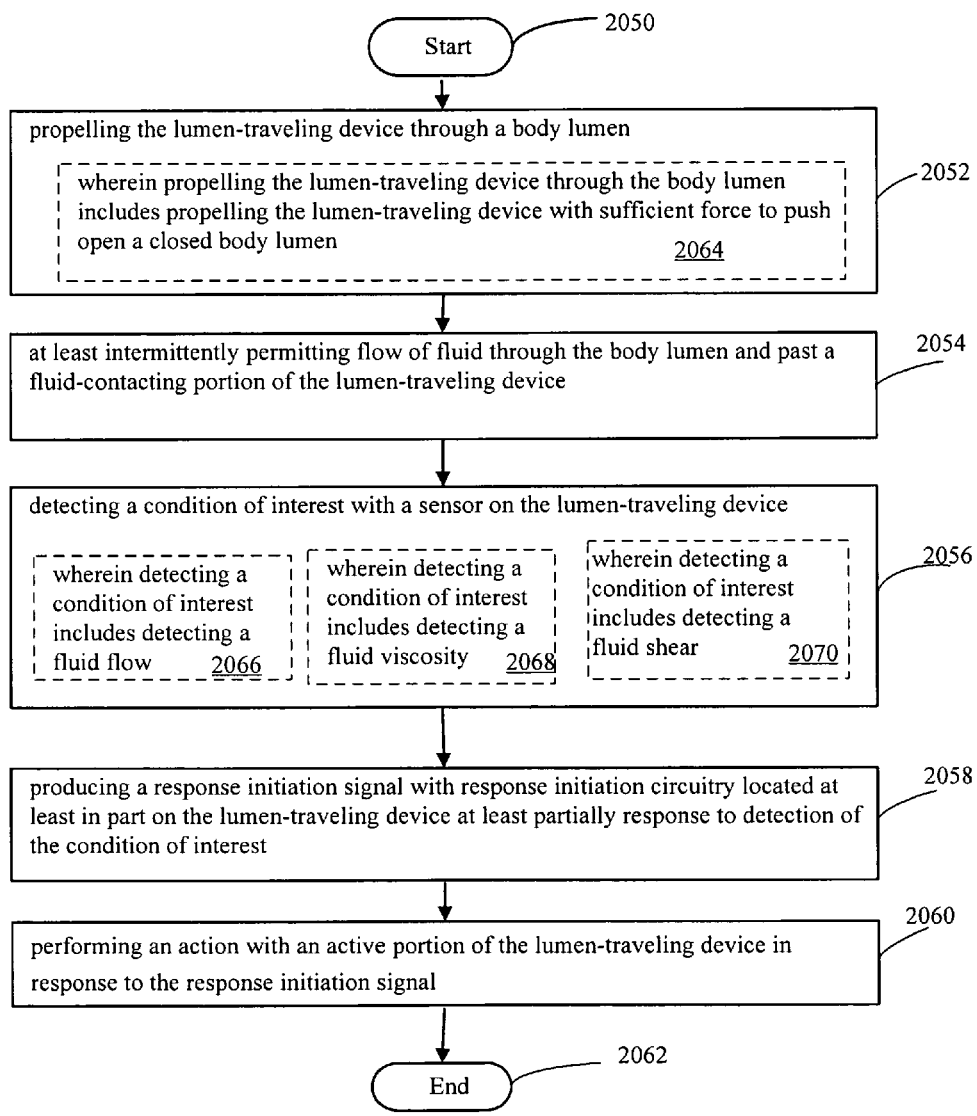
FIG. 37 is flow diagram of a further method implemented with a lumen-traveling device.

FIG. 37 shows further variants of the method of FIG. 36. The method may include propelling the lumen-traveling device through a body lumen at step 2052; at least intermittently permitting flow of fluid through the body lumen and past a fluid-contacting portion of the lumen-traveling device at step 2054; detecting a condition of interest with a sensor on the lumen-traveling device at step 2056; producing a response initiation signal with response initiation circuitry located at least in part on the lumen-traveling device at least partially in response to detection of the condition of interest at step 2058; and performing an action with an active portion of the lumen-traveling device in response to the response initiation signal at step 2060. In addition, propelling the lumen-traveling device through the body lumen may include propelling the lumen-traveling device with sufficient force to push open a closed body lumen, as shown in step 2064. The step of detecting a condition of interest may include detecting a fluid flow, as shown in step 2066, detecting fluid viscosity as shown in step 2068, or detecting a fluid shear, as shown in step 2070.

Figure 38:
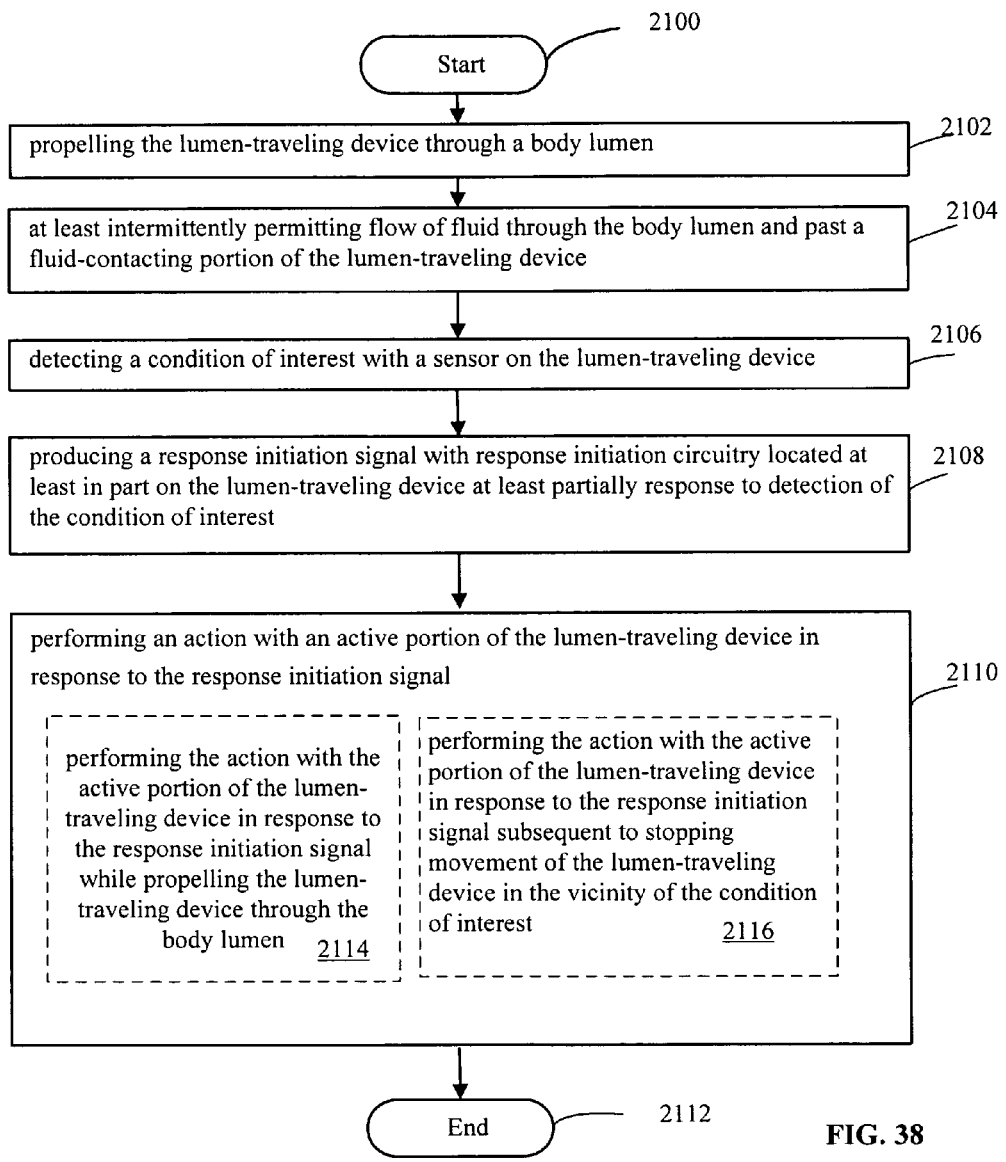
FIG. 38 is flow diagram of a further method implemented with a lumen-traveling device.

FIG. 38 shows further variants of the method of FIG. 36. Again, the method may include propelling the lumen-traveling device through a body lumen at step 2102; at least intermittently permitting flow of fluid through the body lumen and past a fluid-contacting portion of the lumen-traveling device at step 2104; detecting a condition of interest with a sensor on the lumen-traveling device at step 2106; producing a response initiation signal with response initiation circuitry located at least in part on the lumen-traveling device at least partially in response to detection of the condition of interest at step 2108; and performing an action with an active portion of the lumen-traveling device in response to the response initiation signal at step 2110. In addition, the method may include performing the action with the active portion of the lumen-traveling device in response to the response initiation signal while propelling the lumen-traveling device through the body lumen, as shown in step 2114. Alternatively, the method may include performing the action with the active portion of the lumen-traveling device in response to the response initiation signal subsequent to stopping movement of the lumen-traveling device in the vicinity of the condition of interest, as shown in step 2116.

Figure 39A:
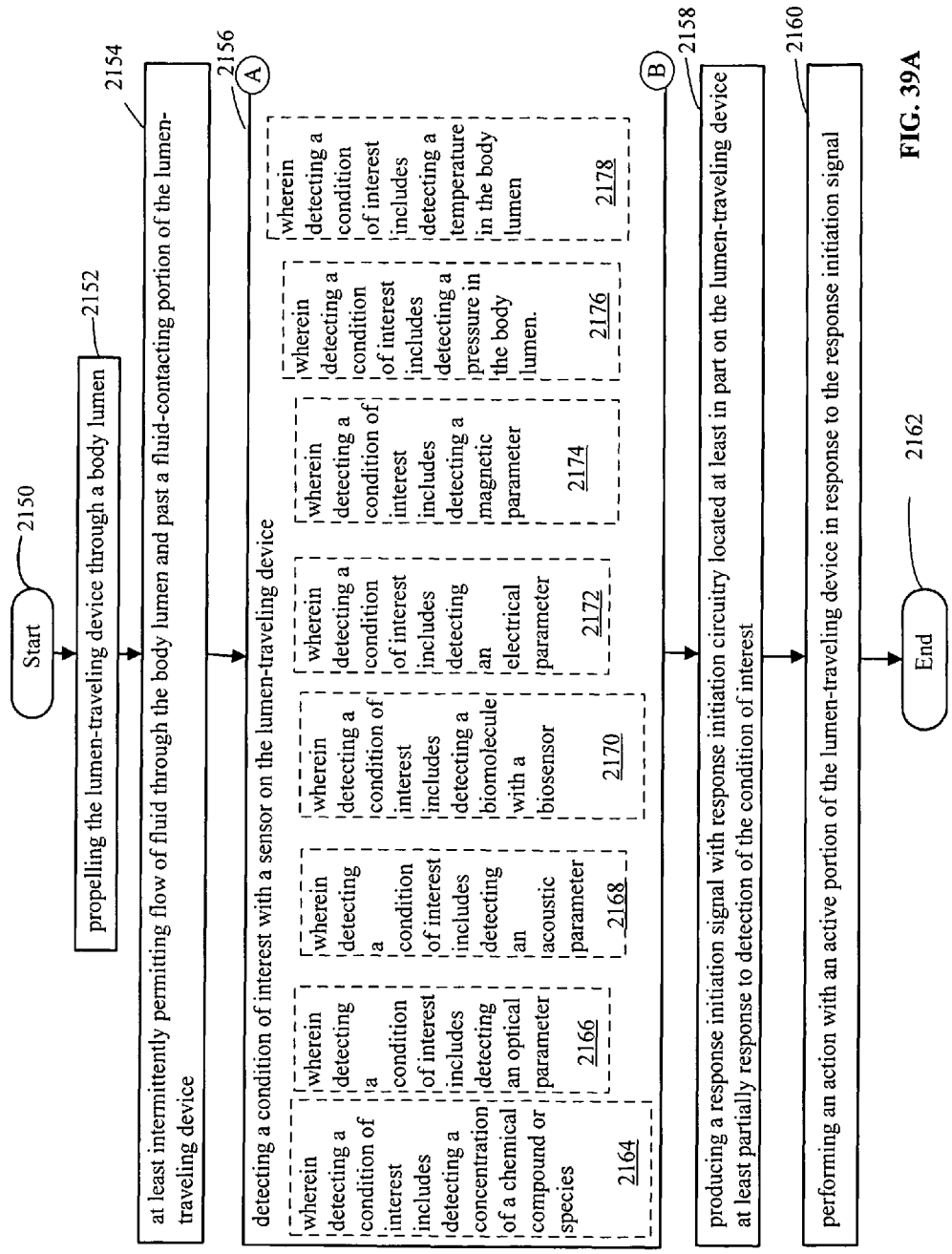
FIGS. 39A and 39B form a flow diagram showing several variants of a method implemented with a lumen-traveling device.
Figure 39B:
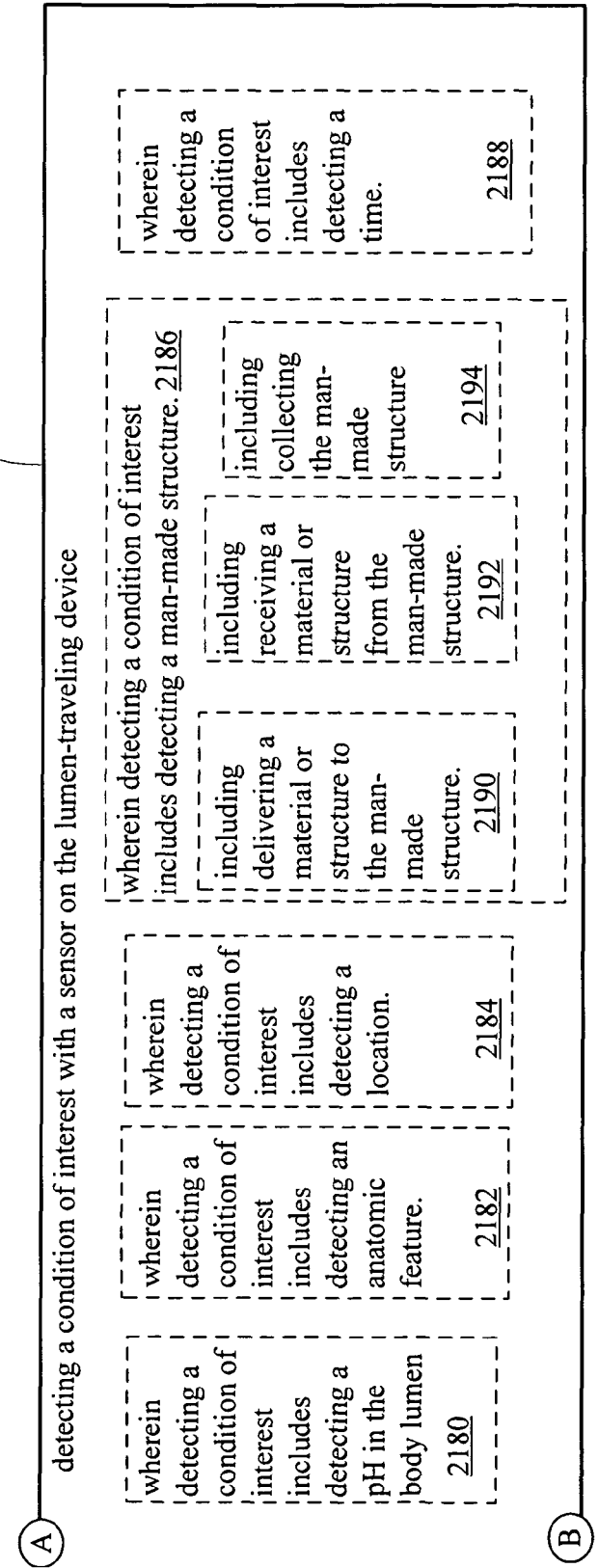

FIGS. 39A and 39B show further variations of the method of FIG. 36. The basic steps of the method include propelling the lumen-traveling device through a body lumen at step 2152; at least intermittently permitting flow of fluid through the body lumen and past a fluid-contacting portion of the lumen-traveling device at step 2154; detecting a condition of interest with a sensor on the lumen-traveling device at step 2156; producing a response initiation signal with response initiation circuitry located at least in part on the lumen-traveling device at least partially in response to detection of the condition of interest at step 2158; and performing an action with an active portion of the lumen-traveling device in response to the response initiation signal at step 2160. Detecting a condition of interest with a sensor on the lumen-traveling device may include detecting a concentration of a chemical compound or species (at step 2164), detecting an optical parameter (at step 2166), detecting an acoustic parameter (at step 2168), detecting a biomolecule with a biosensor (at step 2170), detecting an electrical parameter (at step 2172), detecting a magnetic parameter (at step 2174), detecting a pressure in the body lumen (at step 2176), or detecting a temperature in the body lumen (at step 2178), as shown in FIG. 39A, or, as shown in FIG. 39B, detecting a pH in the body lumen (at step 2180), detecting an anatomic feature (at step 2182), detecting a location (at step 2184), detecting a man-made structure (at step 2186), or detecting a time (at step 2188). If a man-made structure is detected, as at step 2186, the method may include the steps of delivering a material or structure to the man-made structure (at step 2190), receiving a material or structure from the man-made structure (at step 2192), or collecting the man-made structure (at step 2194). This may, for example, involve connecting to the man-made structure so that it can be pushed or pulled by the lumen-traveling device, or may involve taking up the man-made structure to be contained in or carried within the lumen-traveling device.

Figure 40A:
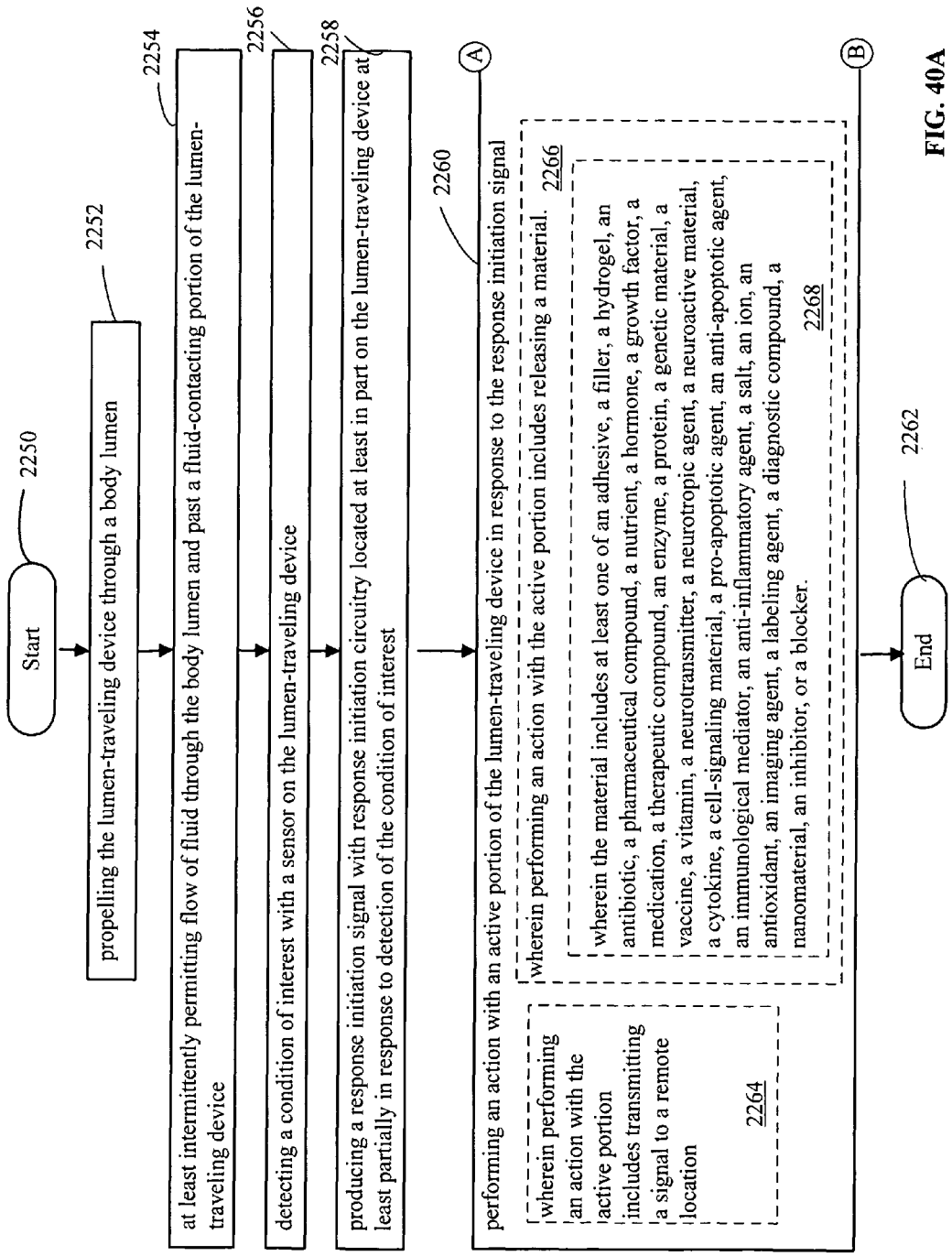

Steps 40A-40E show further variants of a method as described generally in FIG. 36. Again, the method may include propelling the lumen-traveling device through a body lumen at step 2252; at least intermittently permitting flow of fluid through the body lumen and past a fluid-contacting portion of the lumen-traveling device at step 2254; detecting a condition of interest with a sensor on the lumen-traveling device at step 2256; producing a response initiation signal with response initiation circuitry located at least in part on the lumen-traveling device at least partially in response to detection of the condition of interest at step 2258; and performing an action with an active portion of the lumen-traveling device in response to the response initiation signal at step 2260. As shown in FIG. 40A, the step of performing an action with the active portion (at step 2260) may include transmitting a signal to a remote location (at 2264), releasing a material (at step 2266), which may be, for example, at least one of an adhesive, a filler, a hydrogel, an antibiotic, a pharmaceutical compound, a nutrient, a hormone, a growth factor, a medication, a therapeutic compound, an enzyme, a protein, a genetic material, a cell, a fraction of a cell, a vaccine, a vitamin, a neurotransmitter, a neurotropic agent, a neuroactive material, a cytokine, a cell-signaling material, a pro-apoptotic agent, an anti-apoptotic agent, an immunological mediator, an anti-inflammatory agent, a salt, an ion, an antioxidant, an imaging agent, a labeling agent, a diagnostic compound, a nanomaterial, an inhibitor, or a blocker (as indicated at step 2268). Alternatively, as shown in FIG. 40B, performing an action with the active portion may include collecting a material from the body lumen (as shown in step 2270), which may include collecting a sample from a fluid within the body lumen (as shown in step 2272), or collecting a sample from a wall region of the body lumen (as shown in step 2274). Alternatively, the method may include collecting a sample from beyond the wall region of the body lumen, e.g., with the use of a needle to penetrate the body lumen wall and/or utilizing a permeation enhancer.

In some versions of the method, as shown in FIG. 40B, performing an action with the active portion may include producing heating or cooling, as shown in steps 2276 and 2282, respectively. Heating may be used in a variety of locations, for a variety of purposes. In one example, the method may include propelling the lumen-traveling device through the body lumen to a location in the vicinity of the preoptic area, wherein performing an action with the active portion may include producing heating in the vicinity of the preoptic area, as shown in step 2278. In another example, heating may be used in the male reproductive system to destroy gametes, as shown in step 2280. In another example (not shown), heating may be used for ablation of tissue. In addition, or alternatively, performing an action with the active portion may include securing the lumen-traveling device into position within the body lumen as shown in step 2284, e.g., by using various positioning or lumen-wall-engaging structures.

Figure 40C:
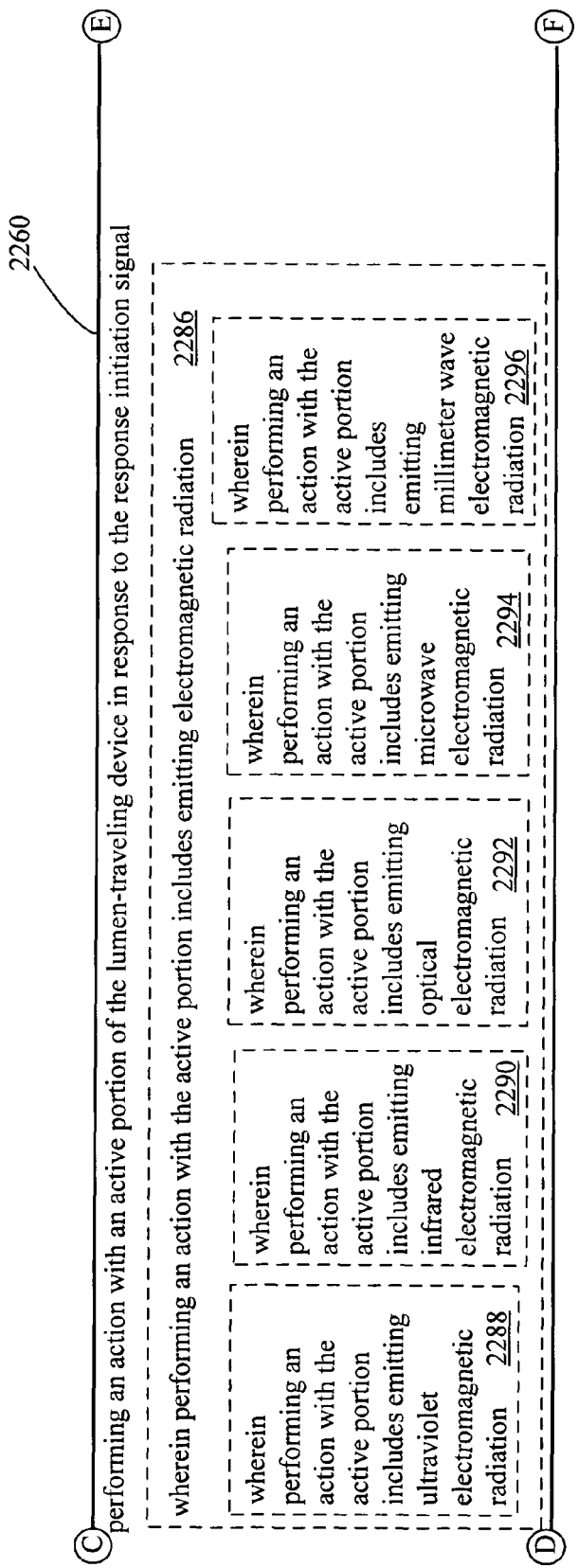
Figure 40D:
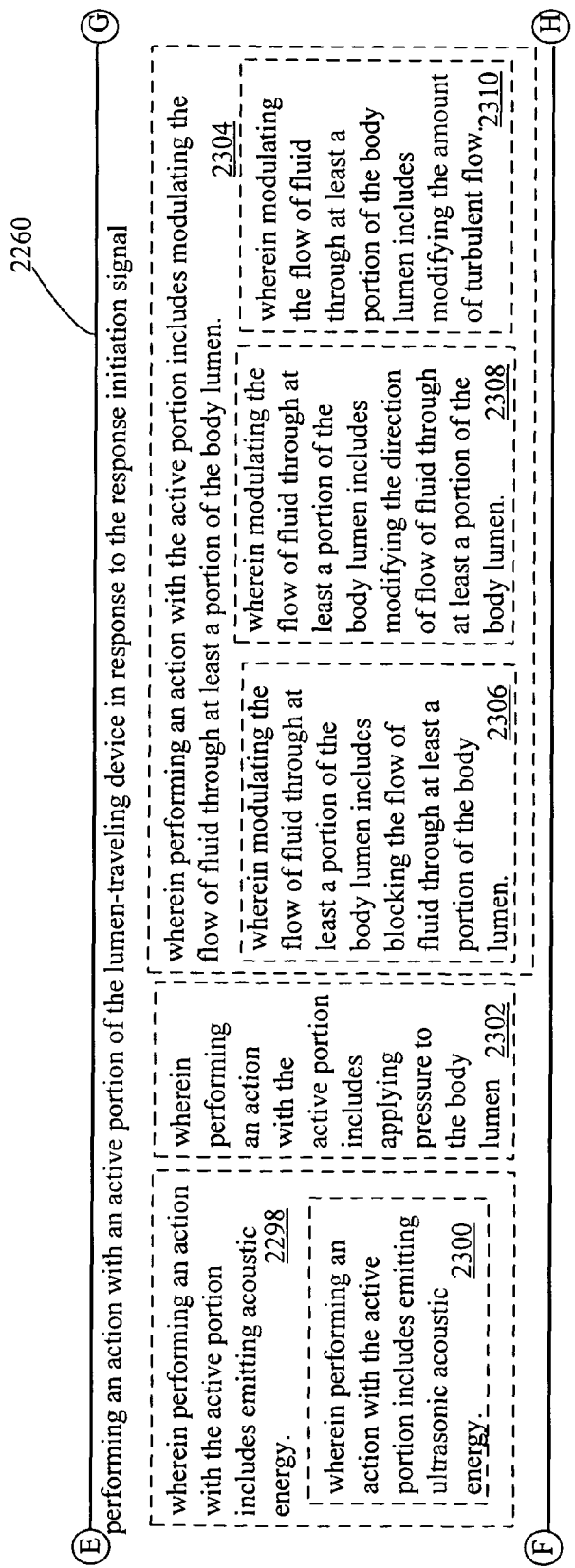

As shown in FIG. 40C, in some embodiments, performing an action with the active portion may include emitting electromagnetic radiation, as shown at step 2286. The action may include emitting ultraviolet, infrared, optical, microwave, or millimeter wave electromagnetic radiation, as indicated at steps 2288, 2290, 2292, 2294, and 2296, respectively. Alternatively, as shown in step 2298 of FIG. 40D, performing an action with the active portion may include emitting acoustic energy, including, but not limited to, ultrasonic acoustic energy, as indicated in step 2300. As shown in FIG. 40D, performing an action with the active portion may include applying pressure to the body lumen (step 2302), by expansion of the active portion, or by release of a gas or fluid. In other embodiments, performing an action with the active portion may include modulating the flow of fluid through at least a portion of the body lumen, as shown at step 2304, for example by blocking the flow of fluid through at least a portion of the body lumen (step 2306), modifying the direction of flow of fluid through at least a portion of the body lumen (2308), or modifying the amount of turbulent flow (step 2310). Modifying the direction of flow of fluid may include directing flow, toward a particular region and/or into a particular branch of a branching lumen, for example, with the use of various flow-directing structures as disclosed herein. Modifying the direction of flow of fluid may also include reversing the direction of flow, which may be accomplished, for example, by modifying the pressure within the lumen, as described herein.

Figure 40E:
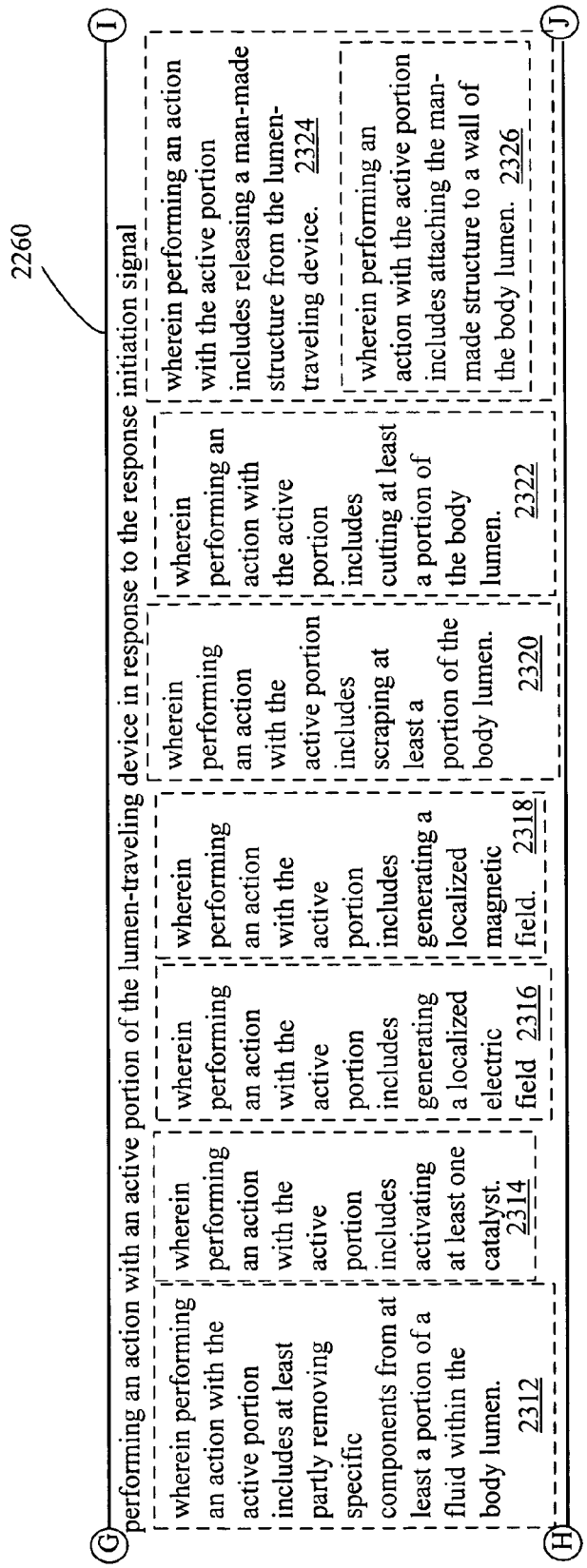
Figure 40F:
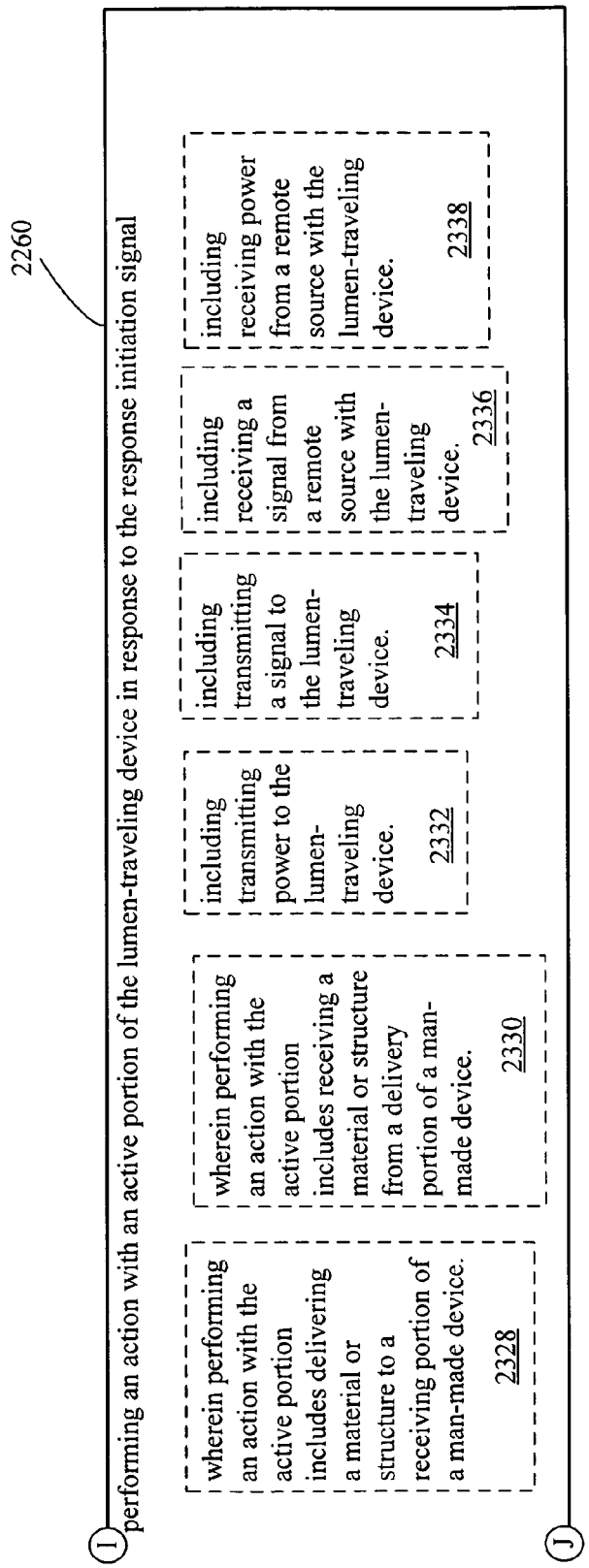

As shown in FIG. 40E, in some embodiments, performing an action with the active portion at step 2260 may include at least partly removing specific components from at least a portion of a fluid within the body lumen, as shown at step 2312, or activating at least one catalyst, as shown at step 2314. In still other embodiments, performing an action with the active portion may include generating an electric field, as shown at step 2316, generating a magnetic field, as shown at step 2318, or scraping or cutting at least a portion of the body lumen, as indicated at steps 2320 and 2322, respectively. Performing an action with the active portion may include releasing a man-made structure from the lumen-traveling device, as shown at step 2324, and, in some embodiments, attaching the man-made structure to a wall of the body lumen, as shown at step 2326. As shown in FIG. 40F, performing an action with the active portion at step 2260 may include delivering a material or structure to a receiving portion of a man-made device, as shown at 2328, receiving a material or structure from a delivery portion of a man-made device, as shown at 2330. Finally, the method may include one or more of transmitting power to the lumen-traveling device, as shown in step 2332, transmitting a signal to the lumen-traveling device, as shown in step 2334, receiving a signal from a remote source with the lumen-traveling device, as shown in step 2336, or receiving power from a remote source with the lumen-traveling device, as shown in step 2338.

A lumen-traveling device as described herein may include control circuitry for controlling various aspects of the operation of the device. Lumen-traveling devices and systems as described herein may be operated under the control of control circuitry, which may include hardware, software, firmware, or a combination thereof.

Figure 41:
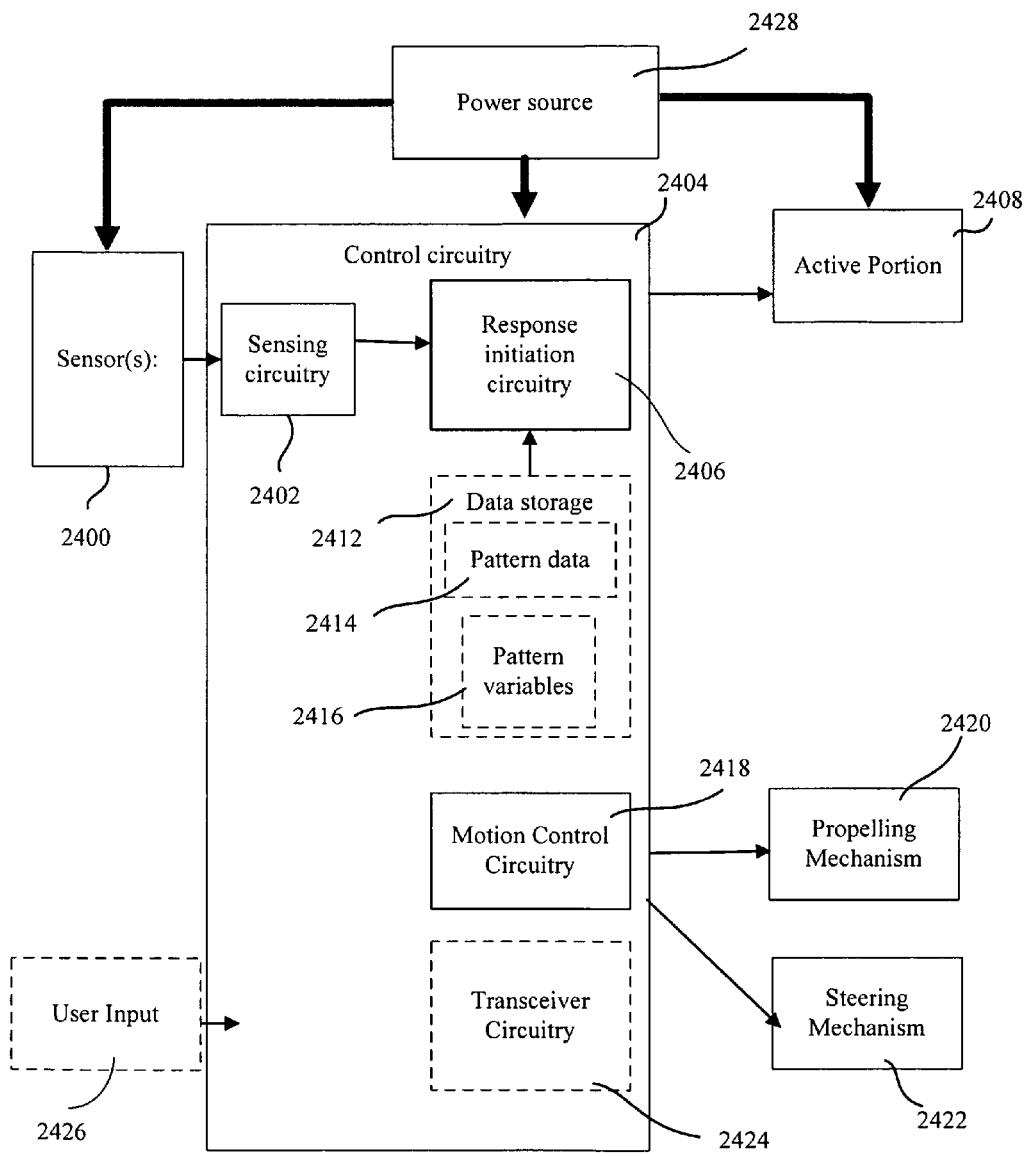
FIG. 41 is a block diagram of a lumen-traveling device system.

FIG. 41 is a block diagram illustrating in greater detail various circuitry components of a lumen-traveling system. As discussed elsewhere herein, the circuitry components may be located entirely on the structural element of a lumen-traveling device, or may be distributed between the lumen-traveling device and a remote portion. The lumen-traveling system may include one or more sensors 2400 for measuring or detecting a condition of interest. Sensing circuitry 2402 may be associated with sensors 2400. The lumen-traveling system may include various control circuitry 2404, including response initiation circuitry 2406. Response initiation circuitry 2406 may provide a response initiation signal to active portion 2408. Control circuitry 2404 may also include data storage portion 2412, which may, for example, be used to store pattern data 2414 or pattern variables 2416 for determining an activation pattern of active portion 2408. Data storage portion 2412 may also store positional information, including, for example, the current device position or the position of one or more target locations or landmarks, or a map of some or all of the relevant body lumen(s) of the subjects. In some embodiments, control circuitry 2404 may include motion control circuitry 2418 for controlling propelling mechanism 2420, and optionally steering mechanism 2422. Control circuitry may include transceiver circuitry 2424, which provides for the transmission and reception of data and/or power signals between the lumen-traveling device and one or more remote portion or external devices (e.g., monitoring or recording equipment). A user input portion 2426 may provide for the input of user instructions, parameter, etc. to control circuitry 2404. Finally, one or more power source 2428 may provide power to electrical components of the lumen-traveling system. Some components of the lumen-traveling device may be operated in whole or in part under software control, and control circuitry 2404 may include hardware, software, hardware, or various combinations thereof. The lumen-traveling device may include components that may be primarily hardware-based, e.g., sensor 2400, active portion 2408, propelling mechanism 2420, steering mechanism 2422, and, optionally, user input device 2426. Hardware-based devices may include components that are electrical, mechanical, chemical, optical, electromechanical, electrochemical, electro-optical, and are not limited to the specific examples presented herein. As described elsewhere, in some embodiments, portions of the control circuitry, including, for example, the response initiation circuitry, may be located in or on the structural element, while in other embodiments the response initiation circuitry may be at a location remote from the structural element.

Figure 42:
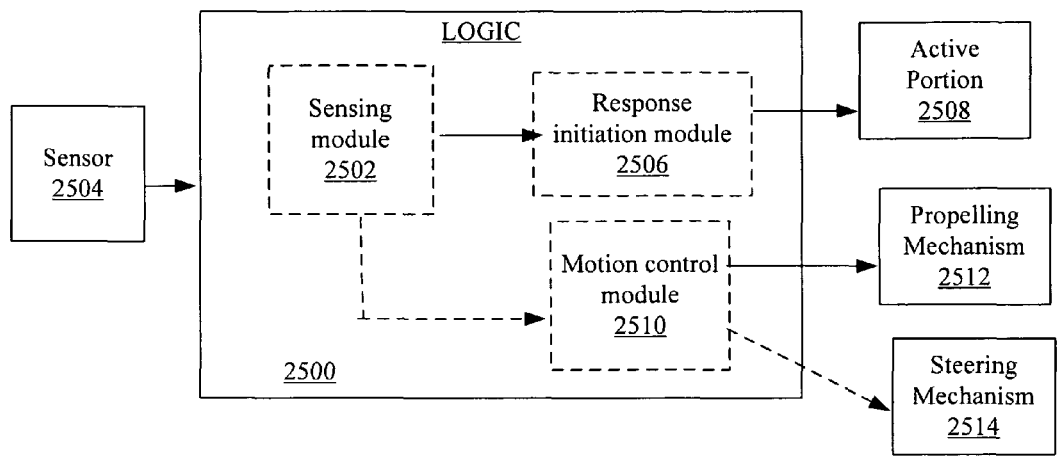
FIG. 42 is block diagram of an embodiment of logic for controlling a lumen-traveling device.
Figure 43:
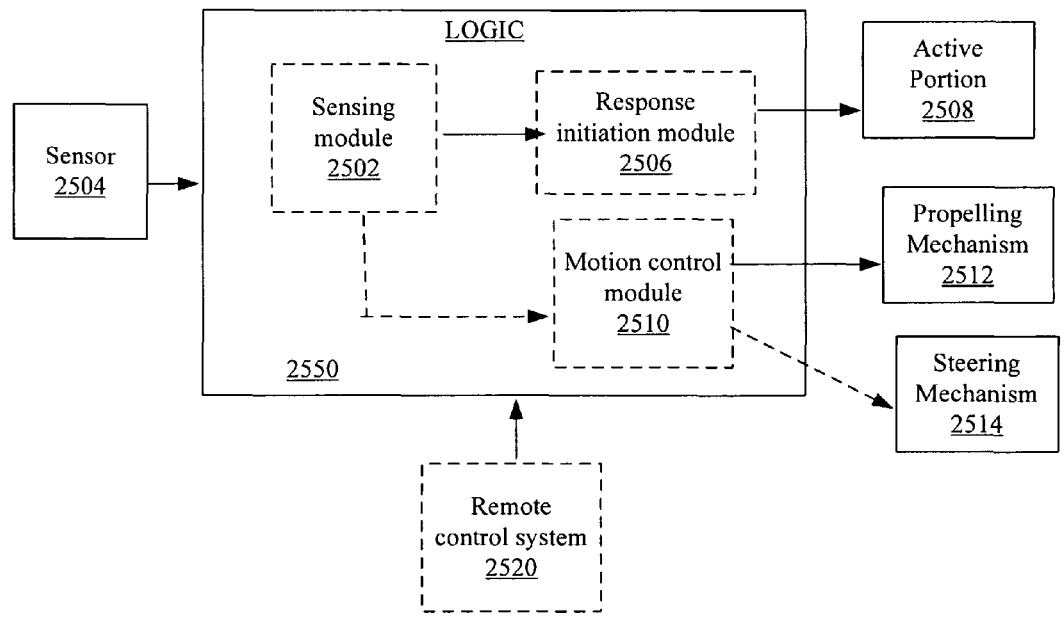
FIG. 43 is a block diagram of a further embodiment of logic for controlling a lumen-traveling device.

In many embodiments, the control circuitry as depicted in FIG. 41 may be implemented in the form of logic, for example software or digital logic circuitry. FIG. 42 depicts modules of logic (which may be software or hardware) which may be used in the control of lumen-traveling devices as described herein. As shown in FIG. 42, logic 2500 for controlling a lumen-traveling device, may include, for example, a sensing module 2502 capable of processing an input from a sensor 2504 on the lumen-traveling device to generate a sense signal indicating detection of a condition of interest in a body lumen of an organism; a response initiation module 2506 capable of receiving the sense signal from the sensing module 2502 and based at least in part upon the sense signal generating a response initiation signal configured for causing an action to be performed in the body lumen by an active portion 2508 of the lumen-traveling device; and a motion control module 2510 capable of controlling at least one of a propelling mechanism 2512 and a steering mechanism 2514 on the lumen-traveling device to control direction or rate of movement of the lumen-traveling device through the body lumen. The logic may be implemented in digital circuitry, analog circuitry, software, or combinations thereof. The motion control module 2510 may be capable of receiving the sense signal from the sensing module 2502 and controlling at least one of the propelling mechanism 2512 and the steering mechanism 2514 on the lumen-traveling device based at least in part upon the sense signal. In one alternative embodiment, as shown in FIG. 43, the motion control 2510 module may be capable of controlling at least one of the propelling mechanism 2512 and steering mechanism 2514 on the lumen-traveling device based at least in part upon a motion control signal from a remote control system 2520. Otherwise, the logic 2550 is like that shown in FIG. 42, including sensing module 2502 capable of processing an input from a sensor 2504 on the lumen-traveling device to generate a sense signal indicating detection of a condition of interest in a body lumen of an organism; a response initiation module 2506 capable of receiving the sense signal from the sensing module 2502 and based at least in part upon the sense signal generating a response initiation signal configured for causing an action to be performed in the body lumen by an active portion 2508 of the lumen-traveling device; and a motion control module 2510 capable of controlling at least one of a propelling mechanism 2512 and a steering mechanism 2514 on the lumen-traveling device to control direction or rate of movement of the lumen-traveling device through the body lumen. In another related embodiment, motion control module 2510 may be capable of controlling at least one of propelling mechanism 2512 and the steering mechanism 2514 on the lumen-traveling device based at least in part upon a pre-programmed motion pattern, for example a motion pattern stored in a data storage location 2412 as data storage location 2412 in FIG. 41. In some embodiments, sensing module 2502 may be capable of generating a sense signal indicating the presence or absence of the condition of interest, wherein response initiation module 2506 may be capable of generating a response initiation signal configured for initiating the performance of the action in the body lumen by active portion 2508 of the lumen-traveling device. Response initiation module 2506 may include control logic that uses a pre-programmed pattern which may be stored in a memory location on the lumen-traveling device (again, like data storage location 2412 in FIG. 41).

In some embodiments, sensing module 2502 may be capable of generating a sense signal indicating the presence or absence of the condition of interest, and response initiation module 2506 may be capable of generating a response initiation signal configured for controlling the performance of the action in the body lumen by the active portion of the lumen-traveling device in a pre-programmed pattern. In some embodiments, the sensing module may be capable of generating a sense signal indicating a parameter value of the condition of interest, wherein the response initiation module may be capable of generating a response initiation signal configured for initiating the performance of the action in the body lumen by the active portion 2508 of the lumen-traveling device as a function of the parameter value of the condition of interest. In addition, response initiation module 2506 may in some embodiments be capable of generating a response initiation signal configured for controlling the action by the active portion 2508 of the lumen-traveling device for a period of time as a function of the parameter value of the condition of interest. In some embodiments, sensing module 2502 may be capable of generating a time-varying sense signal indicating a time-varying parameter value of the condition of interest, wherein he response initiation module 2506 may be capable of generating a response initiation signal configured for controlling active portion 2508 of the lumen-traveling device as a function of the time-varying sense signal.

Figure 44:
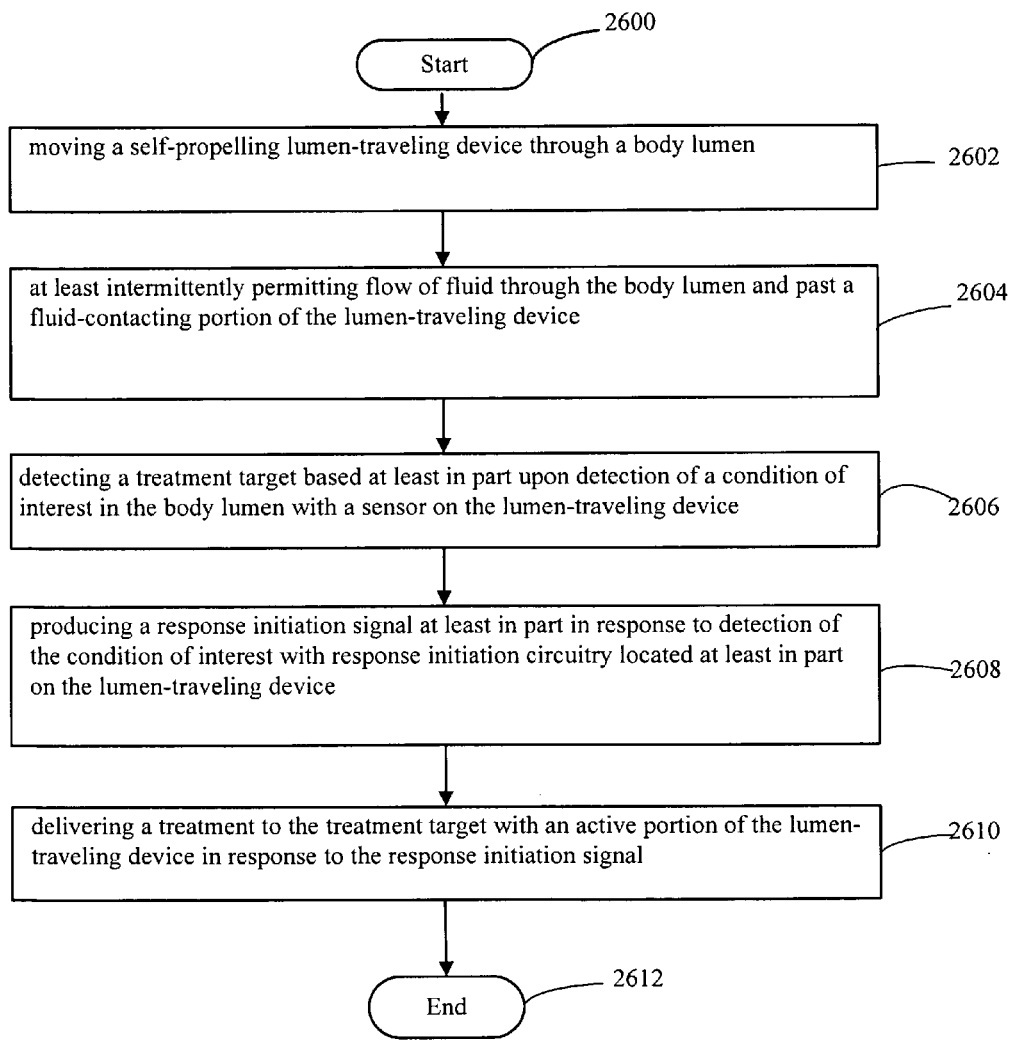
FIG. 44 is flow diagram of a method of using a lumen-traveling device.

FIG. 44 illustrates a method of using a lumen-traveling device, which includes moving a self-propelling lumen-traveling device through a body lumen at step 2602; at least intermittently permitting flow of fluid through the body lumen and past a fluid-contacting portion of the lumen-traveling device at step 2604; detecting a treatment target based at least in part upon detection of a condition of interest in the body lumen with a sensor on the lumen-traveling device at step 2606; producing a response initiation signal at least in part in response to detection of the condition of interest with response initiation circuitry located at least in part on the lumen-traveling device at step 2608; and delivering a treatment to the treatment target with an active portion of the lumen-traveling device in response to the response initiation signal at step 2610.

Figure 45:
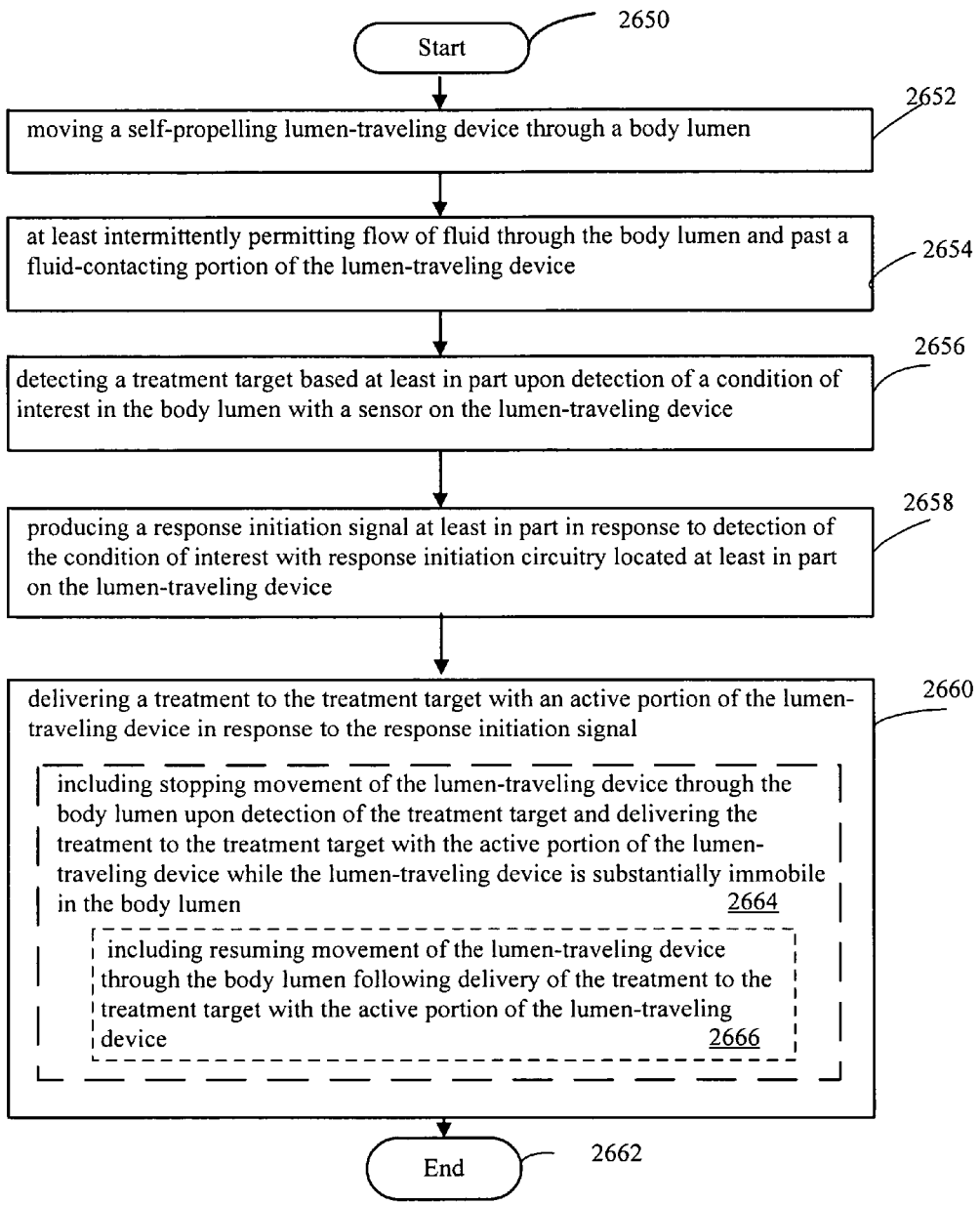
FIG. 45 is a flow diagram of a method of using a lumen-traveling device.

FIG. 45 shows an expanded version of the method of FIG. 44, including the steps of moving a self-propelling lumen-traveling device through a body lumen at step 2652; at least intermittently permitting flow of fluid through the body lumen and past a fluid-contacting portion of the lumen-traveling device at step 2654; detecting a treatment target based at least in part upon detection of a condition of interest in the body lumen with a sensor on the lumen-traveling device at step 2656; producing a response initiation signal at least in part in response to detection of the condition of interest with response initiation circuitry located at least in part on the lumen-traveling device at step 2658; and delivering a treatment to the treatment target with an active portion of the lumen-traveling device in response to the response initiation signal at step 2660, and also including a further step 2664 of stopping movement of the lumen-traveling device through the body lumen upon detection of the treatment target and delivering the treatment to the treatment target with the active portion of the lumen-traveling device while the lumen-traveling device may be substantially immobile in the body lumen. A further method step 2666 may include resuming movement of the lumen-traveling device through the body lumen following delivery of the treatment to the treatment target with the active portion of the lumen-traveling device.

Figure 46:
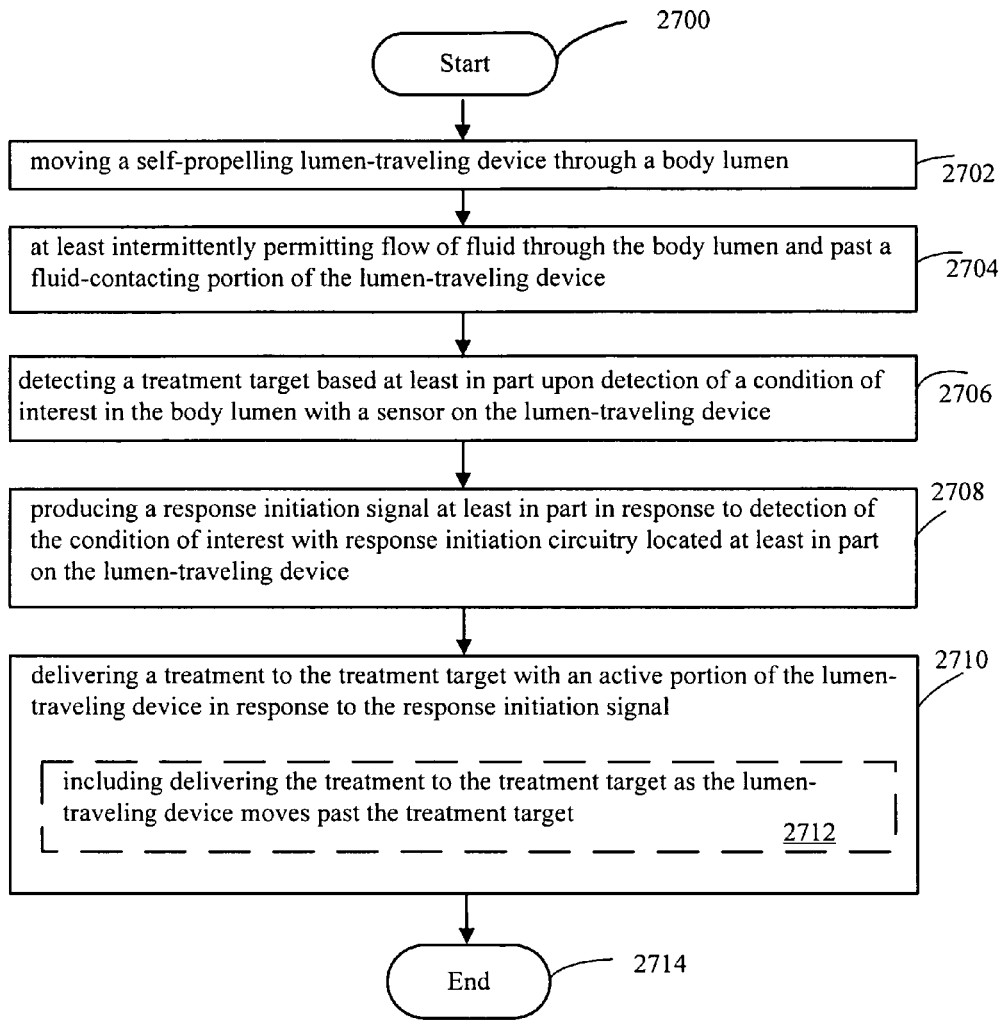
FIG. 46 is a flow diagram of a method of using a lumen-traveling device.

FIG. 46 shows a further variation of the method of FIG. 44, including moving a self-propelling lumen-traveling device through a body lumen at step 2702; at least intermittently permitting flow of fluid through the body lumen and past a fluid-contacting portion of the lumen-traveling device at step 2704; detecting a treatment target based at least in part upon detection of a condition of interest in the body lumen with a sensor on the lumen-traveling device at step 2706; producing a response initiation signal at least in part in response to detection of the condition of interest with response initiation circuitry located at least in part on the lumen-traveling device at step 2708; and delivering a treatment to the treatment target with an active portion of the lumen-traveling device in response to the response initiation signal at step 2710, where delivering the treatment to the treatment target may include delivering the treatment to the treatment target as the lumen-traveling device moves past the treatment target, as shown in step 2712.

In some embodiments of methods as illustrated in FIGS. 44, 45, and 46, a method of using a lumen-traveling device may include delivering the treatment to the treatment target with an active portion of the lumen-traveling device, wherein the treatment may be determined based at least in part upon at least one sensed parameter of the treatment target. In other embodiments, the treatment may be determined at least in part by a treatment pattern stored in the lumen-traveling device.

In some cases, the treatment target may include at least a portion of a wall of the body lumen, or in some cases, the treatment target may lie beyond the wall of the body lumen, so that delivering a treatment to the treatment target with an active portion of the lumen-traveling device in response to the response initiation signal may include delivering a treatment to the treatment target through a wall of the body lumen. In some cases, the treatment target may include at least a portion of the contents of the body lumen.

Figure 47:
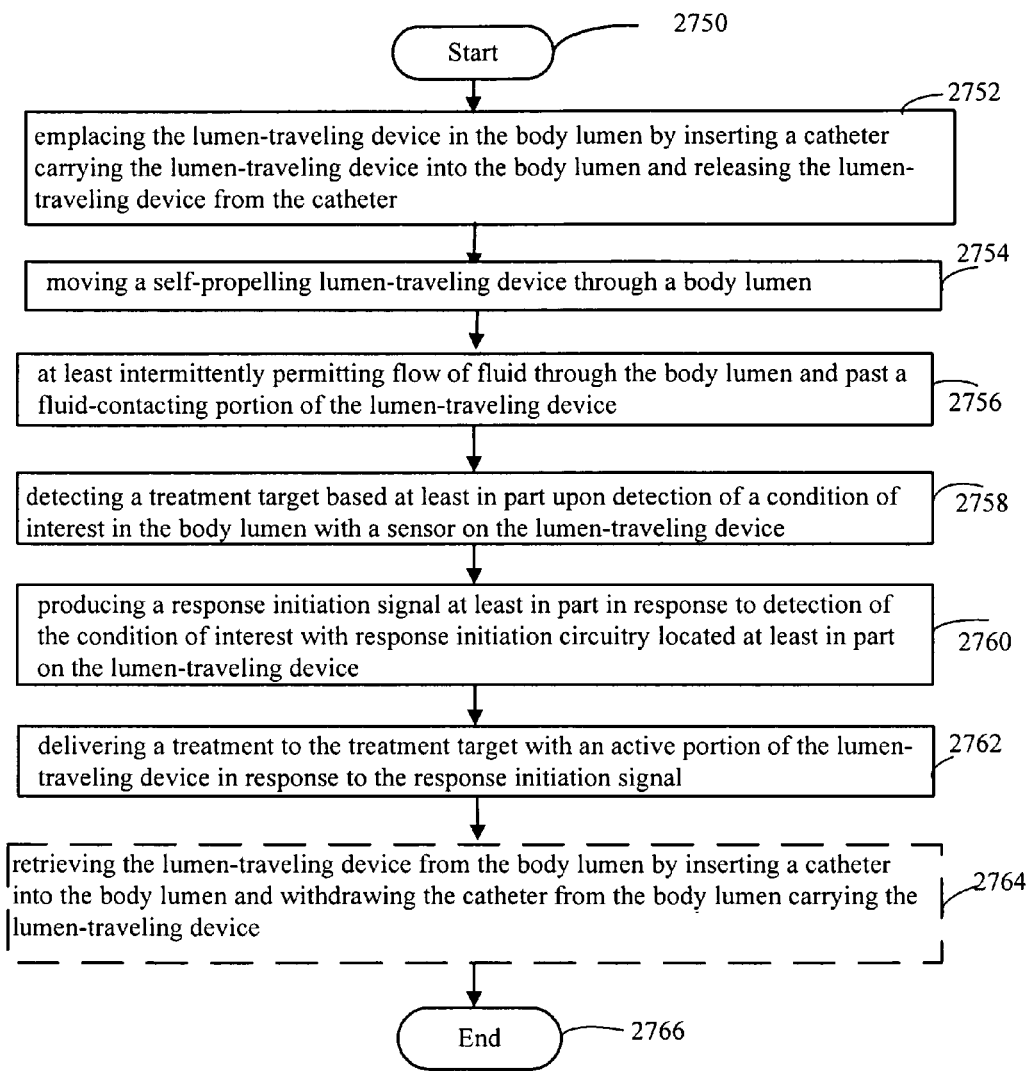
FIG. 47 is a flow diagram of a method of using a lumen-traveling device.

A further method of using a lumen-traveling device, as outlined in FIG. 47, may also include emplacing the lumen-traveling device in the body lumen by inserting a catheter carrying the lumen-traveling device into the body lumen and releasing the lumen-traveling device from the catheter, at step 2752, followed by the steps of moving a self-propelling lumen-traveling device through a body lumen at step 2754; at least intermittently permitting flow of fluid through the body lumen and past a fluid-contacting portion of the lumen-traveling device at step 2756; detecting a treatment target based at least in part upon detection of a condition of interest in the body lumen with a sensor on the lumen-traveling device at step 2758; producing a response initiation signal at least in part in response to detection of the condition of interest with response initiation circuitry located at least in part on the lumen-traveling device at step 2760; and delivering a treatment to the treatment target with an active portion of the lumen-traveling device in response to the response initiation signal at step 2762. A method of using a lumen-traveling device may optionally include retrieving the lumen-traveling device from the body lumen by inserting a catheter into the body lumen and withdrawing the catheter from the body lumen carrying the lumen-traveling device, for example as shown in step 2764 of FIG. 47.

Figure 48A:
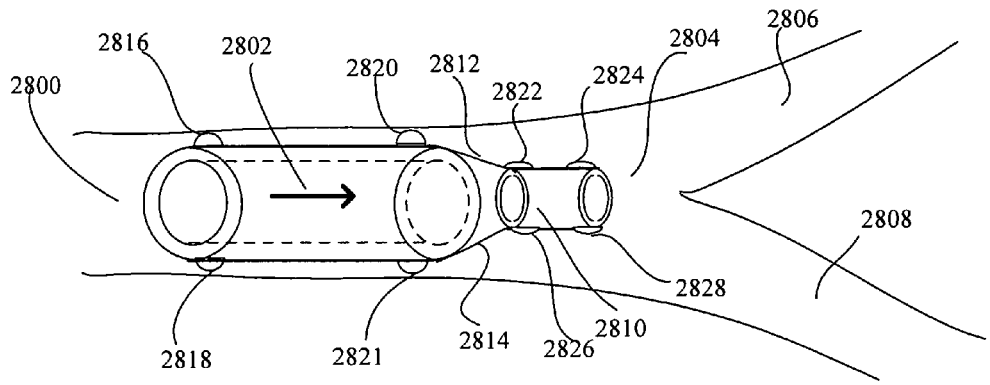
FIGS. 48A-48C illustrate an embodiment of a system including two lumen-traveling devices.
Figure 48B:
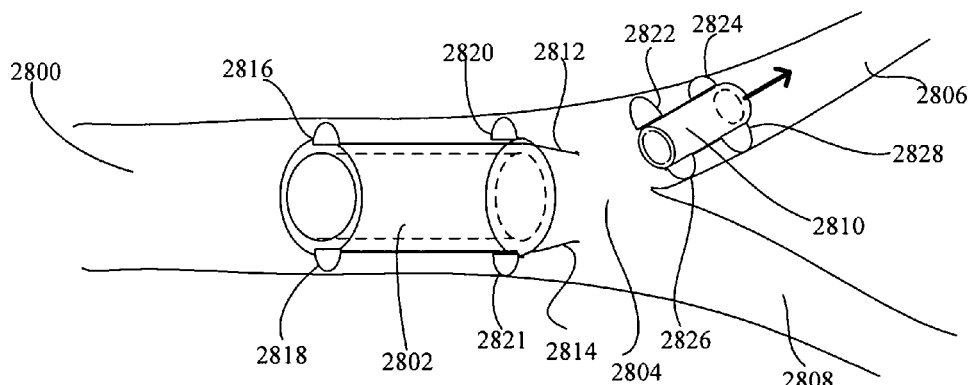
Figure 48C:
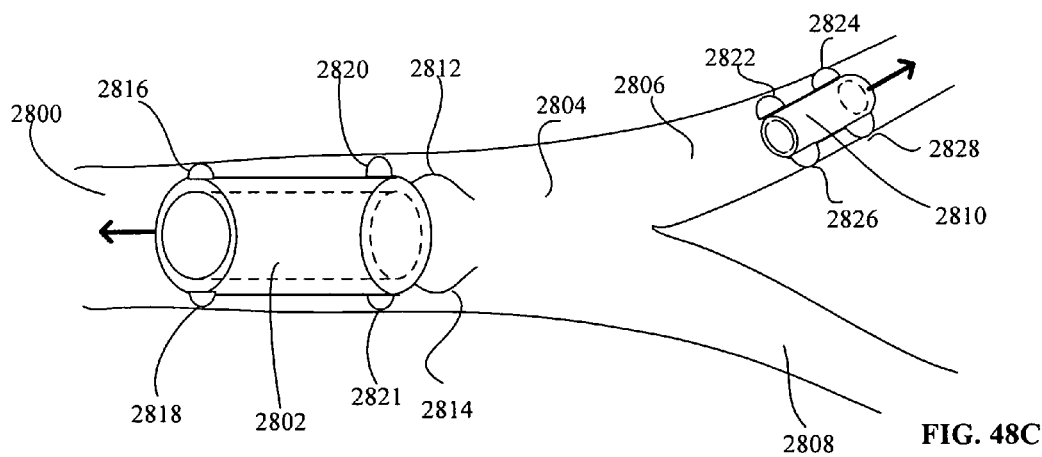

In some embodiments of a method of using a lumen-traveling device, as shown in FIGS. 48A-48C, a primary lumen-traveling device 2802 and a secondary lumen-traveling device 2810 may be used. In some embodiments of a method, e.g., as outlined in FIG. 44, the self-propelling lumen-traveling device may be a secondary lumen-traveling device 2810, and the method may include emplacing secondary lumen-traveling device 2810 in the body lumen by releasing the secondary lumen-traveling device 2810 from a primary lumen-traveling device 2802. In FIG. 48A, primary lumen-traveling device 2802 is located in body lumen 2800 near branch point 2804, where body lumen 2800 branches into smaller branch lumens 2806 and 2808. Secondary lumen-traveling device 1820 is carried by primary lumen-traveling device 2802, attached by retaining portions 2812 and 2814. Primary lumen-traveling device 2802 is propelled through body lumen 2800 (in this example, with lumen-wall-engaging structures 2816, 2818, 2820, and 2821). As shown in FIG. 48B, when primary lumen-traveling device 2802 reaches branch point 2804, it may stop and release secondary lumen-traveling device 2810. Secondary lumen-traveling device 2810 may be smaller than the primary lumen-traveling device 2802, for example to permit it to travel into a smaller body lumen than the primary lumen-traveling device will fit into, such as branch lumen 2806. Secondary lumen-traveling device 2810 may include lumen-wall-engaging structures 2822, 2824, 2826, and 2828, which operate to propel it down branch lumen 2806 and away from primary lumen-traveling device 2802. As illustrated in FIG. 48C, primary lumen-traveling device may leave branch point 2804 after releasing secondary lumen-traveling device 2810.

Primary lumen-traveling device 2802 and secondary lumen-traveling device 2810 may be substantially similar in design, but of different sizes, as depicted in FIGS. 48A-48C. In some embodiments of a method as outlined in FIG. 44, a self-propelling lumen-traveling device (as recited in the method of FIG. 44) may be a primary lumen-traveling device as depicted in FIG. 48, and the method may include emplacing a secondary lumen-traveling device in the body lumen by releasing the secondary lumen-traveling device from the primary lumen-traveling device. As depicted in FIG. 48, the secondary lumen-traveling device may be smaller than the primary lumen-traveling device.

Figure 49:
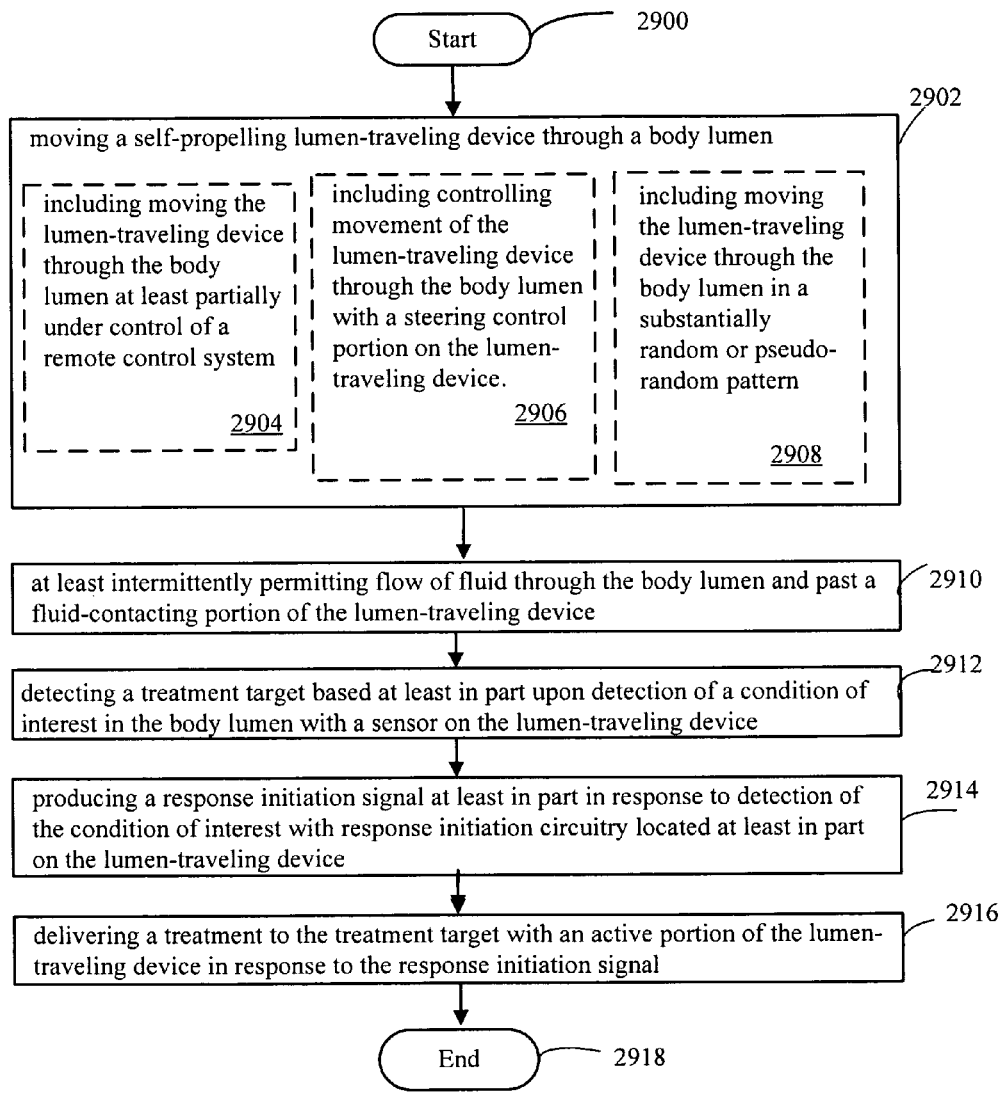
FIG. 49 is a flow diagram of a method of using a lumen-traveling device.

FIG. 49 shows a method which includes moving a self-propelling lumen-traveling device through a body lumen at step 2902; at least intermittently permitting flow of fluid through the body lumen and past a fluid-contacting portion of the lumen-traveling device at step 2910; detecting a treatment target based at least in part upon detection of a condition of interest in the body lumen with a sensor on the lumen-traveling device at step 2912; producing a response initiation signal at least in part in response to detection of the condition of interest with response initiation circuitry located at least in part on the lumen-traveling device at step 2914; and delivering a treatment to the treatment target with an active portion of the lumen-traveling device in response to the response initiation signal at step 2916. In addition, the method of FIG. 49 may include moving the lumen-traveling device through the body lumen at least partially under control of a remote control system, e.g., of the type illustrated in FIG. 35, as indicated at step 2904. For example, a motion control signal may be transmitted to the lumen-traveling device with the remote control system. The motion control signal may be generated with the remote control system. The motion control signal may be received from a remote control system with a signal receiver in the lumen-traveling device. The method may also include transmitting a signal indicative of detection of a condition of interest from the lumen-traveling device to a remote location, or transmitting a signal indicative of performance of an action by the lumen-traveling device to a remote location.

Alternatively, as shown in FIG. 49, step 2906, a method of using a lumen-traveling device may include controlling movement of the lumen-traveling device through the body lumen with a steering control portion on the lumen-traveling device. It should be noted that in some embodiments, propulsion may be provided without steering. In some embodiments, movement of the lumen-traveling device through the body lumen may be controlled based at least in part upon a detected condition of interest in the body lumen, controlled based at least in part on the use of logic circuitry included in the lumen-traveling device, and/or controlled based at least in part on a movement pattern stored in the lumen-traveling device. In another alternative, the lumen-traveling device may be moved through the body lumen in a substantially random or pseudo-random pattern, as indicated in FIG. 49, step 2908.

In this and other embodiments of methods disclosed herein, detecting a condition of interest may include detecting a variety of conditions, including but not limited to, an embolism, a plaque, a thrombus, an aneurysm, a stenosis, a puncture, a perforation, a rupture, a dissection, a tear, or a branching point in the body lumen, the branching point including at least two branches of the body lumen. The term "condition", as used herein, may refer to normally occurring anatomic features, man-made or other foreign structures, features, or conditions, disease states or injuries that may be present in a lumen by chance or purpose, and various detectable or measurable characteristics or parameters that indicate the presence of such conditions or features. In some embodiments, the method may include detecting a branching point in the body lumen, the branching point including at least two branches of the body lumen; the method may then also include steering the lumen-traveling device into a selected one of the at least two branches of the body lumen.

Several additional examples of embodiments of lumen-traveling devices are now provided, to further illustrate use of lumen-traveling devices as described herein.

Figure 50A:
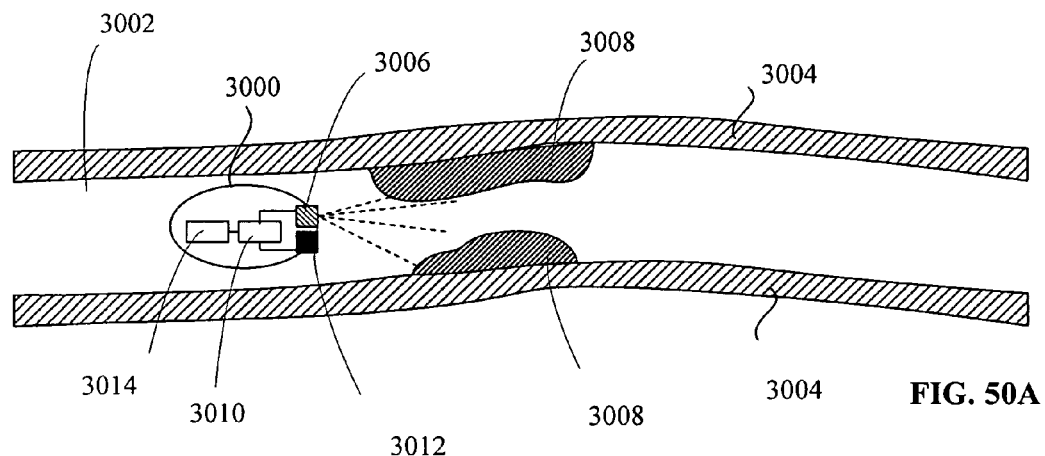
FIGS. 50A and 50B are longitudinal cross-sectional views of an example of the operation of a lumen-traveling device in a body lumen.
Figure 50B:
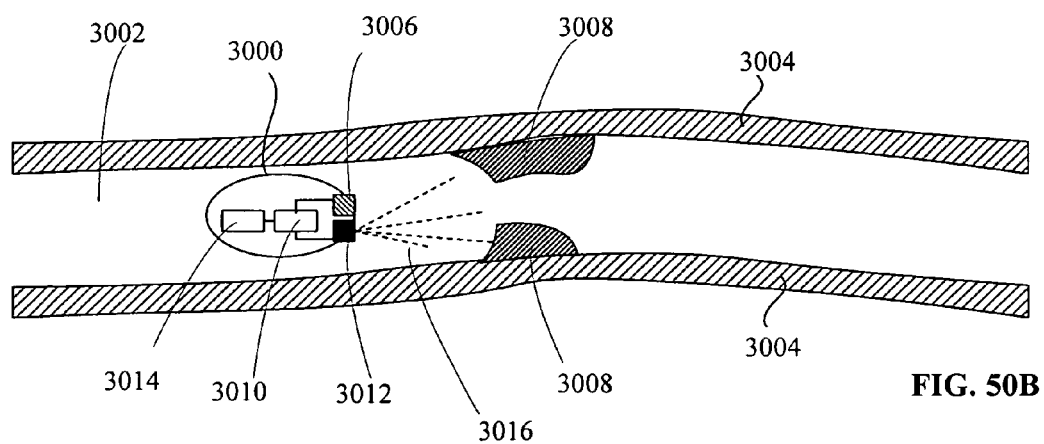

FIGS. 50A and 50B depict lumen-traveling device 3000 moving through a body lumen 3002. Lumen-traveling device 3000 includes sensor 3006, response initiation circuitry 3010, and active portion 3012. Lumen-traveling device 3000 also includes motion control circuitry 3014. As shown in FIG. 50A, sensor 3000 detects a location of interest—in this case, material 3008 on the wall 3004 of body lumen 3002. Material 3008 may be, for example, a plaque on the wall of an artery. Sensor 3006 may be an optical sensor, an imaging device, or various other types of sensors, as are known to those of skill in the art. Upon detection of material 3008, active portion 3012 may be an activated, as shown in FIG. 50B. In this example active portion 3012 performs ablation of material 3008; for example, active portion 3012 may be an optical device which generates light to perform, for example, laser ablation of a plaque, or it may be an acoustic device for performing ultrasonic ablation of a plaque.

Figure 51A:
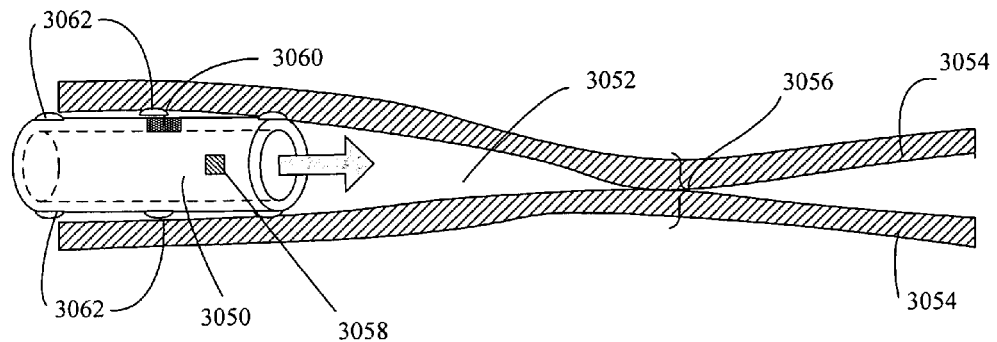
FIGS. 51A and 51B are longitudinal cross-sectional views of an example of the operation of a lumen-traveling device in a body lumen.
Figure 51B:
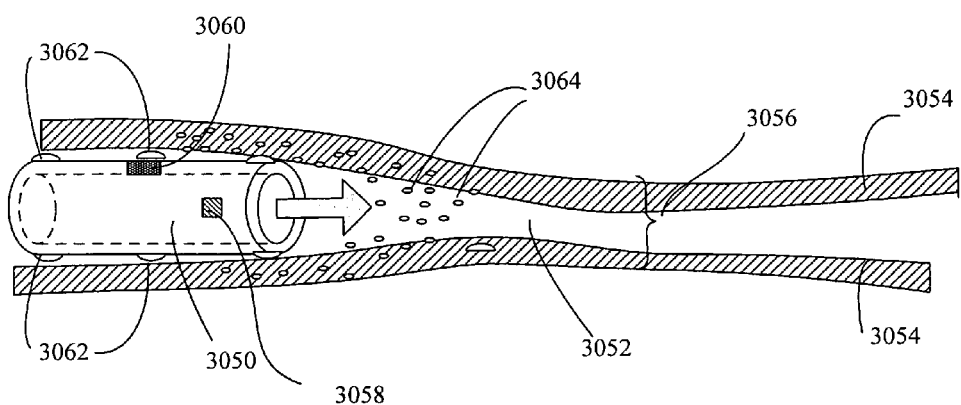

FIGS. 51A and 51B depict a lumen-traveling device 3050 moving through a lumen 3052 that is constricted, e.g. by a vasospasm. Lumen 3052 is defined by lumen walls 3054, which at vasospasm 3056 are constricted, blocking the flow of fluid through the lumen. Lumen-traveling device 3050 includes sensor 3058, which detects the presence of the vasospasm, for example, by detecting reduced flow of fluid through the body lumen. Lumen-traveling device 3050 also includes material release structure 3060, which may be activated in response to detection of vasospasm 3056, to release a vasoactive substance 3064 to produce relaxation of the vasospasm, as illustrated in FIG. 51B. Lumen-traveling device 3050 may also include propelling mechanism 3062, as well as other components not depicted in FIGS. 51A and 51B, but as described elsewhere herein.

Figure 52B:
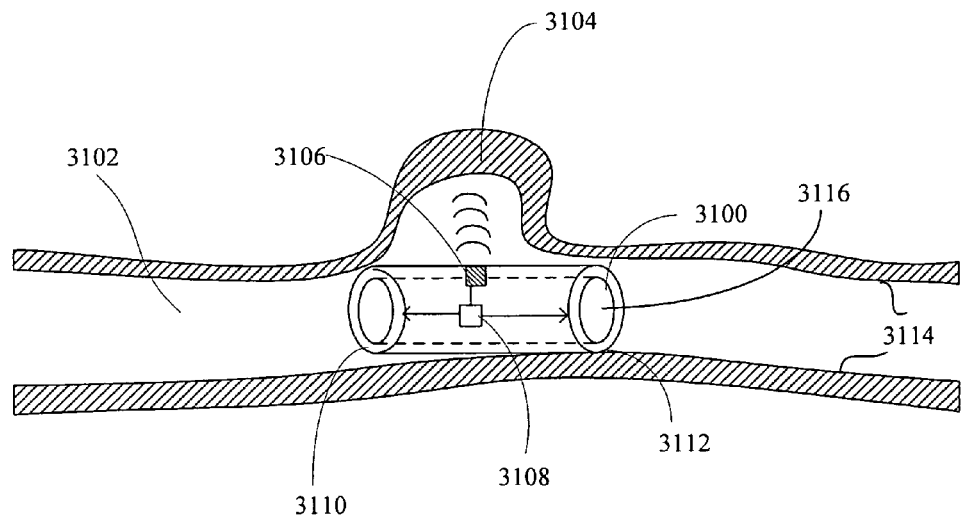
FIGS. 52A and 52B are longitudinal cross-sectional views of an example of the operation of a lumen-traveling device in a body lumen.
Figure 52A:
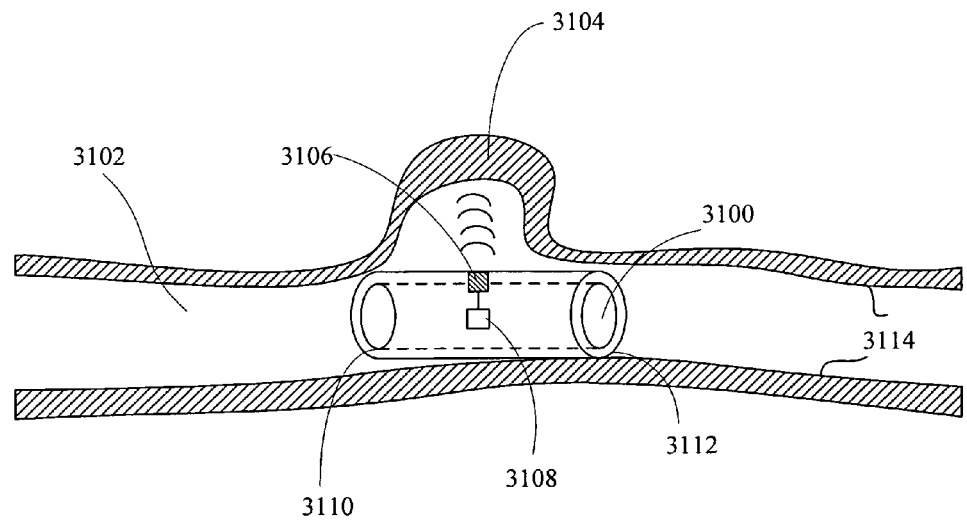

FIGS. 52A and 52B illustrate a further example of a lumen-traveling device 3100 traveling through a body lumen 3102. Body lumen 3102 includes an aneurysm 3104, which may be detected by sensor 3106 on lumen-traveling device 3100. A sense signal generated by sensor 3106 causes response initiation circuitry 3108 to cause activation of active portions 3110 and 3112 to engage walls 3114 of body lumen 3102 to seal off aneurysm 3104 and cause fluid to flow through central lumen 3116 of lumen-traveling device 3100, rather than into aneurysm 3104.

Figure 53A:
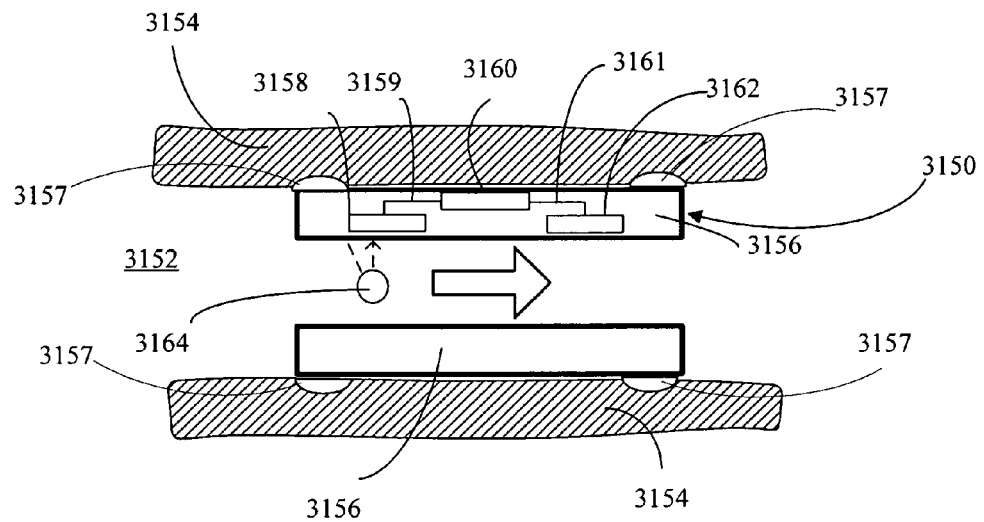
FIGS. 53A and 53B are longitudinal cross-sectional views of an example of the operation of a lumen-traveling device in a body lumen.
Figure 53B:
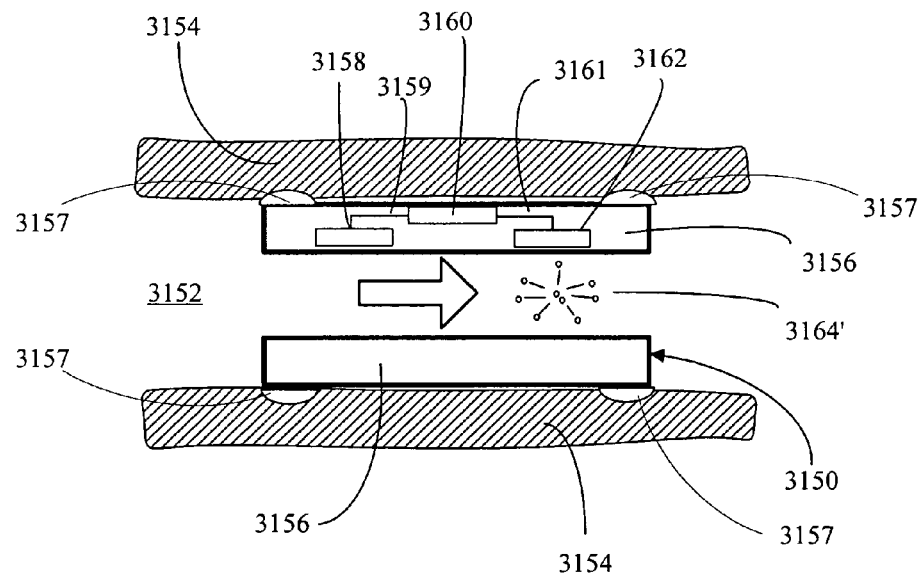

FIGS. 53A and 53B illustrate the treatment of a fluid flowing through a lumen-traveling device 3150 positioned in a body lumen 3152. The lumen-traveling device 3150 may move to a location of interest, for example, and then engage the lumen walls to remain in the location of interest and treat fluid moving through it. Alternatively, lumen-traveling device 3150 may treat fluid as it moves through body lumen 3152, including fluid residing in or flowing through the lumen-traveling device. Body lumen 3152 is defined by wall portions 3154. In FIG. 53A, component 3164 of fluid flowing through body lumen 3152 is detected by sensor 3158 in structural element 3156 of lumen-traveling device 3150. Upon detection of component 3164 by sensor 3158, a sense signal 3159 is sent to response initiation circuitry 3160, which generates a response initiation signal 3161. Response initiation signal 3161 is sent to active portion 3162. As shown in FIG. 53B, upon receipt of response initiation signal 3161, active portion 3162 produces a response or action, which in this example is a pulse of energy (e.g. acoustic energy) to destroy component 3164 (indicated following destruction by reference number 3164'). For example, a pulse of acoustic energy may be used to modify a kidney stone in the urinary tract, or to modify another object in another body fluid.

In connection with detection of the presence of a material, location, or other condition(s) of interest within or near the body lumen or the lumen contents, the active portion of the lumen-traveling device or system may be capable of removing, modifying, or destroying a material of interest or treating a location of interest. Modification or destruction of the material of interest may be accomplished by the release of a suitable material (e.g. an anti-coagulant for destroying a blood clot, complement to coat a parasite for recognition by the immune system, or by the release of an anti-inflammatory, biomimetic or biologic to bind to and inactivate an inflammatory mediator such as TNFα, by the delivery of suitable energy (e.g., acoustic energy for modifying a kidney stone, electromagnetic energy such as light to cause a photoreaction, break bonds in a molecule, produce heating, vaporization, ablation, etc., or by delivery of heat or cold or other chemo-physical change (e.g. ambient pressure, pH, osmolality, toxic material introduction/generation) for tissue modification, as in ablation of circulating tumor cells or plaque or temperature-induced modification of sperm as it passes through the vas deferens.

In some embodiments of lumen-traveling devices or systems, a lumen-traveling device may be a self-contained device that includes all functionalities necessary for operation of the device. In other embodiments, as illustrated in FIG. 28, 35 or 43, a lumen-traveling system may include a lumen-traveling device that may be placed in a body lumen, and a remote portion that includes a portion of the functionalities of the lumen-traveling system. In some embodiments, all functionalities essential for the operation of the lumen-traveling device may be located on the lumen-traveling device, but certain auxiliary functions may be located in the remote portion. For example, the remote portion may provide monitoring of the operation of the lumen-traveling device or data collection or analysis. The remote portion may be located within the body of the subject at a distance from the lumen-traveling device, or outside the body of the subject, as depicted in FIG. 28. The remote portion may be located near the subject (e.g., carried or worn on the subject's body or placed on a table near the subject) or distant from the subject (e.g. in a different room or building, or in a different city, state or country). Data and/or power signals may be transmitted between lumen-traveling device and remote portion with the use of electromagnetic or acoustic signals, or, in some embodiments, may be carried over electrical or optical links. Various types and/or combinations of types of communications methods and devices may be used, as are known to those of skill in the art. In some embodiments, transmission of information between the lumen-traveling device and one or more remote portions may be via multiple communication channels, in series or in parallel. In general, the remote portion may be placed in a location where there is more space available than within the body lumen, or that is more readily accessible than the body lumen. It is contemplated that a portion of the electrical circuitry portion of the lumen-traveling system (which may include hardware, firmware, software, or any combination thereof) may be located in a remote portion.

Methods of distributing functionalities of a system between hardware, firmware, and software located at two or more sites are well known to those of skill in the art. An electrical circuitry portion of the lumen-traveling system may include, but is not limited to, electrical circuitry associated with the sensor, response initiation circuitry, and electronics associated with the active portion. While the response initiation circuitry has been discussed within the context of electrical circuitry, it will be appreciated that in some embodiments other types of logic/circuitry may be used in place of or in addition to electrical circuitry, and the response initiation circuitry and other circuitry described herein is not limited to electrical circuitry. For example, fluid circuitry, chemo-mechanical circuitry, and other types of logic/circuitry may provide equivalent functionality and may be used in certain embodiments.

In some embodiments, the lumen-traveling device may include an external steering system capable of transmitting a wireless control signal to the structural element. In some embodiments, the lumen-traveling device may include a steering control portion in or on the structural element. Either the steering control portion in or on the structural element or an external steering system may be operated in a number of ways.

A lumen-traveling device may include an imaging marker or tag, and the remote portion may include an external imaging system or be capable of receiving information from an external imaging system. The position of the lumen-traveling device may be correlated with a pre-existing map of the body of the subject, or used to construct a map of the body of the subject. Movement of the lumen-traveling device may be controlled based at least in part upon the location of the lumen-traveling device within the body of the subject. In some embodiments, the lumen-traveling device may include a data storage location in which a map of the body of the subject may be stored. A pre-existing map may be stored in the data storage location before the lumen-traveling device is introduced into the body lumen of the subject. Alternatively, a map may be generated, either with the use of logic on the device or in a remote system, on the basis of information gathered as the device travels through the body of the subject, and the map thus generated may be stored in a memory location on the lumen-traveling device or elsewhere. In some embodiments, rather than storing a map, other positional or locational information may be stored that may be used to control the route taken through the body by the lumen-traveling device. In some embodiments, it may be desired that the device covers some statistical distribution of lumen sizes or locations during its travels, but it may not be necessary that it travel a specific route through the body, and size and location information for already-visited sites may be stored and used in selection of the route to be taken by the devious.

Figure 54:
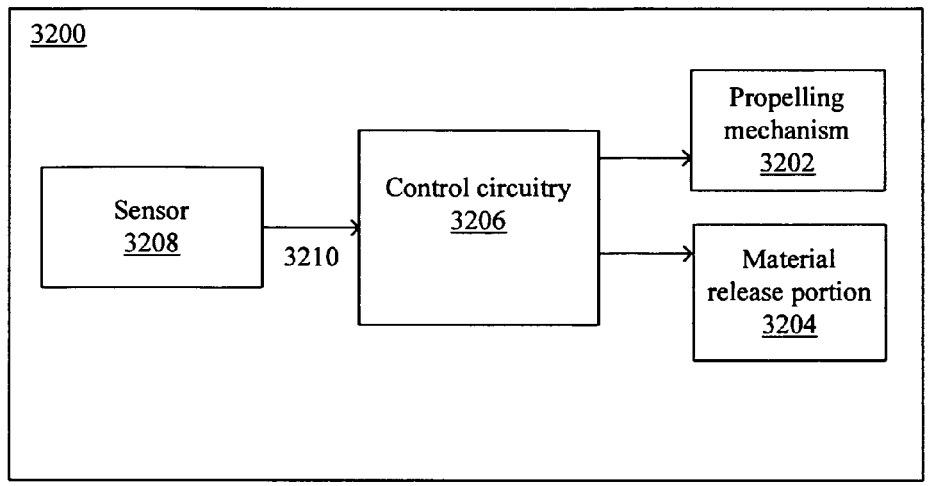
FIG. 54 is a block diagram of an embodiment of a lumen-traveling delivery device.

In a further embodiment, as depicted in FIG. 54, lumen-traveling delivery device 3200 may include propelling mechanism 3202; material release portion 3204; and control circuitry 3206 located at least in part on delivery device 3200, the control circuitry 3206 capable of controlling the operation of propelling mechanism 3202 to move delivery device 3200 through the body lumen to a treatment target and controlling material release portion 3204 to release a deliverable material. For example, material release portion 3204 may be controlled to release the deliverable material when delivery device 3200 is in the vicinity of the treatment target. The device 3200 may include a sensor 3208 capable of generating a sense signal 3210 upon detection of a condition of interest, and wherein control circuitry 3206 may be configured to receive sense signal 3210 and control at least one of the operation of propelling mechanism 3202 and material release portion 3204 based upon receipt of sense signal 3210. Sensor 3208 may be capable of generating sense signal 3210 upon detection of a local condition of interest, for example.

The device may include a structural element sized to fit within a body lumen in the vicinity of a treatment target. The structural element may include a substantially tubular structure, as shown in FIGS. 1-4, for example, or the structural element may include multiple lumens in fluid communication with the body lumen, as shown in FIG. 5B, 5C, or 5F. Alternatively, a structural element may include a capsule-like structure as shown in FIGS. 5A and 6. The structural element may include a self-expanding material, a resilient material, a mesh-like material, or a slotted structure, as described and illustrated herein.

A variety of different types of propelling mechanisms may be used in a lumen-traveling delivery device. Examples include a peristaltic propelling mechanism as depicted in FIGS. 32A and 32B. In other embodiments, the propelling mechanism may include two or more alternately activated limbs, as shown in FIG. 31, or at least one rotating lumen-wall-engaging structure as shown in FIG. 1.

In some embodiments, the device may include at least a first lumen-wall-engaging structure and a second lumen-wall-engaging structure, wherein the propelling mechanism produces lengthening and shortening of the delivery device between the first lumen-wall-engaging structure and the second lumen-wall-engaging structure in coordination with alternate engagement and disengagement of the first lumen-wall-engaging structure and the second lumen-wall-engaging structure, as depicted generally in FIGS. 29A-29E.

The material release portion may include a reservoir containing the deliverable material and including a rupturable barrier, as illustrated in FIGS. 19A and 19B. Alternatively, the material release portion may include a degradable barrier as depicted in FIGS. 20A and 20B, or a reservoir containing the deliverable material and including a barrier having a controllable permeability, as depicted in FIGS. 21A and 21B. In another alternative embodiment, the material release portion may include the deliverable material in a carrier material, as shown in FIGS. 23A and 23B. Although a single release portion is depicted in the figures, the invention is not limited to the use of a single release portion, and in some embodiments, two or more release portions may be used. A release portion may release a single material or multiple materials. In embodiments in which two or more materials are released, either from the same or different release portions, each material may be released according to a different temporal profile. For example, a first material may be released over a first time interval, and a second material may be released over a second time interval. Alternatively, in some embodiments, two or materials may be released simultaneously. The number of materials released and the release profile for each material may be selected according to methods and practices known to those of skill in the relevant arts, in order to produce a desired therapeutic effect, for example. The release of materials from a release portion may be controlled by the control circuitry, as described herein.

Figure 55:
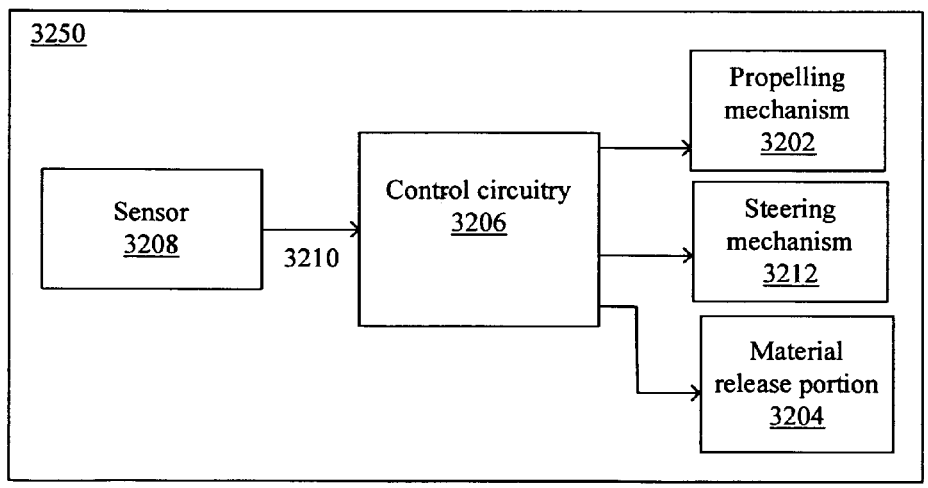
FIG. 55 is a block diagram of another embodiment of a lumen-traveling delivery device.

In some embodiments, as depicted in FIG. 55, the device may include a steering mechanism 3212 capable of modifying the movement of the delivery device. The steering mechanism may be controllable by the control circuitry.

Figure 56A:
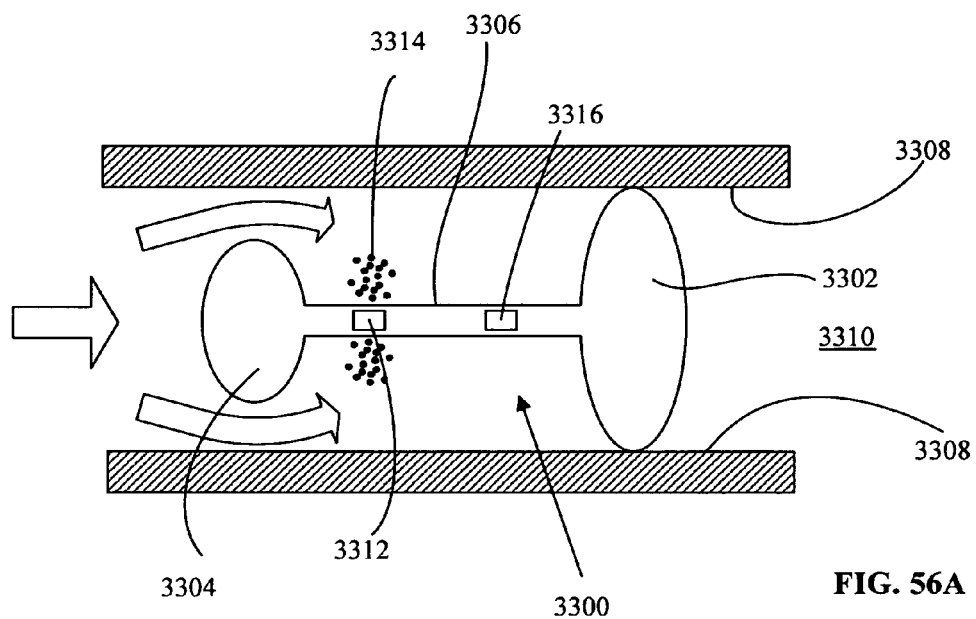
FIGS. 56A and 56B illustrate an embodiment of a lumen-traveling delivery device.

In some embodiments, the device may include an expanding or extending portion configured to at least temporarily seal with a wall of the body lumen to block a flow of fluid through at least a portion of the body lumen. Lumen-traveling device 3300, depicted in FIGS. 56A and 56B, may employ a propelling mechanism as described previously in connection with FIGS. 29A-29E. Lumen-traveling device 3300 may include first expanding or extending portion 3302 and second expanding or extending portion 3504, connected by region 3306. Region 3306 may lengthen and shorten to increase or decrease the distance between first and second expanding or extending portions 3302 and 3304. In FIG. 56A, first expanding or extending portion 3300 has expanded/extended to seal with body lumen wall 3308 to block the flow of fluid through body lumen 3310. Expanding or extending portion 3302 is downstream of material release portion 3312. The direction of fluid flow is indicated by the arrows. In the embodiment depicted in FIGS. 56A and 56B, fluid flows around, rather than through region 3306, so expansion/extension of expanding or extending portion 3302 may completely block the flow of fluid through body lumen 3310. In embodiments as depicted in FIGS. 29A-29E, in which the lumen-traveling device includes one or more lumen through which fluid may flow within the lumen-traveling device (e.g., central lumen 1668 in FIGS. 29A-29E), the one or more lumen may include a closeable valve, for example, to completely block the flow of fluid through the body lumen. For example, as depicted in FIG. 56A, first expanding or extending portion 3302 may be configured to block the flow of fluid through body lumen 3310 downstream of the controllable material release portion 3312. Material 3314 may be released from material release portion 3312. Expanding or extending portion 3302 may block the flow of fluid to keep material 3314 in the vicinity of lumen-traveling delivery device 3300.

Figure 56B:
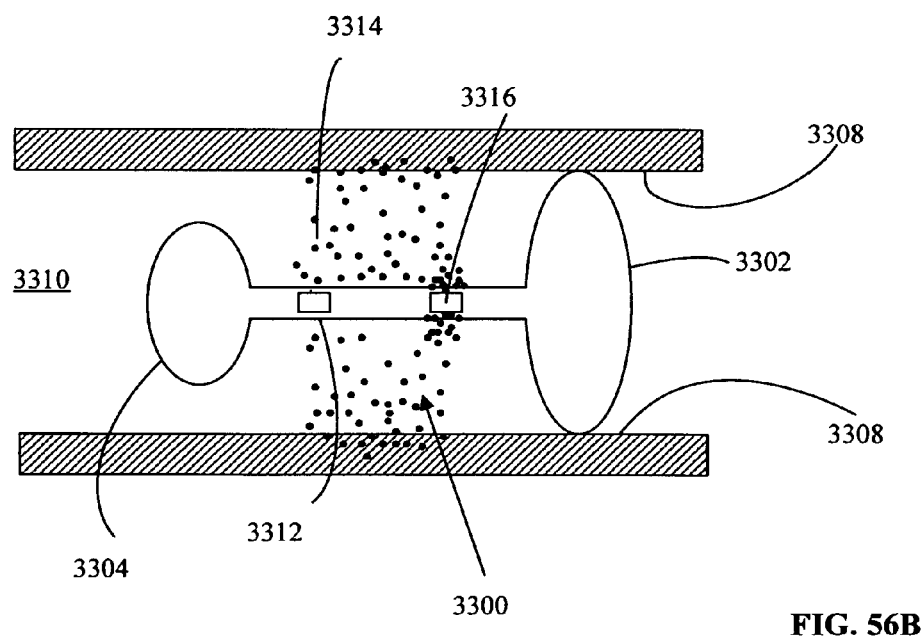

The device may then also include a capture portion 3316 capable of capturing material 3314 that has been released from controllable material release portion 3312. Capture portion 3316 may include materials, structures, or mechanisms like those used in the sample collection portion described elsewhere herein, and may include, for example, absorptive materials, specific, semi-specific, or non-specific adsorbers, absorbers, or binding agents, recognition elements, etc. The capture may include a separator such as a molecular sieve or mechanical filter. FIG. 56A shows material 3314 being released from material release portion 3312, while FIG. 56B shows material 3314 being captured by capture portion 3316. One or both of material release portion 3312 and capture portion 3316 may be controlled by control circuitry. Control circuitry is not shown in FIGS. 56A and 56B, but is as described elsewhere herein.

If a lumen-traveling delivery device includes a structure such as expanding or extending portion 3302 in FIGS. 56A and 56B, which functions as a blocking portion to block the flow of fluid, material 3314 released from material release portion 3312 may remain in the vicinity of lumen-traveling delivery device 3300, where it can be more readily captured by capture portion 3316. The ability to capture much of material 3314 may be useful in cases where it is desirable to have high local concentrations of material 3314 in the vicinity of the lumen-traveling delivery device for a period of time, but to limit the distribution of material 3314 systemically (as may be the case if material 3314 is a drug such as a chemotherapy agent that has undesirable side-effects if occurs in a high systemic concentration). The use of a capture portion in combination with a downstream blocking portion may be useful in some cases, but may not be necessary or desirable in all cases. Thus in some embodiments, a lumen-traveling delivery device may include a capture portion that is capable of capturing material released from the controllable material release portion, but not include a blocking portion for blocking the flow of fluid through the body lumen.

As described in connection with FIGS. 56A and 56B, a lumen-traveling delivery device may include a blocking portion that modifies fluid flow to influence local concentration of material release from a material release portion. In some embodiments, the lumen traveling device may include a flow-modulating element configured to at least temporarily alter the flow of fluid within the body lumen, where the flow-modulating element is not limited to a blocking portion. For example, a flow-modulation element (e.g., as depicted in FIGS. 10A-10H) may produce turbulence, increase or decrease fluid flow, direct fluid flow toward a particular region, etc. to influence the delivery of the material released from the material release portion.

In some embodiments, the lumen-traveling delivery device may include a permeability enhancer for enhancing the permeability of the wall of the lumen in the vicinity of the treatment target. The permeability enhancer may be, for example, mechanical permeability enhancer such as hollow microneedles capable of penetrating the lumen wall, as described in U.S. Pat. No. 6,743,211, a chemical permeability enhancer as described in MURTHY, S. NARASIMHA; HIREMATH, SHOBHA RANI R.; "Physical and Chemical Permeation Enhancers in Transdermal Delivery of Terbutaline Sulphate"; AAPS PharmSciTech; bearing a date of 2001; pp. 1-5; Vol. 2001, 2(1); located at http://www.pharmscitech.com/ and SENEL, SEVDA; HINCAL, A. ATILLA; "Drug permeation enhancement via buccal route: possibilities and limitations"; Journal of Controlled Release; bearing a date of 2001; pp. 133-144; Vol. 72 (2001); Elsevier; located at www.elsevier.com/locate/jconrel and in U.S. Pat. No. 6,673,363, which may be released from the lumen-traveling delivery device along with the material or from a separate reservoir or other source; an electrical permeability enhancer, such as an voltage source for producing electroporation, as in U.S. Pat. No. 6,512,950 or 6,022,316; a magnetic permeability enhancer as described in MURTHY, S. NARASIMHA; HIREMATH, SHOBHA RANI R.; "Physical and Chemical Permeation Enhancers in Transdermal Delivery of Terbutaline Sulphate"; AAPS PharmSciTech; bearing a date of 2001; pp. 1-5; Vol. 2001, 2(1); located at http://www.pharmscitech.com/; all of which patents and literature references are incorporated herein by reference. The permeability enhancer may be capable of enhancing the permeability of the blood-brain barrier in the vicinity of the treatment target, for example.

Figure 57A:
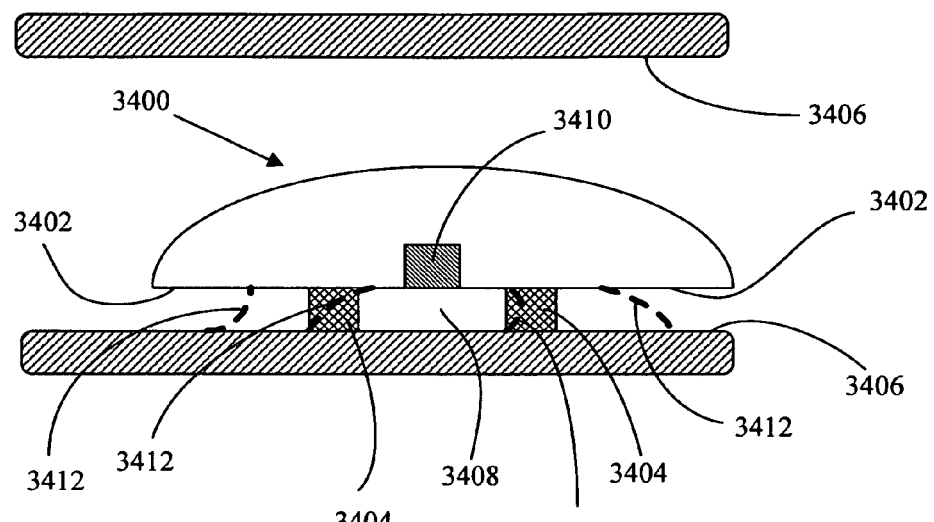
FIG. 57A is a cross-sectional view of a lumen-traveling delivery device.
Figure 57B:
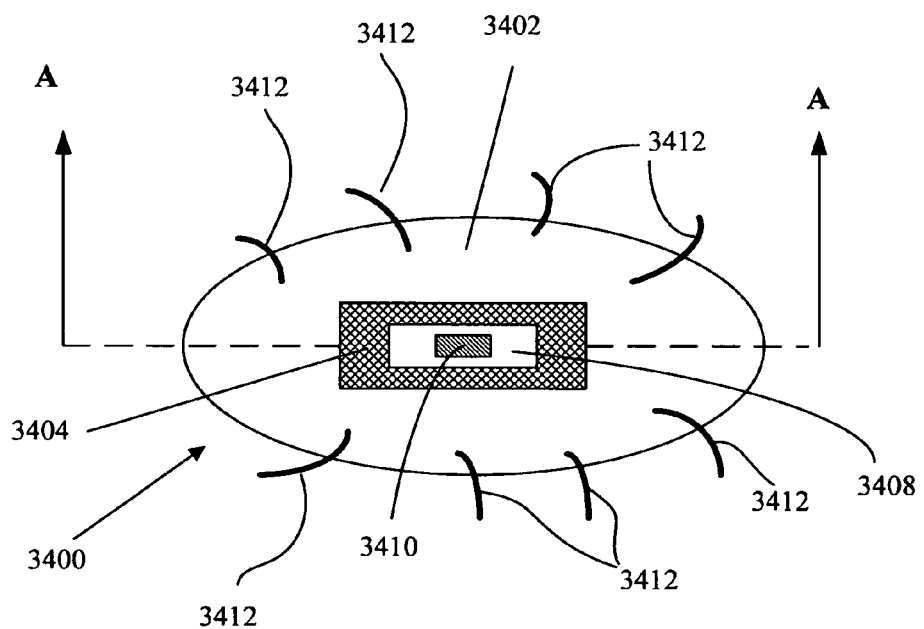
FIG. 57B is a bottom view of the lumen-traveling delivery device of FIG. 57A.

In another embodiment, as depicted in cross-section in FIG. 57A and in bottom view in FIG. 57B (section line A-A in FIG. 57B indicates the location of the cross-section of FIG. 57A), a lumen-traveling delivery device 3400 may include an exterior region 3402 having at least a perimeter 3404 configured to seal against a lumen wall 3406 to form a chamber 3408 between the lumen wall 3406 and the exterior portion 3402. Lumen-traveling delivery device 3400 may include material release portion 3410 configured to release a material into chamber 3408. At least perimeter 3404 may be configured to seal against lumen wall 3406, e.g. through the use of various types of tissue adhesives or through binding to a resident adhesion molecule, including, but not limited to a cadherin or lectin, an integrin, or a member of the immunoglobulin superfamily like N-CAM (neural cell adhesion molecule) or ICAM (intercellular adhesion molecule).

Figure 58A:
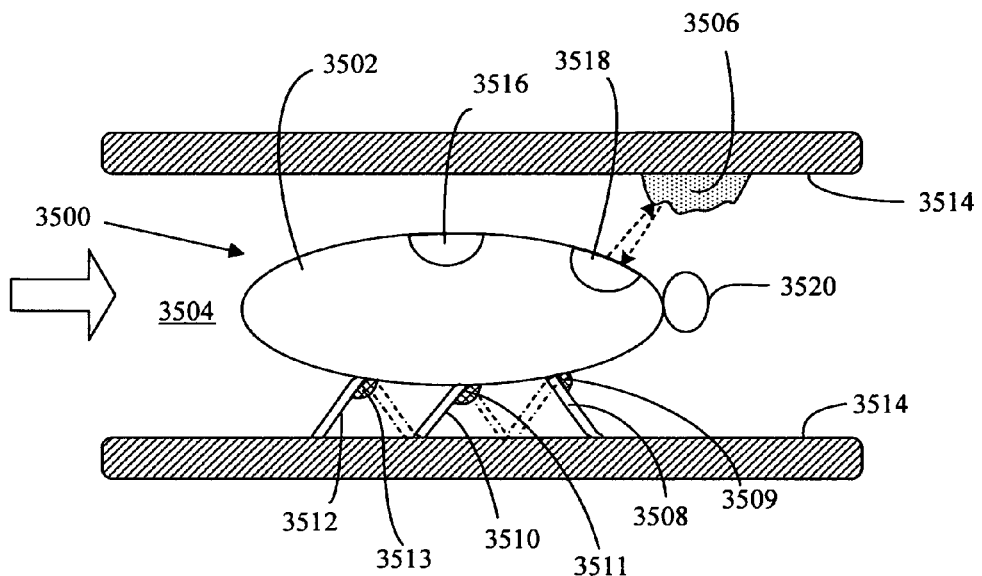
FIGS. 58A and 58B illustrate another embodiment of a lumen-traveling delivery device.
Figure 58B:
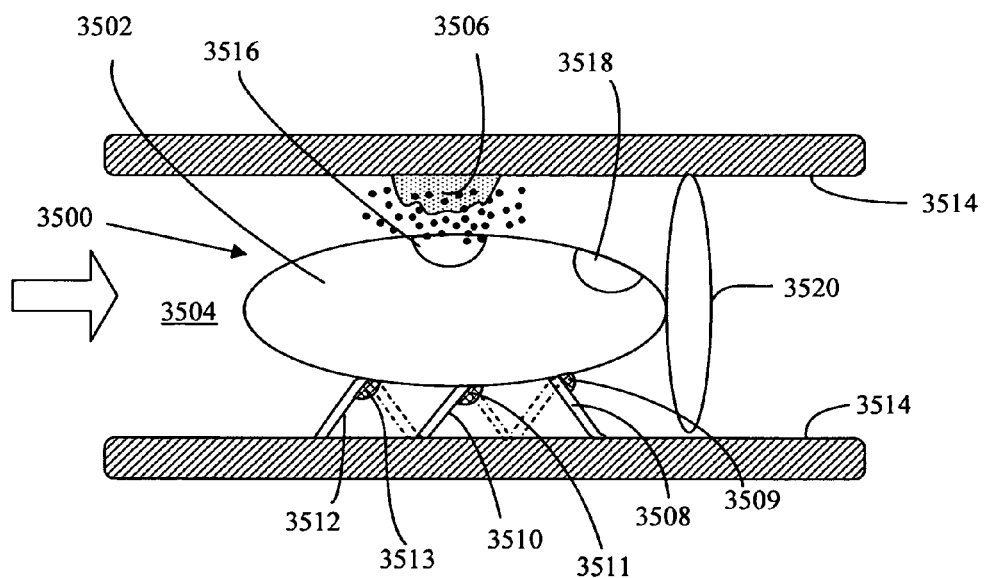

FIGS. 58A and 58B illustrate a further embodiment of a lumen-traveling delivery device 3500, which includes a structural element 3502 sized to fit within body lumen 3504 in the vicinity of treatment target 3506; at least two wall-engaging structures (e.g., legs 3508, 3510, and 3512) operable to alternately engage and disengage a wall of the body lumen; a propelling mechanism capable of producing relative extension and retraction of the at least two wall-engaging structures with respect to each other in combination with alternate engagement and disengagement of the body lumen wall to produce movement of the lumen-traveling stimulation device with respect to the body lumen wall (in the present example, the propelling mechanism includes actuators 3509, 3511, and 3513); and a material release portion 3516 configured to release a deliverable material. Material release portion 3516 may be configured to release the deliverable material when the lumen-traveling delivery device may be located in the vicinity of the treatment target 3506. The treatment target 3506 may include various structures, for example a plaque, as depicted in FIGS. 58A and 58B. Lumen-traveling delivery device 3500 may include sensor 3518 for detecting a condition of interest indicative of the proximity of the lumen-traveling delivery device 3500 to treatment target 3506.

Lumen-traveling delivery device 3500 may include a blocking portion 3520 (shown in contracted form in FIG. 58A) that is capable of expanding or extending, as illustrated in FIG. 58B, to seal against body lumen wall 3514 at least temporarily to at least partially block the flow of fluid through body lumen 3504. In some embodiments, lumen-traveling delivery device 3500 may include a flow-modulating element (e.g., as depicted in FIGS. 10A-10H) configured to at least temporarily alter the flow of fluid within the body lumen.

As described in connection with other embodiments, lumen-traveling delivery device 3500 may include a permeability enhancer for enhancing the permeability of the wall of the lumen in the vicinity of the treatment target, such as a mechanical permeability enhancer, a chemical permeability enhancer, an acoustical permeability enhancer, a magnetic permeability enhancer, or an electrical permeability enhancer, and which may be capable of enhancing the permeability of the blood-brain barrier in the vicinity of the treatment target, for example.

Figure 59:
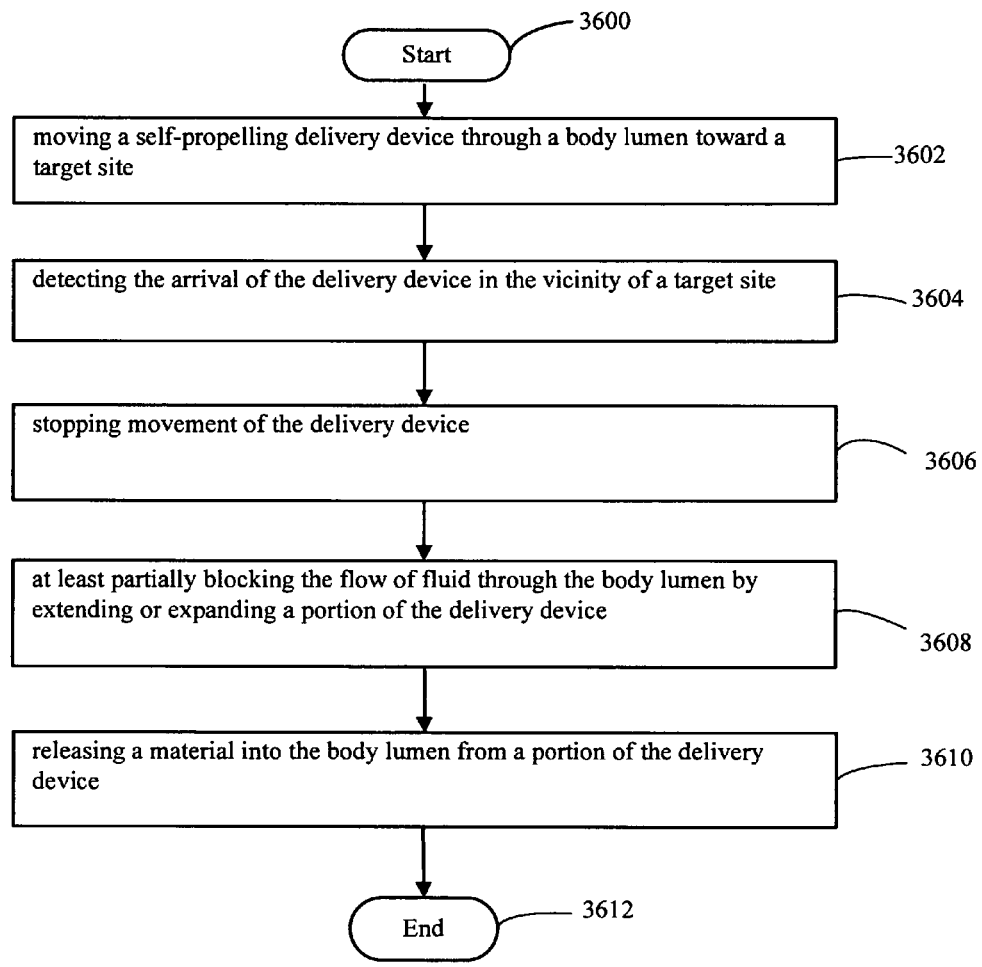
FIG. 59 is a flow diagram of a method of delivering a material to a subject.

FIG. 59 depicts a method of delivering a material to a subject, which includes the steps of moving a self-propelling delivery device through a body lumen toward a target site at 3602; detecting the arrival of the delivery device in the vicinity of a target site at 3604; stopping movement of the delivery device at 3606; at least partially blocking the flow of fluid through the body lumen by extending or expanding a portion of the delivery device at 3608; and releasing a material into the body lumen from a portion of the delivery device at 3610. A delivery device of the type depicted in FIGS. 58A and 58B, for example, may be used in this method. The method may include the step of introducing the delivery device into the body lumen, for example by injection with a syringe or introducing the device with a catheter. The material released into the body lumen from a portion of the delivery device may include at least one of an adhesive, a filler, a hydrogel, an antibiotic, a pharmaceutical compound, a nutrient, a hormone, a growth factor, a medication, a therapeutic compound, an enzyme, a protein, a genetic material, a cell, a fraction of a cell, a vaccine, a vitamin, a neurotransmitter, a neurotropic agent, a neuroactive material, a cytokine, a cell-signaling material, a pro-apoptotic agent, an anti-apoptotic agent, an immunological mediator, an anti-inflammatory agent, a salt, an ion, an antioxidant, an imaging agent, a labeling agent, a diagnostic compound, a nanomaterial, an inhibitor, or a blocker.

Figure 60:
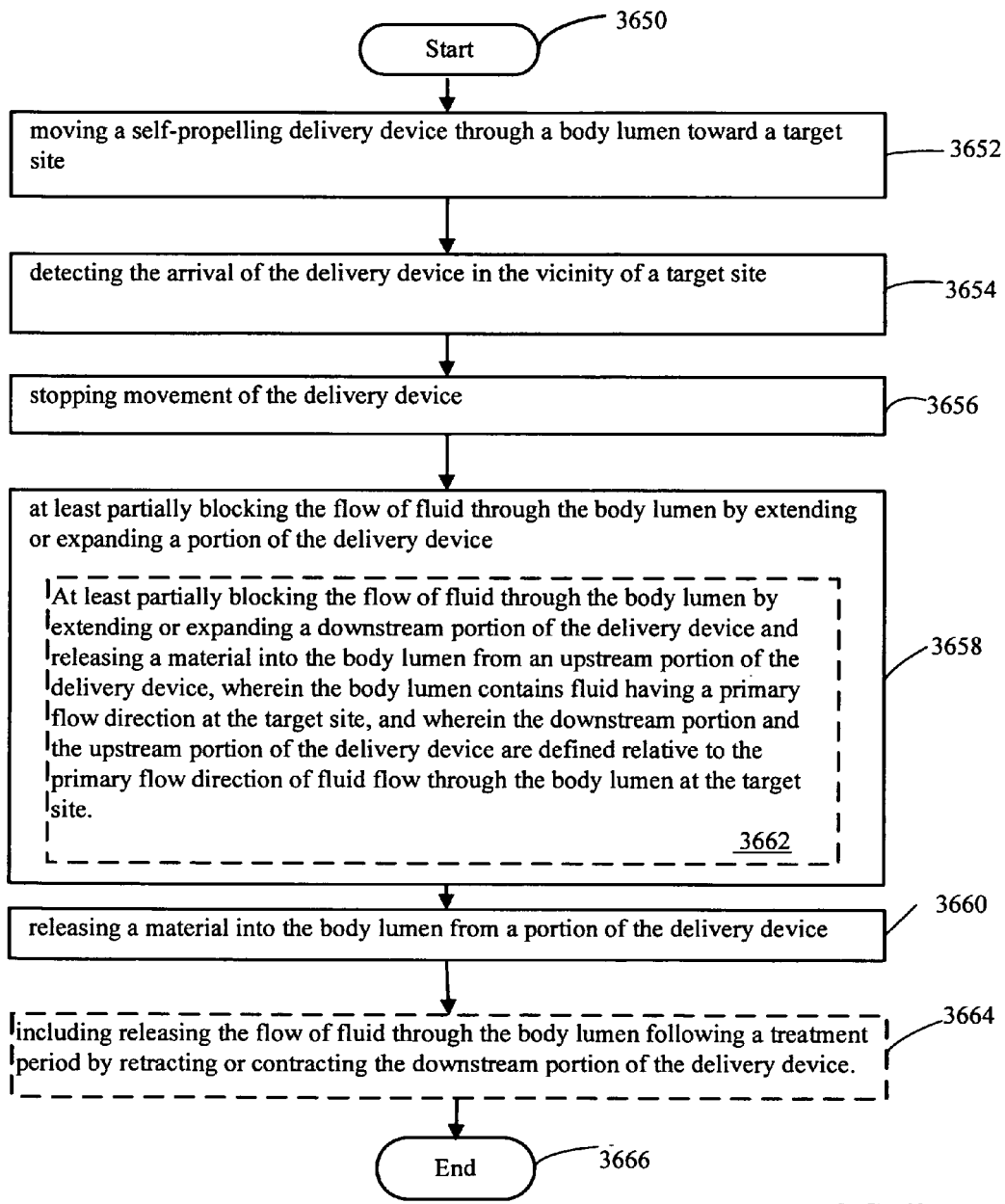
FIG. 60 is a flow diagram showing variants of the method of FIG. 59.

FIG. 60 depicts a variant of the method of FIG. 59 and includes steps of moving a self-propelling delivery device through a body lumen toward a target site at 3652; detecting the arrival of the delivery device in the vicinity of a target site at 3654; stopping movement of the delivery device at 3656; at least partially blocking the flow of fluid through the body lumen by extending or expanding a portion of the delivery device at 3658; and releasing a material into the body lumen from a portion of the delivery device at 3660. As indicated in step 3662, at least partially blocking the flow of fluid through the body lumen may be accomplished by extending or expanding a downstream portion of the delivery device and releasing a material into the body lumen from an upstream portion of the delivery device, wherein the body lumen contains fluid having a primary flow direction at the target site, and wherein the downstream portion and the upstream portion of the delivery device are defined relative to the primary flow direction of fluid flow through the body lumen at the target site. As shown in step 3664, the method may also include releasing the flow of fluid through the body lumen following a treatment period by retracting or contracting the downstream portion of the delivery device.

Figure 61:
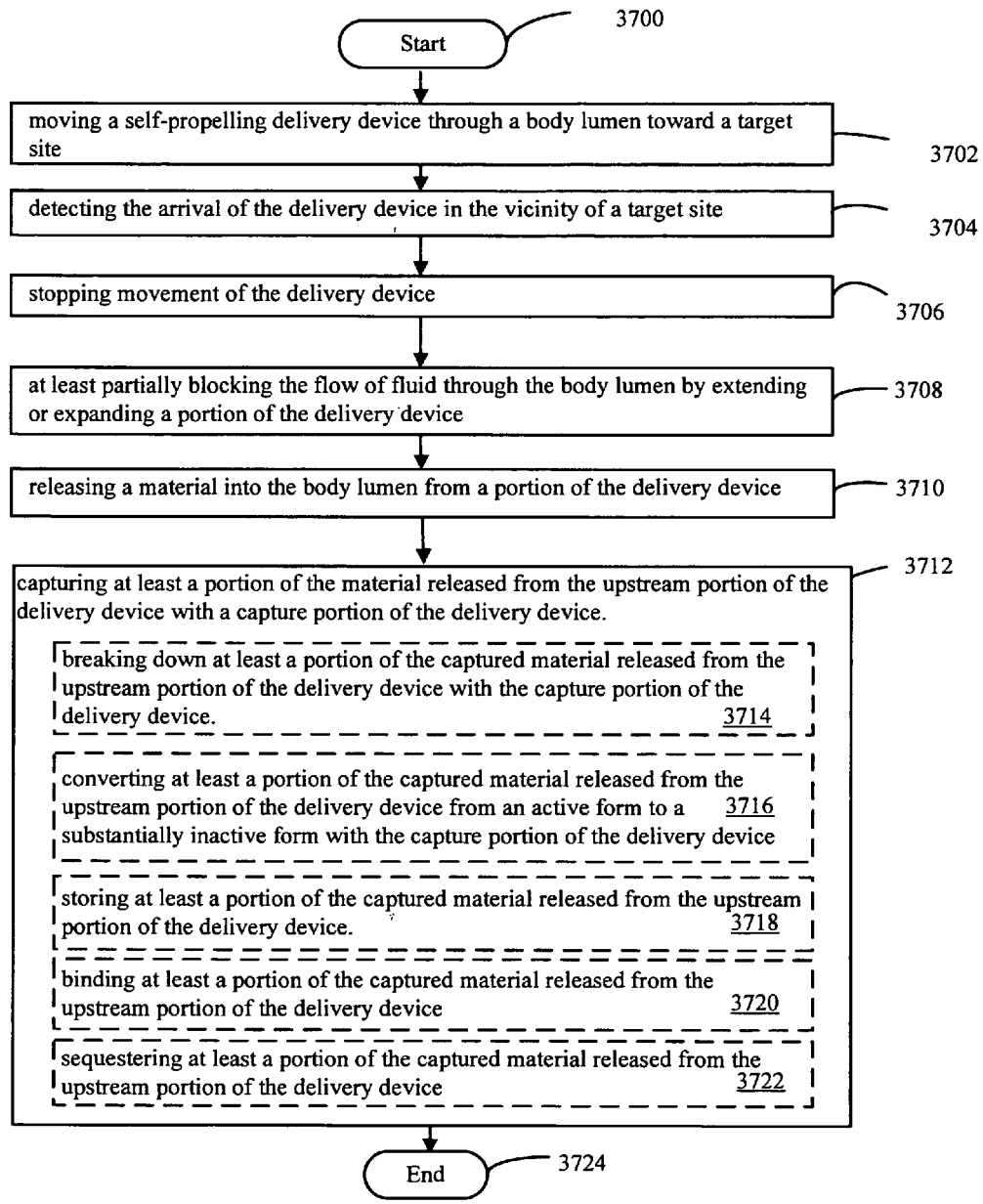
FIG. 61 is a flow diagram showing further variants of the method of FIG. 59.

In a further variant of the method, as shown in FIG. 61, following the steps of moving a self-propelling delivery device through a body lumen toward a target site at 3702; detecting the arrival of the delivery device in the vicinity of a target site at 3704; stopping movement of the delivery device at 3706; at least partially blocking the flow of fluid through the body lumen by extending or expanding a portion of the delivery device at 3708; and releasing a material into the body lumen from a portion of the delivery device at 3710, the method may include capturing at least a portion of the material released from the upstream portion of the delivery device with a capture portion of the delivery device at 3712. The captured material may then be handled in a variety of ways, as indicated by the dashed boxes in 3712: at least a portion of it may be broken down, as indicated at 3714, converted from an active form to a substantially inactive form with the capture portion of the delivery device, as indicated at 3716, stored, as indicated at 3718, bound, as indicated at 3720 or sequestered, as indicated at 3722. The captured material may be broken down by an enzyme or catalyst, or broken down by mechanical, thermal, acoustic treatment, for example, or other disruptive treatments. Conversion of the captured material from active to inactive form may be through various chemical, mechanical, or thermal mechanisms, for example. The captured material may be bound by various types of specific or non-specific binding materials, as described previously. It may be stored in bulk or stored by being bound, sequestered, absorbed, adsorbed, etc. In some alternative embodiments, the material released from the upstream portion of the delivery device may be broken down or converted from an active form to a substantially inactive form without first being captured by the delivery device. For example, and without limitation, the material may be broken down or converted by an enzyme, catalyst, reactant, binding material, etc. released by the delivery device, or by electromagnetic, acoustic, thermal, or optical energy released from the delivery device.

The material released into the body lumen from the portion of the delivery device (e.g., as in step 3610 of FIG. 59) may include a material previously collected within the body of the subject, e.g., by a capturing as described herein, and stored, sequestered, absorbed, adsorbed, etc. in or on the delivery device.

Figure 62:
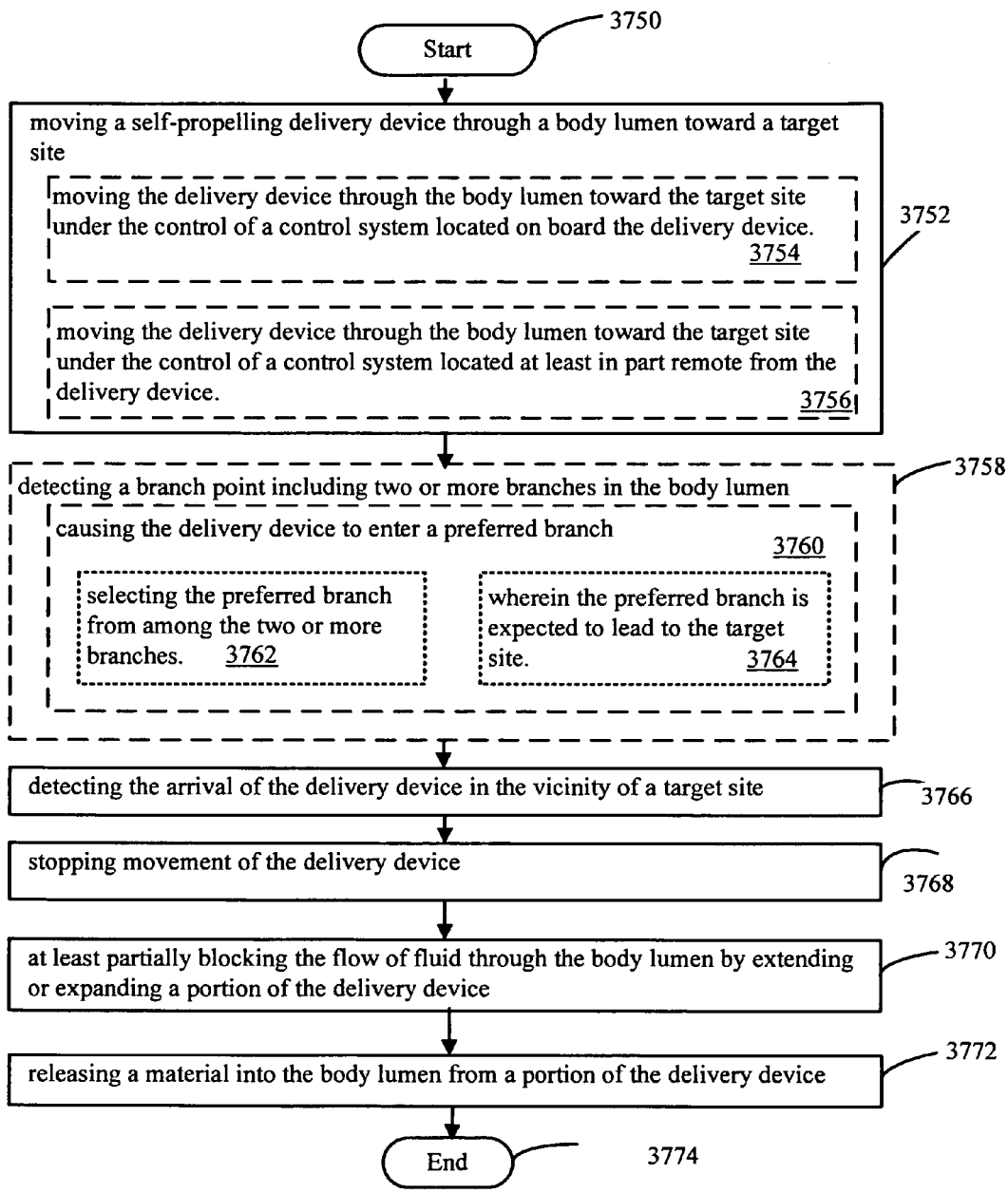
FIG. 62 is a flow diagram showing further variants of the method of FIG. 59.

FIG. 62 includes the steps of moving a self-propelling delivery device through a body lumen toward a target site at 3752; detecting the arrival of the delivery device in the vicinity of a target site at 3766; stopping movement of the delivery device at 3768; at least partially blocking the flow of fluid through the body lumen by extending or expanding a portion of the delivery device at 3770; and releasing a material into the body lumen from a portion of the delivery device at 3772. Moving the self-propelling delivery device through a body lumen toward a target site may include moving the delivery device through the body lumen toward the target site under the control of a control system located on board the delivery device, as indicated at 3754, or moving the delivery device through the body lumen toward the target site under the control of a control system located at least in part remote from the delivery device, as indicated at 3756. The method may include detecting a branch point including two or more branches in the body lumen at step 3758, and causing the delivery device to enter a preferred branch at step 3760. The method may include selecting the preferred branch from among the two or more branches, as indicated at step 3762; in some cases, the preferred branch may be one that is expected to lead to the target site, as indicated at 3764. As used herein, the term 'self-propelling delivery device' refers to a delivery device that includes a propelling mechanism on or connected to the delivery device, a number of examples of which are provided herein. The phrase 'moving the delivery device' encompasses using or controlling such a propelling mechanism to produce movement of the device, and may include motion that is generated and controlled entirely or partially from within or on board the device.

Figure 63:
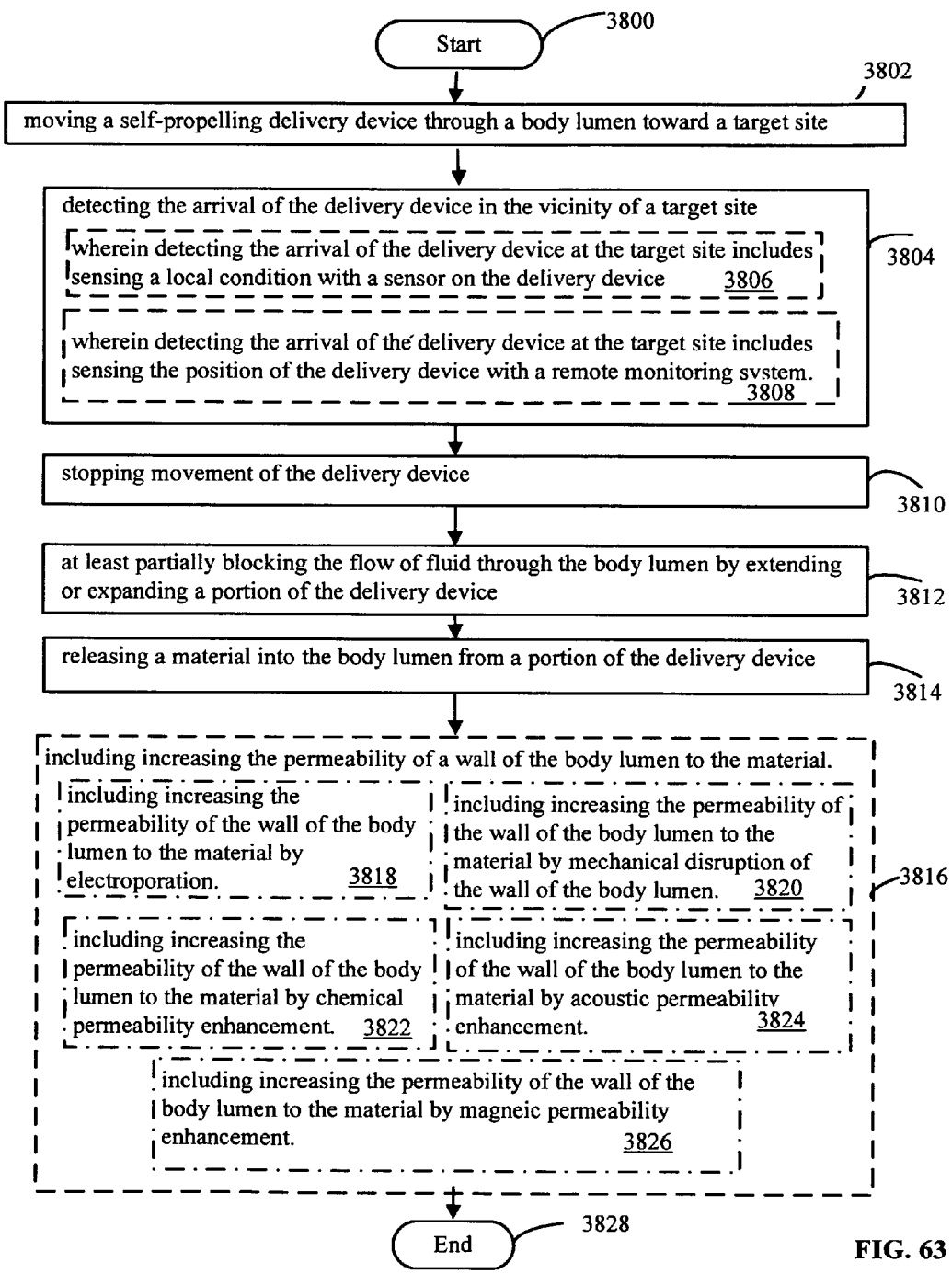
FIG. 63 is a flow diagram showing further variants of the method of FIG. 59.

FIG. 63 shows additional steps of a method of delivering a material to a subject. The method includes moving a self-propelling delivery device through a body lumen toward a target site at 3802 and detecting the arrival of the delivery device in the vicinity of a target site at 3804. Detecting the arrival of the delivery device at the target site may include sensing a local condition with a sensor on the delivery device, as indicated at 3806, or sensing the position of the delivery device with a remote monitoring system, as indicated at 3808. The method depicted in FIG. 63 also includes stopping movement of the delivery device at 3810, at least partially blocking the flow of fluid through the body lumen by extending or expanding a portion of the delivery device at 3812, and releasing a material into the body lumen from a portion of the delivery device at 3814. As indicated at step 3816, the method may include increasing the permeability of a wall of the body lumen to the material, for example by electroporation (at 3818), mechanical disruption of the wall of the body lumen (at 3820), or chemical, acoustic, or magnetic permeability enhancement (at 3822, 3824, and 3826, respectively), as described elsewhere herein. Mechanical disruption refers to any type of mechanical manipulation or treatment of the wall of the body lumen, including mechanical penetration, manipulation, permeation, stretching, or any type of mechanical handling that either reversibly or irreversibly modifies the permeability of the wall. In some embodiments of the method, increasing the permeability of the wall of the body lumen to the material at step 3816 may be performed after releasing the material into the body lumen from a portion of the delivery device (step 3814), as depicted in the flow diagram of FIG. 63. In other embodiments, the permeability of the wall of the body lumen may be increased before the material is released, or at the same time as the material is released. The body lumen through which the self-propelling delivery device is moved, in methods as outlined in FIGS. 59-63, may be a blood vessel, a portion of the CSF space (e.g., spinal canal, cerebral ventricles, sub-arachnoid space), a portion of the respiratory tract, a portion of the urinary tract, a portion of a male or female reproductive tract, a portion of a gastrointestinal tract, or various other body lumens as discussed elsewhere herein.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via application Ser. Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will recognize that electro-mechanical as used herein is not necessarily limited to a system that has both electrical and mechanical actuation except as context may dictate otherwise. Non-electrical analogs of electrical circuitry may include fluid circuitry, electro-mechanical circuitry, mechanical circuitry, and various combinations thereof.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A lumen-traveling delivery device comprising:
a propelling mechanism;
a material release portion configured to release a deliverable material;
a capture portion distinct from the material release portion and capable of capturing the deliverable material released from the material release portion;
an expanding or extending portion positioned downstream of the material release portion and the capture portion and configured to at least temporarily seal with a wall of a body lumen in the vicinity of a treatment target to completely block a flow of fluid through the body lumen to keep the deliverable material released from the material release portion in the vicinity of the delivery device to be captured by the capture portion; and control circuitry located at least in part on the delivery device, the control circuitry capable of controlling the operation of the propelling mechanism to move the delivery device through the body lumen to the treatment target, controlling the material release portion to release a deliverable material and controlling the capture portion.

2. The device of claim 1, wherein the control circuitry is capable of controlling the material release portion to release the deliverable material when the delivery device is in the vicinity of the treatment target.

3. The device of claim 1, wherein the delivery device includes a sensor capable of generating a sense signal upon detection of a condition of interest, and wherein the control circuitry is configured to receive the sense signal and control at least one of the operation of the propelling mechanism and the material release portion based upon receipt of the sense signal.

4. The device of claim 3, wherein the sensor is capable of generating a sense signal upon detection of a local condition of interest.

5. The device of claim 1, including at least a first lumen-wall-engaging structure and a second lumen-wall-engaging structure, wherein the propelling mechanism produces lengthening and shortening of the delivery device between the first lumen-wall-engaging structure and the second lumen-wall-engaging structure in coordination with alternate engagement and disengagement of the first lumen-wall-engaging structure and the second lumen-wall-engaging structure.

6. The device of claim 1, including a steering mechanism capable of modifying the movement of the delivery device.

7. The lumen-traveling delivery device of claim 1, including an exterior region having at least a perimeter configured to seal against a lumen wall to form a chamber between the lumen wall and the exterior portion, and including a material release portion configured to release a material into the chamber.

8. The device of claim 1, wherein the delivery device includes a structural element sized to fit within a body lumen in the vicinity of a treatment target, the structural element including at least one of a substantially tubular structure, multiple openings in fluid communication with the body lumen, a capsule-like structure, a self-expanding material, a resilient material, a mesh-like material, a biocompatible material, or a slotted structure.

9. The device of claim 1, wherein the propelling mechanism includes at least one of a peristaltic propelling mechanism, two or more alternately activated limbs, or at least one rotating lumen-wall-engaging structure.

10. The device of claim 1, wherein the material release portion includes at least one of a reservoir containing the deliverable material and including a rupturable barrier, a reservoir containing the deliverable material and including a barrier having a controllable permeability, or the deliverable material in a carrier material.

11. The device of claim 1, including a flow-modulating element configured to at least temporarily alter the flow of fluid within the body lumen.

12. The device of claim 1, including a permeability enhancer for enhancing the permeability of the wall of the lumen in the vicinity of the treatment target.

13. The device of claim 1, including a permeability enhancer for enhancing the permeability of the wall of the lumen in the vicinity of the treatment target, wherein the permeability enhancer includes at least one of a mechanical permeability enhancer, a chemical permeability enhancer, an electrical permeability enhancer, an acoustic permeability enhancer, a magnetic permeability enhancer, or a permeability enhancer capable of enhancing the permeability of the blood-brain barrier in the vicinity of the treatment target.

14. A lumen-traveling delivery device comprising:
a structural element sized to fit within a body lumen in the vicinity of a treatment target;
at least two wall-engaging structures operable to alternately engage and disengage a wall of the body lumen;
a propelling mechanism capable of producing relative extension and retraction of the at least two wall-engaging structures with respect to each other in combination with alternate engagement and disengagement of the body lumen wall to produce movement of the lumen-traveling delivery device with respect to the body lumen wall;
a material release portion configured to release a deliverable material;
a capture portion distinct from the material release portion and capable of capturing the deliverable material released from the material release portion; and
an expanding or extending portion positioned downstream of the material release portion and the capture portion and configured to at least temporarily seal with a wall of the body lumen in the vicinity of the treatment target to completely block a flow of fluid through the body lumen to keep the deliverable material released from the material release portion in the vicinity of the delivery device to be captured by the capture portion.

15. The lumen-traveling delivery device of claim 14, wherein the material release portion is configured to release a deliverable material when the lumen-traveling delivery device is located in the vicinity of the treatment target.

16. The lumen-traveling delivery device of claim 14, including at least one of a sensor for detecting a condition of interest indicative of the proximity of the lumen-traveling delivery device to the treatment target, a permeability enhancer for enhancing the permeability of the wall of the lumen in the vicinity of the treatment target, or a flow-modulating element configured to at least temporarily alter the flow of fluid within the body lumen.

17. The lumen-traveling delivery device of claim 14, including a permeability enhancer for enhancing the permeability of the wall of the lumen in the vicinity of the treatment target, the permeability enhancer including at least one of a mechanical permeability enhancer, a chemical permeability enhancer, an electrical permeability enhancer, an acoustic permeability enhancer, a magnetic permeability enhancer, or a permeability enhancer capable of enhancing the permeability of the blood-brain barrier in the vicinity of the treatment target.

18. A method of delivering a material to a subject, comprising:
moving a self-propelling delivery device through a body lumen toward a target site;
detecting the arrival of the delivery device in the vicinity of a target site;
stopping movement of the delivery device in the vicinity of the target site;
completely blocking the flow of fluid through the body lumen in the vicinity of the target site by extending or expanding a portion of the delivery device to at least temporarily seal with a wall of the body lumen;

after blocking the flow of fluid, releasing a material into the body lumen from a material release portion of the delivery device; and capturing at least a portion of the material released from the material release portion with a capture portion of the delivery device distinct from the material release portion;

wherein blocking the flow of fluid through the body lumen causes the material released from the material release portion to remain in the vicinity of the delivery device to be captured by the capture portion.

19. The method of claim 18, including completely blocking the flow of fluid through the body lumen by extending or expanding a downstream portion of the delivery device and releasing a material into the body lumen from an upstream portion of the delivery device, wherein the body lumen contains fluid having a primary flow direction at the target site, and wherein the downstream portion and the upstream portion of the delivery device are defined relative to the primary flow direction of fluid flow through the body lumen at the target site.

20. The method of claim 19, including at least one of breaking down at least a portion of the material released from the upstream portion of the delivery device, converting at least a portion of the material released from the upstream portion of the delivery device from an active form to a substantially inactive form, or capturing at least a portion of the material released from the upstream portion of the delivery device with a capture portion of the delivery device.

21. The method of claim 19, capturing at least a portion of the material released from the upstream portion of the delivery device with a capture portion of the delivery device and performing at least one of at least one of breaking down at least a portion of the captured material released from the upstream portion of the delivery device with the capture portion of the delivery device, converting at least a portion of the captured material released from the upstream portion of the delivery device from an active form to a substantially inactive form with the capture portion of the delivery device, storing at least a portion of the captured material released from the upstream portion of the delivery device, binding at least a portion of the captured material released from the upstream portion of the delivery device, or sequestering at least a portion of the captured material released from the upstream portion of the delivery device.

22. The method of claim 18, including moving the delivery device through the body lumen toward the target site under the control of a control system located on board the delivery device.

23. The method of claim 18, including:
detecting a branch point including two or more branches in the body lumen;
selecting a preferred branch from among the two or more branches; and
causing the delivery device to enter the preferred branch.

24. The method of claim 18, wherein detecting the arrival of the delivery device at the target site includes at least one of sensing a local condition with a sensor on the delivery device or sensing the position of the delivery device with a remote monitoring system.

25. The method of claim 18, including increasing the permeability of a wall of the body lumen to the material by at least one of electroporation, iontophoresis, mechanical disruption of the wall of the body lumen, or chemical permeability enhancement.

26. The method of claim 18, wherein the body lumen includes at least one of a blood vessel, a CSF space, a portion of the respiratory tract, a portion of the urinary tract, a portion of a reproductive tract, or a portion of a digestive tract.

27. The method of claim 18, wherein the material includes at least one of an adhesive, a filler, a hydrogel, an antibiotic, a pharmaceutical compound, a nutrient, a hormone, a growth factor, a medication, a therapeutic compound, an enzyme, a protein, a genetic material, a cell, a fraction of a cell, a vaccine, a vitamin, a neurotransmitter, a neurotropic agent, a neuroactive material, a cytokine, a cell-signaling material, a pro-apoptotic agent, an anti-apoptotic agent, an immunological mediator, an anti-inflammatory agent, a salt, an ion, an antioxidant, an imaging agent, a labeling agent, a diagnostic compound, a nanomaterial, an inhibitor, a blocker, or a material previously collected within the body of the subject.

28. A lumen traveling device comprising:
a structural element sized to fit within a body lumen;
a propelling mechanism;
an exterior region of the structural element having a perimeter configured to seal against a lumen wall to form a chamber between the lumen wall and the exterior region, the perimeter including at least one tissue adhesive;
a material release portion configured to release a deliverable material into the chamber;
a capture portion capable of capturing the deliverable material released from the material release portion; and
control circuitry located at least in part on the delivery device, the control circuitry capable of controlling the operation of the propelling mechanism to move the delivery device through the body lumen to a treatment target, controlling the material release portion to release the deliverable material and controlling the capture portion.

29. A method of delivering a material to a subject, comprising:
moving a self-propelling delivery device through a body lumen toward a target site;
detecting the arrival of the delivery device in the vicinity of a target site;
stopping movement of the delivery device in the vicinity of the target site;
forming a chamber between a lumen wall and an exterior region of the delivery device, the exterior region having at least a perimeter including at least one tissue adhesive configured to seal against the lumen wall;
releasing a material into the chamber from a material release portion of the delivery device; and
capturing at least a portion of the material released from the material release portion with a capture portion distinct from the material release portion.

* * * * *